United States Patent [19]
Wagner et al.

[11] Patent Number: 6,069,144
[45] Date of Patent: May 30, 2000

[54] N-HETEROCYCLIC COMPOUNDS, INTERMEDIATE PRODUCTS USED TO PREPARE THEM, AGENTS CONTAINING THEM AND THEIR USE IN ANTIFUNGAL APPLICATIONS

[75] Inventors: Oliver Wagner, Bexbach; Frank Wetterich, Mutterstadt; Karl Eicken, Wachenheim; Michael Rack, Heidelberg; Gerhard Hamprecht, Weinheim; Gunther Lamm, Hassloch; John-Bryan Speakman, Bobenheim; Gisela Lorenz, Hambach; Eberhard Ammermann, Heppenheim; Siegfried Strathmann, Limburgerhof, all of Germany

[73] Assignee: BASF Aktiengesellschaft, Ludwigshafen, Germany

[21] Appl. No.: 09/011,610

[22] PCT Filed: Aug. 21, 1996

[86] PCT No.: PCT/EP96/03680

§ 371 Date: Feb. 12, 1998

§ 102(e) Date: Feb. 12, 1998

[87] PCT Pub. No.: WO97/08147

PCT Pub. Date: Mar. 6, 1997

[30] Foreign Application Priority Data

Aug. 24, 1995 [DE] Germany ............. 195 31 148

[51] Int. Cl.[7] ............. A01N 43/58; A61K 31/505; C07D 515/02; C07D 215/16; C07D 211/36
[52] U.S. Cl. ............. 514/252; 514/256; 514/373; 546/114; 546/157; 546/243
[58] Field of Search ............. 546/144, 157, 546/243; 514/373, 252, 256

[56] References Cited

U.S. PATENT DOCUMENTS

| | | | |
|---|---|---|---|
| 2,513,922 | 7/1950 | Downey | 260/302 |
| 2,912,357 | 11/1959 | Harman | 167/33 |
| 4,294,835 | 10/1981 | Nakagawa et al. | 424/263 |
| 4,551,460 | 11/1985 | Tilley | 514/267 |
| 4,605,432 | 8/1986 | Adams, Jr. | 71/92 |
| 4,659,722 | 4/1987 | Nakagawa et al. | 514/332 |
| 5,389,658 | 2/1995 | Takatani et al. | 514/373 |
| 5,457,106 | 10/1995 | Takatani et al. | 514/230.5 |
| 5,561,147 | 10/1996 | Takatani et al. | 514/340 |
| 5,767,121 | 6/1998 | Takatani et al. | 514/259 |

FOREIGN PATENT DOCUMENTS

| | | |
|---|---|---|
| 6939881 | 4/1994 | Australia . |
| 593998 | 4/1997 | European Pat. Off. . |
| 4059754 | 6/1990 | Japan . |
| 94/06783 | 3/1994 | WIPO . |

OTHER PUBLICATIONS

Stanton et. al., "A Novel Class of Fungicides ...", J. Agric. Food Chem., 1983, vol. 31, pp. 451–453.

*Tetrahedron*, vol. 39, No. 24, pp. 4153–4161, 1983.

Dunn et al., *J. Heterocycl. Chem.*, vol. 24, NE, pp. 85–89, 1987.

Baudin et al., *Bull. Soc. Chim. Fr.*, vol. 130, 1993, pp. 336–357.

Mosher et al., *Organic Synth, Col.* vol. IV, 1963, pp. 828–831.

Taylor et al., *Org. Synth. Coll.* vol. IV, 1963, pp. 704–707.

*Chem. Abst.*, vol. 85, 1976 (AN 46573x).

*Pharmazie*, vol. 48, no. 8, 1993, pp. 588–591 (and English translation).

*Chem. Abst.*, vol. 97, 1982 (AN 55704).

*Chem. Abst.*, vol. 76, 1972 (AN 45316).

*Primary Examiner*—Mukund J. Shah
*Assistant Examiner*—Tamthom N. Truong
*Attorney, Agent, or Firm*—Keil & Weinkauf

[57] ABSTRACT

N-heterocyclic compounds I (I)

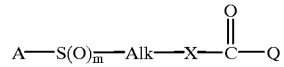

or their salts or N-oxides, wherein

A is an N-heterocycle selected from the group consisting of (A1)

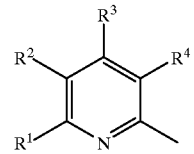

(A8)

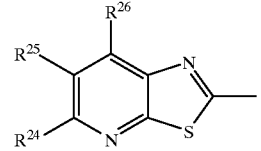

(A9)

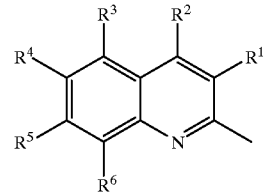

$R^1$–$R^6$, $R^{24}$–$R^{26}$ are hydrogen, cyano, nitro, halogen, aminocarbonyl, methylsulfonyl, alkyl, haloalkyl, alkoxy, haloalkoxy, alkylthio, alkoxyalkyl, alkoxycarbonyl, aryl or aryloxy;

m is 0, 1 or 2;

Alk is optionally substituted 1,2-ethylidene, 1,3-propylidene cycloalkyl or cycloalkenyl;

X is oxygen or sulfur;

Q is optionally substituted aryl, cycloalkyl, cycloalkenyl, or arylalkyl;

their manufacture and suitable intermediates therefore, as well as compositions comprising them and their use for controlling harmful fungi.

20 Claims, No Drawings

N-HETEROCYCLIC COMPOUNDS, INTERMEDIATE PRODUCTS USED TO PREPARE THEM, AGENTS CONTAINING THEM AND THEIR USE IN ANTIFUNGAL APPLICATIONS

This is a 371 application of PCT/EP96/03680, filed on Aug. 21, 1996.

The present invention relates to N-heterocyclic compounds of the general formula I

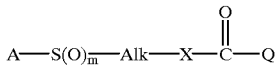
(I)

and to their salts and N-oxides, where the variables have the following meanings:

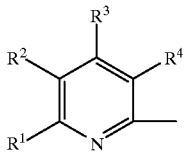 (A1)

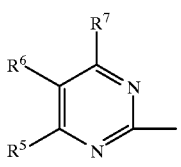 (A2)

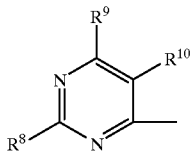 (A3)

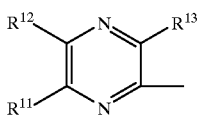 (A4)

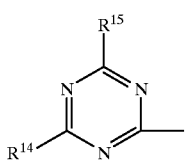 (A5)

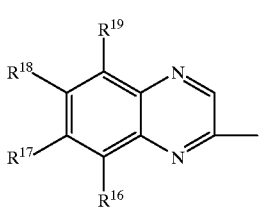 (A6)

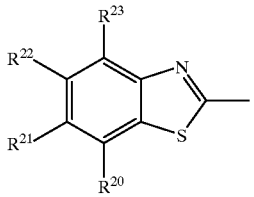 (A7)

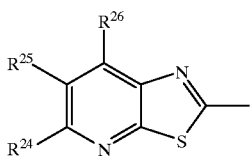 (A8)

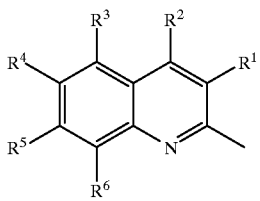 (A9)

where the groups $R^1$ to $R^{26}$ independently of one another are: hydrogen, cyano, nitro, halogen, aminocarbonyl, methylsulfonyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxy-$C_1$–$C_4$-alkyl, ($C_1$–$C_4$-alkoxy)carbonyl, aryl, aryloxy or hetaryl, it being possible for the aryl and hetaryl rings to be unsubstituted or to have attached to them one to three groups, in each case selected from amongst: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxy-$C_1$–$C_4$-alkyl, ($C_1$–$C_4$-alkoxy)carbonyl and $C_1$–$C_4$-acyl;

m is 0, 1 or 2;

Alk is 1,2-ethylidene or 1,3-propylidene, it being possible for the hydrogen atoms of these chains to be replaced independently of one another by one of the following groups:

$C_1$–$C_8$-alkyl, $C_1$–$C_8$-haloalkyl, $C_2$–$C_8$-alkenyl, $C_2$–$C_8$-haloalkenyl or $C_2$–$C_8$-alkynyl, it being possible for each of these 5 radicals additionally to have attached to them one to three groups, in each case selected from amongst: cyano, $C_1$–$C_4$-alkoxy, $C_1$–$C_4$-haloalkoxy, $C_1$–$C_4$-alkylthio, ($C_1$–$C_4$-alkoxy)carbonyl, $C_3$–$C_7$-cycloalkyl and $C_5$–$C_7$-cycloalkenyl;

$C_3$–$C_7$-cycloalkyl or $C_5$–$C_7$-cycloalkenyl, it being possible for these radicals to be partially or fully halogenated or to have attached to them one to three groups, in each case selected from amongst: cyano, halogen, $C_1$–$C_4$-alkyl, $C_1$–$C_4$-haloalkyl and $C_1$–$C_4$-alkoxy;

X is oxygen, sulfur or —N($R^a$)—, where $R^a$ is hydrogen, $C_1$–$C_8$-alkyl or $C_3$–$C_7$-cycloalkyl;

Q is aryl or hetaryl, it being possible for these rings to be unsubstituted or to have attached to them one to three groups, in each case selected from amongst: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$- alkoxy-$C_1$–$C_4$-alkyl, ($C_1$–$C_4$-alkoxy)carbonyl, $C_1$–$C_4$-acyl, $C_1$–$C_4$-alkylsulfynyl, $C_1$–$C_4$-alkylsulfonyl, aryl, aryloxy and hetaryl, it being possible for these aryl and hetaryl rings, in turn, additionally to have attached to them one to three substituents, in each case selected from amongst: cyano, nitro, halogen, $C_1$–$C_4$-alkyl, $C_1$–$C_4$-alkoxy-$C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, ($C_1$–$C_4$-alkoxy)carbonyl and $C_1$–$C_4$-acyl; $C_3$–$C_7$-cycloalkyl or $C_5$–$C_7$-cycloalkenyl, it being possible for these rings to be unsubstituted, partially or fully halogenated or to have attached to them one to three groups, in each case selected from amongst: cyano, halogen, $C_1$–$C_4$-alkyl, $C_1$–$C_4$-haloalkyl, $C_1$–$C_4$-alkoxy-$C_1$–$C_4$-alkyl, $C_1$–$C_4$-alkoxy, $C_1$–$C_4$-haloalkoxy, $C_1$–$C_4$-alkylthio, ($C_1$–$C_4$-alkoxy)carbonyl, $C_3$–$C_7$-cycloalkyl, $C_5$–$C_7$-cycloalkenyl, aryl, aryloxy and hetaryl, it being possible for these aryl and hetaryl rings, in turn, additionally to have attached to them one to three substituents, in each case selected from amongst: cyano, nitro, halogen, $C_1$–$C_4$-alkyl, $C_1$–$C_4$-haloalkyl, $C_1$–$C_4$-alkoxy-$C_1$–$C_4$-alkyl, $C_1$–$C_4$-alkoxy, $C_1$–$C_4$-haloalkoxy, $C_1$–$C_4$-alkylthio, ($C_1$–$C_4$-alkoxy)carbonyl and $C_1$–$C_4$-acyl;

aryl-$C_1$–$C_4$-alkyl, it being possible for the aryl ring to be unsubstituted or to have attached to it one to three groups, in each case selected from amongst: cyano, nitro, halogen, $C_1$–$C_4$-alkyl, $C_1$–$C_4$-haloalkyl, $C_1$–$C_4$-alkoxy-$C_1$–$C_4$-alkyl, $C_1$–$C_4$-alkoxy, $C_1$–$C_4$-haloalkoxy, $C_1$–$C_4$-alkylthio, ($C_1$–$C_4$-alkoxy)carbonyl, $C_1$–$C_4$-acyl, aryl, aryloxy and hetaryl, it being possible for these aryl and hetaryl rings, in turn, additionally to have attached to them one to three substituents, in each case selected from amongst: cyano, nitro, halogen, $C_1$–$C_4$-alkyl, $C_1$–$C_4$-haloalkyl, $C_1$–$C_4$-alkoxy-$C_1$–$C_4$-alkyl, $C_1$–$C_4$-alkoxy, $C_1$–$C_4$-haloalkoxy, $C_1$–$C_4$-alkylthio, ($C_1$–$C_4$-alkoxy)carbonyl and $C_1$–$C_4$-acyl, with the exception of a) the compounds V1 to V26 where A=A1 and $R^4$=H:

| No. | $R^1$ | $R^2$ | $R^3$ | m | Alk | X | Q |
|---|---|---|---|---|---|---|---|
| V1 | H | H | H | 0 | 1,2-ethylidene | —O— | phenyl |
| V2 | H | H | H | 2 | 1,2-ethylidene | —O— | phenyl |
| V3 | 5-$CF_3$ | H | H | 0 | 1,2-ethylidene | —O— | 4-chlorophenyl |
| V4 | 5-$CF_3$ | H | H | 0 | 1,2-ethylidene | —O— | 4-methylphenyl |
| V5 | 5-$CF_3$ | H | H | 2 | 1,2-ethylidene | —O— | phenyl |
| V6 | 5-$CF_3$ | H | H | 2 | 1,2-ethylidene | —O— | 2-chlorophenyl |
| V7 | 5-$CF_3$ | H | H | 2 | 1,2-ethylidene | —O— | 3-chlorophenyl |
| V8 | 5-$CF_3$ | H | H | 2 | 1,2-ethylidene | —O— | 4-chlorophenyl |
| V9 | 5-$CF_3$ | H | H | 2 | 1,2-ethylidene | —O— | 3,4-dichlorophenyl |
| V10 | 5-$CF_3$ | H | H | 2 | 1,2-ethylidene | —O— | 4-methylphenyl |
| V11 | 5-$CF_3$ | H | H | 2 | 1,2-ethylidene | —O— | 4-methoxyphenyl |
| V12 | 5-$CF_3$ | H | H | 2 | 1,2-ethylidene | —O— | 4-trifluoromethylphenyl |
| V13 | 5-$CF_3$ | H | H | 2 | 1,2-ethylidene | —O— | 4-tert-butylphenyl |
| V14 | H | H | H | 2 | 1,2-ethylidene | —O— | 3-chlorophenyl |
| V15 | H | H | 3-Cl | 2 | 1,2-ethylidene | —O— | 3-chlorophenyl |
| V16 | 5-Cl | H | H | 2 | 1,2-ethylidene | —O— | 3-chlorophenyl |
| V17 | 6-Cl | H | H | 2 | 1,2-ethylidene | —O— | 3-chlorophenyl |
| V18 | H | H | 3-CN | 2 | 1,2-ethylidene | —O— | 3-chlorophenyl |
| V19 | H | H | 3-$CF_3$ | 2 | 1,2-ethylidene | —O— | 3-chlorophenyl |
| V20 | H | H | 3-$NO_2$ | 2 | 1,2-ethylidene | —O— | 3-chlorophenyl |
| V21 | 5-$NO_2$ | H | H | 2 | 1,2-ethylidene | —O— | 3-chlorophenyl |
| V22 | 6-$CH_3$ | H | H | 2 | 1,2-ethylidene | —O— | 3-chlorophenyl |
| V23 | 6-$OCH_3$ | H | H | 2 | 1,2-ethylidene | —O— | 3-chlorophenyl |
| V24 | 5-$COOCH_3$ | H | H | 2 | 1,2-ethylidene | —O— | 3-chlorophenyl |
| V25 | 6-$CH_3$ | 4-$CF_3$ | H | 2 | 1,2-ethylidene | —O— | 3-chlorophenyl |
| V26 | 5-$CF_3$ | H | H | 2 | 1,2-ethylidene | —NH— | 4-chlorophenyl | b) the compound I where A is the N-oxide of A1, with $R^1$, $R^2$, $R^3$, $R^4$=H; m=2; Alk=1,2-ethylidene; X=—O—; Q=phenyl, and c) the compounds I where A=A2 and at the same time m=0.

Moreover, the invention relates to compositions which comprise the compounds I, their salts or N-oxides, to a process for the preparation of these compositions and their use, and to the use of the compounds I for controlling harmful fungi and the associated procedure.

The compounds Nos. VI to V26 and the compound I in which A is the N-oxide of A1, $R^1$, $R^2$ and $R^3$ are each hydrogen, m is 2, Alk is 1,2-ethylidene, X is O and Q is phenyl are already known from the catalog: Intermediates 4, 1990; Supplement to Catalog 4, RDfile Product Listing, January 1994, MAYBRIDGE CHEMICAL COMPANY LTD., Trevillett, Tintagel, Cornwall PL34 0HW, United Kingdom.

It was an object of the present invention to provide novel fungicidally active compounds.

Accordingly, we have found the N-heterocyclic compounds of the formula I defined at the outset including their salts and N-oxides. We have also found compositions which comprise the compounds I, their salts or N-oxides, a process for the preparation of these compositions and their use, and the use of the compounds I for controlling harmful fungi and the associated procedure.

The compounds of the formula I can be obtained by various routes, in particular by one of the processes below, which will be illustrated by way of example of those compounds I where A is a radical A1':

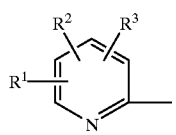 (A1')

1. Reaction of pyridin-2-ylthioethyl or pyridin-2-ylthiopropyl compounds of the formula II with an acid chloride Cl—CO—R⁴:

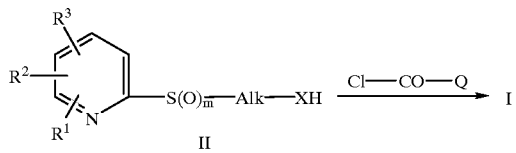

The reaction is generally carried out in a manner known per se {see, for example, Tetrahedron 39 (1983), 4153, J. Heterocycl. Chem. 24, N1 (1987), 85–89, JP-A 04/059 754 and Bull. Soc. Chim. Fr. 130 (1993), 336–357}.

Suitable solvents are, in particular, chlorinated hydrocarbons such as dichloromethane and esters such as ethyl acetate.

The process is usually carried out in the presence of a base, preferably triethylamine.

The reaction temperature is generally at from (–10) to 100, in particular 0 to 40, °C.

2. Oxidation of compounds I where A=A1' and m=0 to give the corresponding compounds I where m=1 or 2 {cf., in this context, Houben-Weyl, Methoden der Organischen Chemie [Methods in Organic Chemistry], Georg Thieme Verlag, Stuttgart, Vol. E11, 4th Edition, 1985, pages 665–850, especially pages 702–718 (Part—Volume I); loc. cit., pages 1129–1256, especially pages 1194–1204 (Part—Colume II); loc. cit., Vol. IX, 4th Edition, 1955, p. 222 et seq.}:

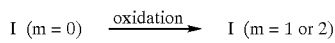

Examples of suitable oxidants are hydrogen peroxide, organic peroxides such as acetyl peroxide, trifluoroacetic peroxide, m-chloroperbenzoic acid, tert-butyl hydroperoxide and tert-butyl hypochlorite, and inorganic compounds such as sodium metaiodate, chromic acid and nitric acid.

Especially suitable for completely oxidizing the sulfur are hydrogen peroxide, organic peroxides such as acetic peroxide, trifluoroacetic peroxide and m-chloroperbenzoic acid, furthermore inorganic oxidants such as potassium permanganate. When using inorganic oxidants, in addition of a catalyst, eg. tungstate, may be beneficial to the course of the reaction.

A mixture of sodium tungstate and hydrogen peroxide has proved particularly useful.

As a rule, the reaction is carried out in an inert solvent, examples of useful substances being, depending on the oxidant, organic acids such as acetic acid, trichloroacetic acid and propionic acid, chlorinated hydrocarbons such as methylene chloride, chloroform and 1,2-dichloroethane, aromatic hydrocarbons or halohydrocarbons such as benzene, chlorobenzene and toluene, protic solvents such as methanol and ethanol, or water. Mixtures of these are also suitable.

The reaction temperature is generally from (–30) °C. to the boiling point of the reaction mixture in question, predominantly in the lower temperature range for partial oxidation of the sulfur, but preferably at from 10° C. to the boiling point for complete oxidation. The process is especially preferably carried out at from 0 to 40° C.

Depending on the desired target product I where m=1 or 2, approximately equimolar amounts or an approximately 2-fold molar excess of oxidant are used.

The compounds of the formula I can be converted into their N-oxides in a manner known per se {cf., for example, A. Albini and S. Pietra, Heterocyclic N-oxides, CRC-Press Inc., Boca Raton, USA 1991; H. S. Mosher et al., Org. Synth. Coll. Vol. IV 1963, page 828; E. C. Taylor et al., Org. Synth. Coll. Vol. IV 1963, page 704; T. W. Bell et al., Synth. 69 (1990), 226}.

Oxidants conventionally used for oxidation which may be mentioned by way of example are peracetic acid, trifluoroperacetic acid, perbenzoic acid, m-chloroperbenzoic acid, monopermaleic acid, magnesium monoperphthalate, sodium perborate, Oxone® (contains peroxodisulfate), pertungstic acid and hydrogen peroxide.

Examples of suitable solvents are water, sulfuric acid, carboxylic acids such as acetic acid and trifluoroacetic acid, and halogenated hydrocarbons such as dichloromethane and chloroform.

The oxidation is normally successfully carried out at from 0° C. to the boiling point of the reaction mixture.

The oxidant is normally employed in at least equimolar amounts based on the starting compound. However, a large excess of oxidant has generally proved especially advantageous.

Some intermediates of the formula II are already known from the catalog: Intermediates 4, 1990; Supplement to Catalog 4, RDfile Product Listing, January 1994, MAYBRIDGE CHEMICAL COMPANY LTD., Trevillett, Tintagel, Cornwall PL34 0HW, United Kingdom [No. II.1–II.5]; Ann. Chim. (Rome) 62, (1972), 249–256 [No. II.7]; Tetrahedron 39, (1983), 4153 [No. II.8 and II.9]; Pharmazie 47, (1992), 86–91 [No. II.10 and II.11]; U.S. 670901 [No. II.12]; J. Heterocycl. Chem. 24, (1987), 85–89 [No. II.14]; Bull. Chim. Farm. 114, (1975), 590 [No. II.15]; DD 27 11 11 [No. II.16 to II.18].

Other novel compounds are those of the formula II

 (II)

and their salts and N-oxides, where the variables have the following meanings:

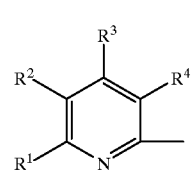 (A1)

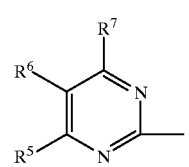 (A2)

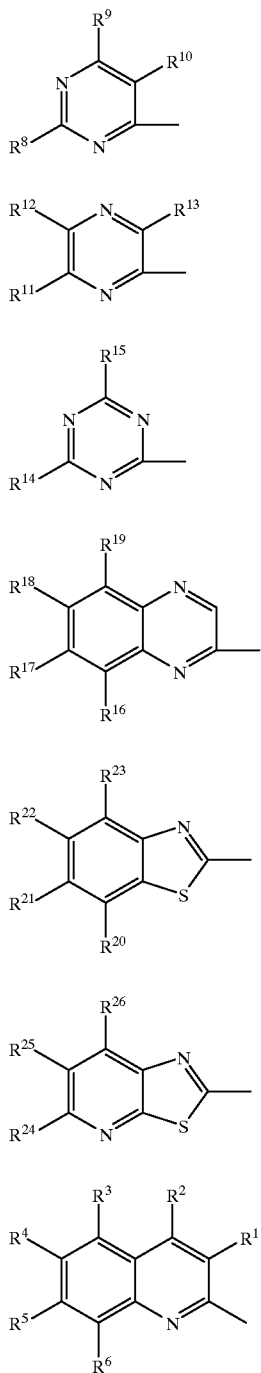

(A3)

(A4)

(A5)

(A6)

(A7)

(A8)

(A9)

where the groups

R$^1$ to R$^{26}$ independently of one another are: hydrogen, cyano, nitro, halogen, aminocarbonyl, methylsulfonyl, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkoxy-C$_1$–C$_4$-alkyl, (C$_1$–C$_4$-alkoxy)carbonyl, aryl, aryloxy or hetaryl, it being possible for the aryl and hetaryl rings to be unsubstituted or to have attached to them one to three groups, in each case selected from amongst: cyano, nitro, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkoxy-C$_1$–C$_4$-alkyl, (C$_1$–C$_4$-alkoxy)carbonyl and C$_1$–C$_4$-acyl;

m is 0, 1 or 2;

Alk is 1,2-ethylidene or 1,3-propylidene, it being possible for the hydrogen atoms of these chains to be replaced independently of one another by one of the following groups:

C$_1$–C$_8$-alkyl, C$_1$–C$_8$-haloalkyl, C$_2$–C$_8$-alkenyl, C$_2$–C$_8$-haloalkenyl or C$_2$–C$_8$-alkynyl, it being possible for each of these 5 radicals additionally to have attached to them one to three groups, in each case selected from amongst: cyano, C$_1$–C$_4$-alkoxy, C$_1$–C$_4$-haloalkoxy, C$_1$–C$_4$-alkylthio, (C$_1$–C$_4$-alkoxy)carbonyl, C$_3$–C$_7$-cycloalkyl and C$_5$–C$_7$-cycloalkenyl;

C$_3$–C$_7$-cycloalkyl or C$_5$–C$_7$-cycloalkenyl, it being possible for these radicals to be partially or fully halogenated or to have attached to them one to three groups, in each case selected from amongst: cyano, halogen, C$_1$–C$_4$-alkyl, C$_1$–C$_4$-haloalkyl and C$_1$–C$_4$-alkoxy;

X is oxygen, sulfur or —N(R$^a$)—, where R$^a$ is hydrogen, C$_1$–C$_8$-alkyl or C$_3$–C$_7$-cycloalkyl;

and their salts and N-oxides, with the exception of those compounds where A is A1'

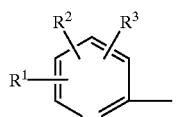

(A1')

where a) R$^1$, R$^2$ and R$^3$ simultaneously are hydrogen, and b) the compounds II.1 to II.18 below:

| No. | R$^1$ | R$^2$ | R$^3$ | m | Alk | X |
|---|---|---|---|---|---|---|
| II.1 | 5-Cl | H | H | 0 | 1,2-ethylidene | —O— |
| II.2 | 6-OCH$_3$ | H | H | 0 | 1,2-ethylidene | —O— |
| II.3 | 5-CF$_3$ | H | H | 0 | 1,2-ethylidene | —O— |
| II.4 | 5-CF$_3$ | H | H | 2 | 1,2-ethylidene | —O— |
| II.5 | 5-CF$_3$ | H | H | 0 | 1,2-ethylidene | —NH— |
| II.6 | 5-NO$_2$ | H | H | 0 | 1,2-ethylidene | —O— |

-continued

| No. | R¹ | R² | R³ | m | Alk | X |
|---|---|---|---|---|---|---|
| II.7 | H | H | 3-NO₂ | 0 | 1,2-ethylidene | —O— |
| II.8 | H | H | 3-OCH₃ | 0 | 1,2-ethylidene | —O— |
| II.9 | H | H | 3-CN | 0 | 1,2-ethylidene | —O— |
| II.10 | 5-Cl | H | H | 0 | 1,2-ethylidene | —NH— |
| II.11 | 6-Cl | H | H | 0 | 1,2-ethylidene | —NH— |
| II.12 | 6-Br | H | H | 0 | 1,2-ethylidene | —NH— |
| II.13 | 6-CH₃ | H | H | 0 | 1,2-ethylidene | —NH— |
| II.14 | H | H | 3-CN | 0 | 1,2-ethylidene | —NH— |
| II.15 | 6-OCH₃ | 5-NO₂ | H | 0 | 1,2-ethylidene | —NH— |
| II.16 | 6-CH₃ | 4-pyridin-4-yl | 3-CN | 0 | 1,2-ethylidene | —O— |
| II.17 | 6-CH₃ | 4-pyridin-3-yl | 3-CN | 0 | 1,2-ethylidene | —O— |
| II.18 | 6-CH₃ | 4-(4-bromophenyl) | 3-CN | 0 | 1,2-ethylidene | —O— |

The intermediates II can be prepared in a manner known per se, for example by one of the following processes:

1. Reaction of a 2-chloropyridine of the formula II with an ethylthio or propylthio compound of the formula IV:

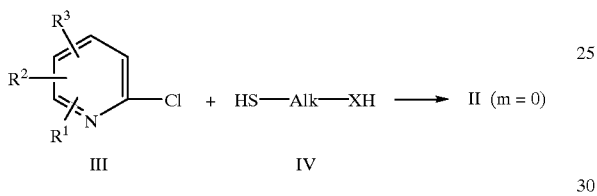

Examples of suitable solvents for this reaction are aprotic solvents such as dimethylformamide.

The process is preferably carried out in the presence of a base, examples of suitable bases being alcoholates such as sodium methanolate or nitrogen bases such as pyridine.

The reaction temperature is generally at from (−10) to 100, in particular 0 to 40, °C.

The starting materials are expediently employed in approximately stoichiometric amounts, but an excess of one or the other component may be advantageous with a view to the process control or as complete a reaction of III or IV as possible.

Reaction of 2-chloropyridines III with compounds M⊕ ⊖O—SO—Alk—XH in a manner known per se (cf. U.S. Pat. No. 5,605,432):

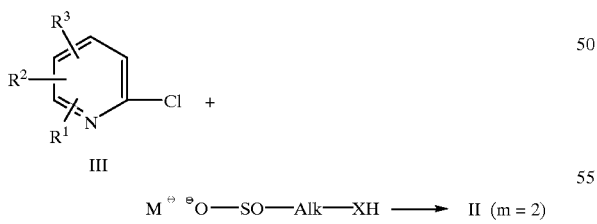

M⊕ is an alkali metal ion, in particular sodium.

3. Reaction of a pyrid-2-ylsulfonylmethane V with unsubstituted or substituted alkyl-, haloalkyl-, alkenyl-, haloalkenyl-, alkynyl-, haloalkynyl-, cycloalkyl-, cycloalkenyl-, aryl- or heteroarylcarbonyl in the presence of a base {cf., for example, Bull. Soc. Chim. Fr; 130, (1993), 341}:

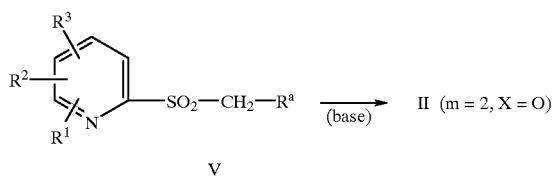

$R^a$ is hydrogen or one of the substituents on Alk.

Solvents which have proved particularly useful are ethers such as tetrahydrofuran. A particularly suitable base is butyllithium. The reaction temperature is normally at from (−78) to 40° C.

Preferably, all reactants are employed in approximately stoichiometric amounts, but an excess of one or the other component of up to approximately 10 mol % may be advantageous.

4. Reaction of a 2-mercaptopyridine VI with an epoxide or oxetane VII (cf., for example, Bull. Soc. Shim. Fr; 130, pages 336–357, in particular p. 343 (1993):

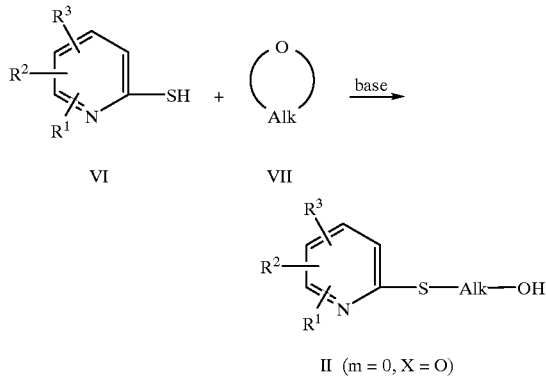

What has been said under 4. regarding solvent, base and ratios also applies here. The reaction temperature is normally at from (−78) to 30° C.

Unless otherwise indicated, all processes described above are expediently carried out under atmospheric pressure or under the inherent pressure of the reaction mixture in question.

The reaction mixtures are generally worked up in a manner known per se, eg. by removing the solvent, partitioning the residue in a mixture of water and a suitable organic solvent and working up the organic phase to give the product.

Depending on the substitution pattern, the compounds of the formula I may contain one or more chiral centers, in which case they exist in the form of enantiomer or diastereomer mixtures. The invention relates both to the pure enantiomers or diastereomers and also to their mixtures.

Part of the invention are also the salts of the acid-resistant compounds I which contain basic centers, especially basic nitrogen atoms, in particular with mineral acids such as sulfuric acid and phosphoric acid or Lewis acids such as zinc chloride. The type of salt is normally of no importance. Preferred within the scope of the invention are those salts which do not harm the plants, areas, materials or spaces to be kept free from harmful fungi or animal pests and which do not adversely affect the activity of the compounds I. Such agronomically useful salts are especially important.

The salts of the compounds I are accessible in a manner known per se, especially by reacting the corresponding compounds I with the abovementioned acids in water or in an inert organic solvent at from −80 to 120° C., preferably 0 to 60° C.

The organic moieties which have been mentioned in the definition of the substituents $R^1$ to $R^{26}$ or as radicals on aryl rings or heteroaromatics are collective terms for individual enumerations of the individual group members, as is the meaning of halogen. All carbon chains, ie. all alkyl, haloalkyl, alkoxy, haloalkoxy, alkylthio, alkenyl, haloalkenyl, alkynyl and haloalkynyl moieties, can be straight-chain or branched. Halogenated substituents preferably have attached to them one to five identical or different halogen atoms. Halogen is in each case fluorine, chlorine, bromine or iodine.

Other examples of meanings are:

$C_1$–$C_4$-alkyl and the alkyl moiety of $C_1$–$C_4$-alkoxy-$C_1$–$C_4$-alkyl is: methyl, ethyl, n-propyl, 1-methylethyl, n-butyl, 1-methylpropyl, 2-methylpropyl and 1,1-dimethylethyl;

$C_1$–$C_8$-alkyl is: $C_1$–$C_4$-alkyl as mentioned above, and also for example n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl;

$C_1$–$C_6$-alkyl is preferred;

$C_1$–$C_4$-haloalkyl is: a $C_1$–$C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy and the alkoxy moiety of $C_1$–$C_4$-alkoxy-$C_1$–$C_4$-alkyl are: methoxy, ethoxy, n-propoxy, 1-methylethoxy, n-butoxy, 1-methylpropoxy, 2-methylpropoxy and 1,1-dimethylethoxy;

$C_1$–$C_4$-acyl is: methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl;

($C_1$–$C_4$-alkoxy)carbonyl is: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl;

$C_3$–$C_7$-cycloalkyl is: cyclopropyl, cyclobutyl, cyclopentyl, cyclohexyl and cycloheptyl;

$C_5$–$C_7$-cycloalkenyl is: cyclopent-1-enyl, cyclopent-2-enyl, cyclopent-3-enyl, cyclohex-1-enyl, cyclohex-2-enyl, cyclohex-3-enyl, cyclohept-1-enyl and cyclohept-2-enyl;

$C_2$–$C_4$-alkenyl is: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl or 2-methylprop-2-en-1-yl ;

$C_2$–$C_8$-alkenyl is: eg. ethenyl, prop-1-en-1-yl, prop-2-en-1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl, 1-ethyl-2-methylprop-2-en-1-yl, n-hept-1-en-1-yl, n-hept-2-en-1-yl, n-hept-3-en-1-yl, n-hept-4-en-1-yl, n-hept-5-en-1-yl, n-hept-6-en-1-yl, 1,4-dimethylpent-2-en-1-yl, 1-(1-methylethyl)but-2-en-1-yl, n-oct-1-en-1-yl, n-oct-2-en-1-yl, n-oct-3-en-1-yl, n-oct-4-en-1-yl, n-oct-5-en-1-yl, n-oct-6-en-1-yl, n-oct-7-en-1-yl and 1-butylbut-2-en-1-yl;

$C_2$–$C_6$-alkenyl is preferred;

$C_2$–$C_8$-haloalkenyl is: $C_2$–$C_8$-alkenyl as mentioned above which is partially or fully substituted by fluorine, chlorine, bromine and/or iodine, eg. 2-chloroallyl, 3-chloroallyl and 3,3-dichloroallyl;

$C_2$–$C_6$-haloalkenyl is preferred;

$C_2$–$C_8$-alkynyl is: eg. ethynyl, prop-1-yn-1-yl, prop-2-yn-1yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn- 4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl is preferred;

aryl-$C_1$–$C_4$-alkyl is: arylmethyl, 1-arylethyl, 2-arylethyl, 1-arylprop-1-yl, 2-arylprop-1-yl, 3-arylprop-1-yl, 1-arylbut-1-yl, 2-arylbut-1-yl, 3-arylbut-1-yl, 4-arylbut-1-yl, 1-arylbut-2-yl, 2-arylbut-2-yl, 3-arylbut-2-yl, 3-arylbut-2-yl, 4-arylbut-2-yl, 1-(arylmethyl)eth-1-yl, 1-(arylmethyl)-1-(methyl)eth-1-yl and 1-(arylmethyl)prop-1-yl;

benzyl and 2-arylethyl are preferred.

Aryl is preferably to be understood as meaning phenyl or a polycyclic aromatic such as naphth-1-yl and naphth-2-yl.

Hetaryl is, in particular, a 5- or 6-membered heteroaromatic having one to three hetero atoms selected from the group consisting of two oxygen atoms, two sulfur atoms and 3 nitrogen atoms. Examples are furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, and furthermore 2-pyrazinyl, 1,3,5-triazin-2-yl and 1,2,4-triazin-3-yl.

With a view to the use of the compounds I for controlling harmful fungi, two of the respective groups $R^1$ to $R^{26}$ in the radicals A are preferably hydrogen.

With a view to the use of the compounds of the formula I, in which A is one of the radicals A1, A3, A7 or A8, for controlling harmful fungi, the variables preferably have the following meanings, in each case alone or in combination:

$R^1$, $R^2$, $R^3$, $R^4$, $R^8$, $R^9$, $R^{10}$, $R^{20}$, $R^{21}$, $R^{22}$, $R^{23}$, $R^{24}$, $R^{25}$ and $R^{26}$ independently of one another are hydrogen, cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or aryl, especially preferably hydrogen, cyano, nitro, halogen, in particular fluorine, chlorine and bromine, $C_1$–$C_3$-alkyl, in particular methyl, ethyl and isopropyl, $C_1$- or $C_2$-haloalkyl, in particular chloromethyl, dichloromethyl, fluoromethyl, difluoromethyl, trifluoromethyl, trichloromethyl and pentafluoroethyl, or $C_1$- or $C_2$-alkoxy, in particular methoxy and ethoxy;

especially preferably, at least two of the relevant groups of $R^1$ to $R^{26}$ hydrogen;

m is two;

Alk is 1,2-ethylidene or 1,3-propylidene, it being possible for each hydrogen atom of these chains to be replaced by one of the following groups: $C_1$–$C_4$-alkyl, $C_1$–$C_4$-haloalkyl or $C_3$–$C_6$-cycloalkyl;

especially preferably 1,2-ethylidene which can have attached to it one to four of the following groups: $C_1$–$C_4$-alkyl, in particular methyl, ethyl, isopropyl and n-butyl, or $C_3$–$C_6$-cycloalkyl, in particular cyclopropyl, cyclopentyl and cyclohexyl;

very especially preferably unsubstituted ethylidene ($CH_2$—$CH_2$);

X is oxygen, sulfur, —NH— or —N($C_1$–$C_4$-alkyl)-, especially preferably oxygen;

Q is aryl or hetaryl, it being possible for these rings to be unsubstituted or to have attached to them one to three groups, in each case selected from amongst: halogen, in particular fluorine, chlorine or bromine, $C_1$–$C_4$-alkyl, $C_1$–$C_4$-haloalkyl, in particular $C_1$–$C_2$-haloalkyl such as trifluoromethyl, trichloromethyl or pentafluoroethyl, $C_1$–$C_4$-alkoxy, in particular methoxy or ethoxy, trifluoromethoxy, $C_1$–$C_4$-alkylthio, phenyl and phenoxy;

$C_3$–$C_6$-cycloalkyl which can be unsubstituted or can have attached to it one to three groups, in each case selected from amongst: cyano, halogen, $C_1$–$C_4$-alkyl, $C_1$–$C_4$-haloalkyl, $C_1$–$C_4$-alkoxy, $C_1$–$C_4$-alkylthio, phenyl and phenoxy;

arylmethyl or arylethyl, it being possible for the aryl ring to be unsubstituted or to have attached to it one to three groups, in each case selected from the group consisting of cyano, halogen, $C_1$–$C_4$-alkyl, $C_1$–$C_4$-haloalkyl, $C_1$–$C_4$-alkoxy, $C_1$–$C_4$-alkylthio, phenyl and phenoxy.

Very especially preferred amongst the compounds I in which A=A1 are the compounds which are listed in Tables A to C below:

I. Ala

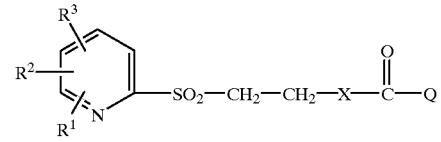

TABLE A

| No. | $R^1$ | $R^2$ | $R^3$ | X | Q |
|---|---|---|---|---|---|
| I.A1a.001 | H | H | H | —O— | phenyl |
| I.A1a.002 | H | H | H | —O— | 2-chlorophenyl |
| I.A1a.003 | H | H | H | —O— | 3-chlorophenyl |
| I.A1a.004 | H | H | H | —O— | 4-chlorophenyl |
| I.A1a.005 | H | H | H | —O— | 2,3-dichlorophenyl |
| I.A1a.006 | H | H | H | —O— | 2,5-dichlorophenyl |
| I.A1a.007 | H | H | H | —O— | 3,5-dichlorophenyl |
| I.A1a.008 | H | H | H | —O— | 2,4-dichlorophenyl |
| I.A1a.009 | H | H | H | —O— | 2,6-dichlorophenyl |
| I.A1a.010 | H | H | H | —O— | 2-fluorophenyl |
| I.A1a.011 | H | H | H | —O— | 3-fluorophenyl |
| I.A1a.012 | H | H | H | —O— | 4-fluorophenyl |
| I.A1a.013 | H | H | H | —O— | 2,3-difluorophenyl |
| I.A1a.014 | H | H | H | —O— | 3,5-difluorophenyl |
| I.A1a.015 | H | H | H | —O— | 2-methylphenyl |
| I.A1a.016 | H | H | H | —O— | 3-methylphenyl |
| I.A1a.017 | H | H | H | —O— | 4-methylphenyl |
| I.A1a.018 | H | H | H | —O— | 2,3-dimethylphenyl |
| I.A1a.019 | H | H | H | —O— | 3,5-dimethylphenyl |
| I.A1a.020 | H | H | H | —O— | 2-methoxyphenyl |
| I.A1a.021 | H | H | H | —O— | 3-methoxyphenyl |
| I.A1a.022 | H | H | H | —O— | 4-methoxyphenyl |
| I.A1a.023 | H | H | H | —O— | 2,3-dimethoxyphenyl |
| I.A1a.024 | H | H | H | —O— | 3,5-dimethoxyphenyl |
| I.A1a.025 | H | H | H | —O— | 2,5-dimethoxyphenyl |
| I.A1a.026 | H | H | H | —O— | 3-isopropylphenyl |
| I.A1a.027 | H | H | H | —O— | 3-(n-butyl)phenyl |
| I.A1a.028 | H | H | H | —O— | 3-phenylphenyl |
| I.A1a.029 | H | H | H | —O— | 3-trifluoromethylphenyl |
| I.A1a.030 | H | H | H | —O— | 3-nitrophenyl |
| I.A1a.031 | H | H | H | —O— | 3-bromophenyl |
| I.A1a.032 | H | H | H | —O— | 2,3-dichlorophenyl |

TABLE A-continued

| No. | R¹ | R² | R³ | X | Q |
|---|---|---|---|---|---|
| I.A1a.033 | H | H | H | —O— | 3-cyanophenyl |
| I.A1a.034 | H | H | H | —O— | 3-phenoxyphenyl |
| I.A1a.035 | H | H | H | —O— | 3-(trichloromethyl)phenyl |
| I.A1a.036 | H | H | H | —O— | 3-ethylphenyl |
| I.A1a.037 | H | H | H | —O— | 3-(trichloromethoxy)phenyl |
| I.A1a.038 | H | H | H | —O— | 3-(chlorodifluoromethyl)phenyl |
| I.A1a.039 | H | H | H | —O— | 3-(methylcarbonyl)phenyl |
| I.A1a.040 | H | H | H | —O— | 3-(methylsulfonyl)phenyl |
| I.A1a.041 | H | H | H | —O— | 3-(chloromethyl)phenyl |
| I.A1a.042 | H | H | H | —O— | 5-chloro-2-methoxyphenyl |
| I.A1a.043 | H | H | H | —O— | 3-(benzyloxy)phenyl |
| I.A1a.044 | H | H | 3-Cl | —O— | phenyl |
| I.A1a.045 | H | H | 3-Cl | —O— | 2-chlorophenyl |
| I.A1a.046 | H | H | 3-Cl | —O— | 3-chlorophenyl |
| I.A1a.047 | H | H | 3-Cl | —O— | 4-chlorophenyl |
| I.A1a.048 | H | H | 3-Cl | —O— | 2,3-dichlorophenyl |
| I.A1a.049 | H | H | 3-Cl | —O— | 2,5-dichlorophenyl |
| I.A1a.050 | H | H | 3-Cl | —O— | 3,5-dichlorophenyl |
| I.A1a.051 | H | H | 3-Cl | —O— | 2,4-dichlorophenyl |
| I.A1a.052 | H | H | 3-Cl | —O— | 2,6-dichlorophenyl |
| I.A1a.053 | H | H | 3-Cl | —O— | 2-fluorophenyl |
| I.A1a.054 | H | H | 3-Cl | —O— | 3-fluorophenyl |
| I.A1a.055 | H | H | 3-Cl | —O— | 4-fluorophenyl |
| I.A1a.056 | H | H | 3-Cl | —O— | 2,3-difluorophenyl |
| I.A1a.057 | H | H | 3-Cl | —O— | 3,5-difluorophenyl |
| I.A1a.058 | H | H | 3-Cl | —O— | 2-methylphenyl |
| I.A1a.059 | H | H | 3-Cl | —O— | 3-methylphenyl |
| I.A1a.060 | H | H | 3-Cl | —O— | 4-methylphenyl |
| I.A1a.061 | H | H | 3-Cl | —O— | 2,3-dimethylphenyl |
| I.A1a.062 | H | H | 3-Cl | —O— | 3,5-dimethylphenyl |
| I.A1a.063 | H | H | 3-Cl | —O— | 2-methoxyphenyl |
| I.A1a.064 | H | H | 3-Cl | —O— | 3-methoxyphenyl |
| I.A1a.065 | H | H | 3-Cl | —O— | 4-methoxyphenyl |
| I.A1a.066 | H | H | 3-Cl | —O— | 2,3-dimethoxyphenyl |
| I.A1a.067 | H | H | 3-Cl | —O— | 3,5-dimethoxyphenyl |
| I.A1a.068 | H | H | 3-Cl | —O— | 2,5-dimethoxyphenyl |
| I.A1a.069 | H | H | 3-Cl | —O— | 3-isopropylphenyl |
| I.A1a.070 | H | H | 3-Cl | —O— | 3-(n-butyl)phenyl |
| I.A1a.071 | H | H | 3-Cl | —O— | 3-phenylphenyl |
| I.A1a.072 | H | H | 3-Cl | —O— | 3-(trifluoromethyl)phenyl |
| I.A1a.073 | H | H | 3-Cl | —O— | 3-nitrophenyl |
| I.A1a.074 | H | H | 3-Cl | —O— | 3-bromophenyl |
| I.A1a.075 | H | H | 3-Cl | —O— | 2,3-dichlorophenyl |
| I.A1a.076 | H | H | 3-Cl | —O— | 3-cyanophenyl |
| I.A1a.077 | H | H | 3-Cl | —O— | 3-phenyloxyphenyl |
| I.A1a.078 | H | H | 3-Cl | —O— | 3-trichloromethylphenyl |
| I.A1a.079 | H | H | 3-Cl | —O— | 3-ethylphenyl |
| I.A1a.080 | H | H | 3-Cl | —O— | 3-(trichloromethoxy)phenyl |
| I.A1a.081 | H | H | 3-Cl | —O— | 3-(chlorodifluoromethyl)phenyl |
| I.A1a.082 | H | H | 3-Cl | —O— | 3-(methylcarbonyl)phenyl |
| I.A1a.083 | H | H | 3-Cl | —O— | 3-(methylsulfonyl)phenyl |
| I.A1a.084 | H | H | 3-Cl | —O— | 3-(chloromethyl)phenyl |
| I.A1a.085 | H | H | 3-Cl | —O— | 5-chloro-2-methoxyphenyl |
| I.A1a.086 | H | H | 3-Cl | —O— | 3-benzyloxyphenyl |
| I.A1a.087 | H | H | 3-CF₃ | —O— | phenyl |
| I.A1a.088 | H | H | 3-CF₃ | —O— | 2-chlorophenyl |
| I.A1a.089 | H | H | 3-CF₃ | —O— | 3-chlorophenyl |
| I.A1a.090 | H | H | 3-CF₃ | —O— | 4-chlorophenyl |
| I.A1a.091 | H | H | 3-CF₃ | —O— | 2,3-dichlorophenyl |
| I.A1a.092 | H | H | 3-CF₃ | —O— | 2,5-dichlorophenyl |
| I.A1a.093 | H | H | 3-CF₃ | —O— | 3,5-dichlorophenyl |
| I.A1a.094 | H | H | 3-CF₃ | —O— | 2,4-dichlorophenyl |
| I.A1a.095 | H | H | 3-CF₃ | —O— | 2,6-dichlorophenyl |
| I.A1a.096 | H | H | 3-CF₃ | —O— | 2-fluorophenyl |
| I.A1a.097 | H | H | 3-CF₃ | —O— | 3-fluorophenyl |
| I.A1a.098 | H | H | 3-CF₃ | —O— | 4-fluorophenyl |
| I.A1a.099 | H | H | 3-CF₃ | —O— | 2,3-difluorophenyl |
| I.A1a.100 | H | H | 3-CF₃ | —O— | 3,5-difluorophenyl |
| I.A1a.101 | H | H | 3-CF₃ | —O— | 2-methylphenyl |
| I.A1a.102 | H | H | 3-CF₃ | —O— | 3-methylphenyl |
| I.A1a.103 | H | H | 3-CF₃ | —O— | 4-methylphenyl |
| I.A1a.104 | H | H | 3-CF₃ | —O— | 2,3-dimethylphenyl |
| I.A1a.105 | H | H | 3-CF₃ | —O— | 3,5-dimethylphenyl |
| I.A1a.106 | H | H | 3-CF₃ | —O— | 2-methoxyphenyl |
| I.A1a.107 | H | H | 3-CF₃ | —O— | 3-methoxyphenyl |
| I.A1a.108 | H | H | 3-CF₃ | —O— | 4-methoxyphenyl |
| I.A1a.109 | H | H | 3-CF₃ | —O— | 2,3-dimethoxyphenyl |
| I.A1a.110 | H | H | 3-CF₃ | —O— | 3,5-dimethoxyphenyl |
| I.A1a.111 | H | H | 3-CF₃ | —O— | 2,5-dimethoxyphenyl |
| I.A1a.112 | H | H | 3-CF₃ | —O— | 3-isopropylphenyl |
| I.A1a.113 | H | H | 3-CF₃ | —O— | 3-(n-butyl)phenyl |
| I.A1a.114 | H | H | 3-CF₃ | —O— | 3-phenylphenyl |
| I.A1a.115 | H | H | 3-CF₃ | —O— | 3-(trifluoromethyl)phenyl |
| I.A1a.116 | H | H | 3-CF₃ | —O— | 3-nitrophenyl |
| I.A1a.117 | H | H | 3-CF₃ | —O— | 3-bromophenyl |
| I.A1a.118 | H | H | 3-CF₃ | —O— | 2,3-dichlorophenyl |
| I.A1a.119 | H | H | 3-CF₃ | —O— | 3-cyanophenyl |
| I.A1a.120 | H | H | 3-CF₃ | —O— | 3-phenoxyphenyl |
| I.A1a.121 | H | H | 3-CF₃ | —O— | 3-(trichloromethyl)phenyl |
| I.A1a.122 | H | H | 3-CF₃ | —O— | 3-ethylphenyl |
| I.A1a.123 | H | H | 3-CF₃ | —O— | 3-(trichloromethoxy)phenyl |
| I.A1a.124 | H | H | 3-CF₃ | —O— | 3-(chlorodifluoromethyl)phenyl |
| I.A1a.125 | H | H | 3-CF₃ | —O— | 3-(methylcarbonyl)phenyl |
| I.A1a.126 | H | H | 3-CF₃ | —O— | 3-(methylsulfonyl)phenyl |
| I.A1a.127 | H | H | 3-CF₃ | —O— | 3-(chloromethyl)phenyl |
| I.A1a.128 | H | H | 3-CF₃ | —O— | 5-chloro-2-methoxyphenyl |
| I.A1a.129 | H | H | 3-CF₃ | —O— | 3-(benzyloxy)phenyl |
| I.A1a.130 | H | H | 3-CN | —O— | phenyl |
| I.A1a.131 | H | H | 3-CN | —O— | 2-chlorophenyl |
| I.A1a.132 | H | H | 3-CN | —O— | 3-chlorophenyl |
| I.A1a.133 | H | H | 3-CN | —O— | 4-chlorophenyl |
| I.A1a.134 | H | H | 3-CN | —O— | 2,3-dichlorophenyl |
| I.A1a.135 | H | H | 3-CN | —O— | 2,5-dichlorophenyl |
| I.A1a.136 | H | H | 3-CN | —O— | 3,5-dichlorophenyl |
| I.A1a.137 | H | H | 3-CN | —O— | 2,4-dichlorophenyl |
| I.A1a.138 | H | H | 3-CN | —O— | 2,6-dichlorophenyl |
| I.A1a.139 | H | H | 3-CN | —O— | 2-fluorophenyl |
| I.A1a.140 | H | H | 3-CN | —O— | 3-fluorophenyl |
| I.A1a.141 | H | H | 3-CN | —O— | 4-fluorophenyl |
| I.A1a.142 | H | H | 3-CN | —O— | 2,3-difluorophenyl |
| I.A1a.143 | H | H | 3-CN | —O— | 3,5-difluorophenyl |
| I.A1a.144 | H | H | 3-CN | —O— | 2-methylphenyl |
| I.A1a.145 | H | H | 3-CN | —O— | 3-methylphenyl |
| I.A1a.146 | H | H | 3-CN | —O— | 4-methylphenyl |
| I.A1a.147 | H | H | 3-CN | —O— | 2,3-dimethylphenyl |
| I.A1a.148 | H | H | 3-CN | —O— | 3,5-dimethylphenyl |
| I.A1a.149 | H | H | 3-CN | —O— | 2-methoxyphenyl |
| I.A1a.150 | H | H | 3-CN | —O— | 3-methoxyphenyl |
| I.A1a.151 | H | H | 3-CN | —O— | 4-methoxyphenyl |
| I.A1a.152 | H | H | 3-CN | —O— | 2,3-dimethoxyphenyl |
| I.A1a.153 | H | H | 3-CN | —O— | 3,5-dimethoxyphenyl |
| I.A1a.154 | H | H | 3-CN | —O— | 2,5-dimethoxyphenyl |
| I.A1a.155 | H | H | 3-CN | —O— | 3-isopropylphenyl |
| I.A1a.156 | H | H | 3-CN | —O— | 3-(n-butyl)phenyl |
| I.A1a.157 | H | H | 3-CN | —O— | 3-phenylphenyl |
| I.A1a.158 | H | H | 3-CN | —O— | 3-(trifluoromethyl)phenyl |
| I.A1a.159 | H | H | 3-CN | —O— | 3-nitrophenyl |
| I.A1a.160 | H | H | 3-CN | —O— | 3-bromophenyl |
| I.A1a.161 | H | H | 3-CN | —O— | 2,3-dichlorophenyl |
| I.A1a.162 | H | H | 3-CN | —O— | 3-cyanophenyl |

TABLE A-continued

| No. | R¹ | R² | R³ | X | Q |
|---|---|---|---|---|---|
| I.A1a.163 | H | H | 3-CN | —O— | 3-phenoxyphenyl |
| I.A1a.164 | H | H | 3-CN | —O— | 3-(trichloromethyl)phenyl |
| I.A1a.165 | H | H | 3-CN | —O— | 3-ethylphenyl |
| I.A1a.166 | H | H | 3-CN | —O— | 3-trichloromethoxyphenyl |
| I.A1a.167 | H | H | 3-CN | —O— | 3-(chlorodifluoro)phenyl |
| I.A1a.168 | H | H | 3-CN | —O— | 3-(methylcarbonyl)phenyl |
| I.A1a.169 | H | H | 3-CN | —O— | 3-(methylsulfonyl)phenyl |
| I.A1a.170 | H | H | 3-CN | —O— | 3-(chloromethyl)phenyl |
| I.A1a.171 | H | H | 3-CN | —O— | 5-chloro-2-methoxyphenyl |
| I.A1a.172 | H | H | 3-CN | —O— | 3-benzyloxyphenyl |
| I.A1a.173 | 5-Cl | H | H | —O— | phenyl |
| I.A1a.174 | 5-Cl | H | H | —O— | 2-chloro |
| I.A1a.175 | 5-Cl | H | H | —O— | 3-chloro |
| I.A1a.176 | 5-Cl | H | H | —O— | 4-chloro |
| I.A1a.177 | 5-Cl | H | H | —O— | 2,3-dichlorophenyl |
| I.A1a.178 | 5-Cl | H | H | —O— | 2,5-dichlorophenyl |
| I.A1a.179 | 5-Cl | H | H | —O— | 3,5-dichlorophenyl |
| I.A1a.180 | 5-Cl | H | H | —O— | 2,4-dichlorophenyl |
| I.A1a.181 | 5-Cl | H | H | —O— | 2,6-dichlorophenyl |
| I.A1a.182 | 5-Cl | H | H | —O— | 2-fluorophenyl |
| I.A1a.183 | 5-Cl | H | H | —O— | 3-fluorophenyl |
| I.A1a.184 | 5-Cl | H | H | —O— | 4-fluorophenyl |
| I.A1a.185 | 5-Cl | H | H | —O— | 2,3-difluorophenyl |
| I.A1a.186 | 5-Cl | H | H | —O— | 3,5-difluorophenyl |
| I.A1a.187 | 5-Cl | H | H | —O— | 2-methylphenyl |
| I.A1a.188 | 5-Cl | H | H | —O— | 3-methylphenyl |
| I.A1a.189 | 5-Cl | H | H | —O— | 4-methylphenyl |
| I.A1a.190 | 5-Cl | H | H | —O— | 2,3-dimethylphenyl |
| I.A1a.191 | 5-Cl | H | H | —O— | 3,5-dimethylphenyl |
| I.A1a.192 | 5-Cl | H | H | —O— | 2-methoxyphenyl |
| I.A1a.193 | 5-Cl | H | H | —O— | 3-methoxyphenyl |
| I.A1a.194 | 5-Cl | H | H | —O— | 4-methoxyphenyl |
| I.A1a.195 | 5-Cl | H | H | —O— | 2,3-dimethoxyphenyl |
| I.A1a.196 | 5-Cl | H | H | —O— | 3,5-dimethoxyphenyl |
| I.A1a.197 | 5-Cl | H | H | —O— | 2,5-dimethoxyphenyl |
| I.A1a.198 | 5-Cl | H | H | —O— | 3-isopropylphenyl |
| I.A1a.199 | 5-Cl | H | H | —O— | 3-(n-butyl)phenyl |
| I.A1a.200 | 5-Cl | H | H | —O— | 3-(phenyl)phenyl |
| I.A1a.201 | 5-Cl | H | H | —O— | 3-(trifluoromethyl)phenyl |
| I.A1a.202 | 5-Cl | H | H | —O— | 3-nitrophenyl |
| I.A1a.203 | 5-Cl | H | H | —O— | 3-bromophenyl |
| I.A1a.204 | 5-Cl | H | H | —O— | 2,3-dichlorophenyl |
| I.A1a.205 | 5-Cl | H | H | —O— | 3-cyanophenyl |
| I.A1a.206 | 5-Cl | H | H | —O— | 3-(phenoxy)phenyl |
| I.A1a.207 | 5-Cl | H | H | —O— | 3-(trichloromethyl)phenyl |
| I.A1a.208 | 5-Cl | H | H | —O— | 3-ethylphenyl |
| I.A1a.209 | 5-Cl | H | H | —O— | 3-(trichloromethoxy)phenyl |
| I.A1a.210 | 5-Cl | H | H | —O— | 3-(chlorodifluoromethyl)phenyl |
| I.A1a.211 | 5-Cl | H | H | —O— | 3-(methylcarbonyl)phenyl |
| I.A1a.212 | 5-Cl | H | H | —O— | 3-(methylsulfonyl)phenyl |
| I.A1a.213 | 5-Cl | H | H | —O— | 3-(chloromethyl)phenyl |
| I.A1a.214 | 5-Cl | H | H | —O— | 5-chloro-2-methoxyphenyl |
| I.A1a.215 | 5-Cl | H | H | —O— | 3-(benzyloxy)phenyl |
| I.A1a.216 | 5-CF₃ | H | H | —O— | phenyl |
| I.A1a.217 | 5-CF₃ | H | H | —O— | 2-chlorophenyl |
| I.A1a.218 | 5-CF₃ | H | H | —O— | 3-chlorophenyl |
| I.A1a.219 | 5-CF₃ | H | H | —O— | 4-chlorophenyl |
| I.A1a.220 | 5-CF₃ | H | H | —O— | 2,3-dichlorophenyl |
| I.A1a.221 | 5-CF₃ | H | H | —O— | 2,5-dichlorophenyl |
| I.A1a.222 | 5-CF₃ | H | H | —O— | 3,5-dichlorophenyl |
| I.A1a.223 | 5-CF₃ | H | H | —O— | 2,4-dichlorophenyl |
| I.A1a.224 | 5-CF₃ | H | H | —O— | 2,6-dichlorophenyl |
| I.A1a.225 | 5-CF₃ | H | H | —O— | 2-fluorophenyl |
| I.A1a.226 | 5-CF₃ | H | H | —O— | 3-fluorophenyl |
| I.A1a.227 | 5-CF₃ | H | H | —O— | 4-fluorophenyl |
| I.A1a.228 | 5-CF₃ | H | H | —O— | 2,3-difluorophenyl |
| I.A1a.229 | 5-CF₃ | H | H | —O— | 3,5-difluorophenyl |
| I.A1a.230 | 5-CF₃ | H | H | —O— | 2-methylphenyl |
| I.A1a.231 | 5-CF₃ | H | H | —O— | 3-methylphenyl |
| I.A1a.232 | 5-CF₃ | H | H | —O— | 4-methylphenyl |
| I.A1a.233 | 5-CF₃ | H | H | —O— | 2,3-dimethylphenyl |
| I.A1a.234 | 5-CF₃ | H | H | —O— | 3,5-dimethylphenyl |
| I.A1a.235 | 5-CF₃ | H | H | —O— | 2-methoxyphenyl |
| I.A1a.236 | 5-CF₃ | H | H | —O— | 3-methoxyphenyl |
| I.A1a.237 | 5-CF₃ | H | H | —O— | 4-methoxyphenyl |
| I.A1a.238 | 5-CF₃ | H | H | —O— | 2,3-dimethoxyphenyl |
| I.A1a.239 | 5-CF₃ | H | H | —O— | 3,5-dimethoxyphenyl |
| I.A1a.240 | 5-CF₃ | H | H | —O— | 2,5-dimethoxyphenyl |
| I.A1a.241 | 5-CF₃ | H | H | —O— | 3-isopropylphenyl |
| I.A1a.242 | 5-CF₃ | H | H | —O— | 3-(n-butyl)phenyl |
| I.A1a.243 | 5-CF₃ | H | H | —O— | 3-phenylphenyl |
| I.A1a.244 | 5-CF₃ | H | H | —O— | 3-(trifluoromethyl)phenyl |
| I.A1a.245 | 5-CF₃ | H | H | —O— | 3-nitrophenyl |
| I.A1a.246 | 5-CF₃ | H | H | —O— | 3-bromophenyl |
| I.A1a.247 | 5-CF₃ | H | H | —O— | 2,3-dichlorophenyl |
| I.A1a.248 | 5-CF₃ | H | H | —O— | 3-cyanophenyl |
| I.A1a.249 | 5-CF₃ | H | H | —O— | 3-(phenoxy)phenyl |
| I.A1a.250 | 5-CF₃ | H | H | —O— | 3-(trichloromethyl)phenyl |
| I.A1a.251 | 5-CF₃ | H | H | —O— | 3-ethylphenyl |
| I.A1a.252 | 5-CF₃ | H | H | —O— | 3-(trichloromethoxy)phenyl |
| I.A1a.253 | 5-CF₃ | H | H | —O— | 3-(chlorodifluoromethyl)phenyl |
| I.A1a.254 | 5-CF₃ | H | H | —O— | 3-(methylcarbonyl)phenyl |
| I.A1a.255 | 5-CF₃ | H | H | —O— | 3-(methylsulfonyl)phenyl |
| I.A1a.256 | 5-CF₃ | H | H | —O— | 3-(chloromethyl)phenyl |
| I.A1a.257 | 5-CF₃ | H | H | —O— | 5-chloro-2-methoxyphenyl |
| I.A1a.258 | 5-CF₃ | H | H | —O— | 3-(benzyloxy)phenyl |
| I.A1a.259 | 5-CN | H | H | —O— | phenyl |
| I.A1a.260 | 5-CN | H | H | —O— | 2-chlorophenyl |
| I.A1a.261 | 5-CN | H | H | —O— | 3-chlorophenyl |
| I.A1a.262 | 5-CN | H | H | —O— | 4-chlorophenyl |
| I.A1a.263 | 5-CN | H | H | —O— | 2,3-dichlorophenyl |
| I.A1a.264 | 5-CN | H | H | —O— | 2,5-dichlorophenyl |
| I.A1a.265 | 5-CN | H | H | —O— | 3,5-dichlorophenyl |
| I.A1a.266 | 5-CN | H | H | —O— | 2,4-dichlorophenyl |
| I.A1a.267 | 5-CN | H | H | —O— | 2,6-dichlorophenyl |
| I.A1a.268 | 5-CN | H | H | —O— | 2-fluorophenyl |
| I.A1a.269 | 5-CN | H | H | —O— | 3-fluorophenyl |
| I.A1a.270 | 5-CN | H | H | —O— | 4-fluorophenyl |
| I.A1a.271 | 5-CN | H | H | —O— | 2,3-difluorophenyl |
| I.A1a.272 | 5-CN | H | H | —O— | 3,5-difluorophenyl |
| I.A1a.273 | 5-CN | H | H | —O— | 2-methylphenyl |
| I.A1a.274 | 5-CN | H | H | —O— | 3-methylphenyl |
| I.A1a.275 | 5-CN | H | H | —O— | 4-methylphenyl |
| I.A1a.276 | 5-CN | H | H | —O— | 2,3-dimethylphenyl |
| I.A1a.277 | 5-CN | H | H | —O— | 3,5-dimethylphenyl |
| I.A1a.278 | 5-CN | H | H | —O— | 2-methoxyphenyl |
| I.A1a.279 | 5-CN | H | H | —O— | 3-methoxyphenyl |
| I.A1a.280 | 5-CN | H | H | —O— | 4-methoxyphenyl |
| I.A1a.281 | 5-CN | H | H | —O— | 2,3-dimethoxyphenyl |
| I.A1a.282 | 5-CN | H | H | —O— | 3,5-dimethoxyphenyl |
| I.A1a.283 | 5-CN | H | H | —O— | 2,5-dimethoxyphenyl |
| I.A1a.284 | 5-CN | H | H | —O— | 3-isopropylphenyl |
| I.A1a.285 | 5-CN | H | H | —O— | 3-(n-butyl)phenyl |
| I.A1a.286 | 5-CN | H | H | —O— | 3-phenylphenyl |
| I.A1a.287 | 5-CN | H | H | —O— | 3-(trifluoromethyl)phenyl |
| I.A1a.288 | 5-CN | H | H | —O— | 3-nitrophenyl |
| I.A1a.289 | 5-CN | H | H | —O— | 3-bromophenyl |
| I.A1a.290 | 5-CN | H | H | —O— | 2,3-dichlorophenyl |
| I.A1a.291 | 5-CN | H | H | —O— | 3-cyanophenyl |
| I.A1a.292 | 5-CN | H | H | —O— | 3-(phenoxy)phenyl |

TABLE A-continued

| No. | R¹ | R² | R³ | X | Q |
|---|---|---|---|---|---|
| I.A1a.293 | 5-CN | H | H | —O— | 3-(trichloromethyl)phenyl |
| I.A1a.294 | 5-CN | H | H | —O— | 3-ethylphenyl |
| I.A1a.295 | 5-CN | H | H | —O— | 3-(trichloromethoxy)phenyl |
| I.A1a.296 | 5-CN | H | H | —O— | 3-(chlorodifluoromethyl)phenyl |
| I.A1a.297 | 5-CN | H | H | —O— | 3-(methylcarbonyl)phenyl |
| I.A1a.298 | 5-CN | H | H | —O— | 3-(methylsulfonyl)phenyl |
| I.A1a.299 | 5-CN | H | H | —O— | 3-(chloromethyl)phenyl |
| I.A1a.300 | 5-CN | H | H | —O— | 5-chloro-2-methoxyphenyl |
| I.A1a.301 | 5-CN | H | H | —O— | 3-(benzyloxy)phenyl |
| I.A1a.302 | 5-CF₃ | H | 3-Cl | —O— | phenyl |
| I.A1a.303 | 5-CF₃ | H | 3-Cl | —O— | 2-chlorophenyl |
| I.A1a.304 | 5-CF₃ | H | 3-Cl | —O— | 3-chlorophenyl |
| I.A1a.305 | 5-CF₃ | H | 3-Cl | —O— | 4-chlorophenyl |
| I.A1a.306 | 5-CF₃ | H | 3-Cl | —O— | 2,3-dichlorophenyl |
| I.A1a.307 | 5-CF₃ | H | 3-Cl | —O— | 2,5-dichlorophenyl |
| I.A1a.308 | 5-CF₃ | H | 3-Cl | —O— | 3,5-dichlorophenyl |
| I.A1a.309 | 5-CF₃ | H | 3-Cl | —O— | 2,4-dichlorophenyl |
| I.A1a.310 | 5-CF₃ | H | 3-Cl | —O— | 2,6-dichlorophenyl |
| I.A1a.311 | 5-CF₃ | H | 3-Cl | —O— | 2-fluorophenyl |
| I.A1a.312 | 5-CF₃ | H | 3-Cl | —O— | 3-fluorophenyl |
| I.A1a.313 | 5-CF₃ | H | 3-Cl | —O— | 4-fluorophenyl |
| I.A1a.314 | 5-CF₃ | H | 3-Cl | —O— | 2,3-difluorophenyl |
| I.A1a.315 | 5-CF₃ | H | 3-Cl | —O— | 3,5-difluorophenyl |
| I.A1a.316 | 5-CF₃ | H | 3-Cl | —O— | 2-methylphenyl |
| I.A1a.317 | 5-CF₃ | H | 3-Cl | —O— | 3-methylphenyl |
| I.A1a.318 | 5-CF₃ | H | 3-Cl | —O— | 4-methylphenyl |
| I.A1a.319 | 5-CF₃ | H | 3-Cl | —O— | 2,3-dimethylphenyl |
| I.A1a.320 | 5-CF₃ | H | 3-Cl | —O— | 3,5-dimethylphenyl |
| I.A1a.321 | 5-CF₃ | H | 3-Cl | —O— | 2-methoxyphenyl |
| I.A1a.322 | 5-CF₃ | H | 3-Cl | —O— | 3-methoxyphenyl |
| I.A1a.323 | 5-CF₃ | H | 3-Cl | —O— | 4-methoxyphenyl |
| I.A1a.324 | 5-CF₃ | H | 3-Cl | —O— | 2,3-dimethoxyphenyl |
| I.A1a.325 | 5-CF₃ | H | 3-Cl | —O— | 3,5-dimethoxyphenyl |
| I.A1a.326 | 5-CF₃ | H | 3-Cl | —O— | 2,5-dimethoxyphenyl |
| I.A1a.327 | 5-CF₃ | H | 3-Cl | —O— | 3-isopropylphenyl |
| I.A1a.328 | 5-CF₃ | H | 3-Cl | —O— | 3-(n-butyl)phenyl |
| I.A1a.329 | 5-CF₃ | H | 3-Cl | —O— | 3-phenylphenyl |
| I.A1a.330 | 5-CF₃ | H | 3-Cl | —O— | 3-(trifluoromethyl)phenyl |
| I.A1a.331 | 5-CF₃ | H | 3-Cl | —O— | 3-nitrophenyl |
| I.A1a.332 | 5-CF₃ | H | 3-Cl | —O— | 3-bromophenyl |
| I.A1a.333 | 5-CF₃ | H | 3-Cl | —O— | 2,3-dichlorophenyl |
| I.A1a.334 | 5-CF₃ | H | 3-Cl | —O— | 3-cyanophenyl |
| I.A1a.335 | 5-CF₃ | H | 3-Cl | —O— | 3-(phenoxy)phenyl |
| I.A1a.336 | 5-CF₃ | H | 3-Cl | —O— | 3-(trichloromethyl)phenyl |
| I.A1a.337 | 5-CF₃ | H | 3-Cl | —O— | 3-ethylphenyl |
| I.A1a.338 | 5-CF₃ | H | 3-Cl | —O— | 3-(trichloromethoxy)phenyl |
| I.A1a.339 | 5-CF₃ | H | 3-Cl | —O— | 3-(chlorodifluoromethyl)phenyl |
| I.A1a.340 | 5-CF₃ | H | 3-Cl | —O— | 3-(methylcarbonyl)phenyl |
| I.A1a.341 | 5-CF₃ | H | 3-Cl | —O— | 3-(methylsulfonyl)phenyl |
| I.A1a.342 | 5-CF₃ | H | 3-Cl | —O— | 3-(chloromethyl)phenyl |
| I.A1a.343 | 5-CF₃ | H | 3-Cl | —O— | 5-chloro-2-methoxyphenyl |
| I.A1a.344 | 5-CF₃ | H | 3-Cl | —O— | 3-(benzyloxy)phenyl |
| I.A1a.345 | 5-Cl | H | 3-CF₃ | —O— | phenyl |
| I.A1a.346 | 5-Cl | H | 3-CF₃ | —O— | 2-chlorophenyl |
| I.A1a.347 | 5-Cl | H | 3-CF₃ | —O— | 3-chlorophenyl |
| I.A1a.348 | 5-Cl | H | 3-CF₃ | —O— | 4-chlorophenyl |
| I.A1a.349 | 5-Cl | H | 3-CF₃ | —O— | 2,3-dichlorophenyl |
| I.A1a.350 | 5-Cl | H | 3-CF₃ | —O— | 2,5-dichlorophenyl |
| I.A1a.351 | 5-Cl | H | 3-CF₃ | —O— | 3,5-dichlorophenyl |
| I.A1a.352 | 5-Cl | H | 3-CF₃ | —O— | 2,4-dichlorophenyl |
| I.A1a.353 | 5-Cl | H | 3-CF₃ | —O— | 2,6-dichlorophenyl |
| I.A1a.354 | 5-Cl | H | 3-CF₃ | —O— | 2-fluorophenyl |
| I.A1a.355 | 5-Cl | H | 3-CF₃ | —O— | 3-fluorophenyl |
| I.A1a.356 | 5-Cl | H | 3-CF₃ | —O— | 4-fluorophenyl |
| I.A1a.357 | 5-Cl | H | 3-CF₃ | —O— | 2,3-difluorophenyl |
| I.A1a.358 | 5-Cl | H | 3-CF₃ | —O— | 3,5-difluorophenyl |
| I.A1a.359 | 5-Cl | H | 3-CF₃ | —O— | 2-methylphenyl |
| I.A1a.360 | 5-Cl | H | 3-CF₃ | —O— | 3-methylphenyl |
| I.A1a.361 | 5-Cl | H | 3-CF₃ | —O— | 4-methylphenyl |
| I.A1a.362 | 5-Cl | H | 3-CF₃ | —O— | 2,3-dimethylphenyl |
| I.A1a.363 | 5-Cl | H | 3-CF₃ | —O— | 3,5-dimethylphenyl |
| I.A1a.364 | 5-Cl | H | 3-CF₃ | —O— | 2-methoxyphenyl |
| I.A1a.365 | 5-Cl | H | 3-CF₃ | —O— | 3-methoxyphenyl |
| I.A1a.366 | 5-Cl | H | 3-CF₃ | —O— | 4-methoxyphenyl |
| I.A1a.367 | 5-Cl | H | 3-CF₃ | —O— | 2,3-dimethoxyphenyl |
| I.A1a.368 | 5-Cl | H | 3-CF₃ | —O— | 3,5-dimethoxyphenyl |
| I.A1a.369 | 5-Cl | H | 3-CF₃ | —O— | 2,5-dimethoxyphenyl |
| I.A1a.370 | 5-Cl | H | 3-CF₃ | —O— | 3-isopropylphenyl |
| I.A1a.371 | 5-Cl | H | 3-CF₃ | —O— | 3-(n-butyl)phenyl |
| I.A1a.372 | 5-Cl | H | 3-CF₃ | —O— | 3-phenylphenyl |
| I.A1a.373 | 5-Cl | H | 3-CF₃ | —O— | 3-(trifluoromethyl)phenyl |
| I.A1a.374 | 5-Cl | H | 3-CF₃ | —O— | 3-nitrophenyl |
| I.A1a.375 | 5-Cl | H | 3-CF₃ | —O— | 3-bromophenyl |
| I.A1a.376 | 5-Cl | H | 3-CF₃ | —O— | 2,3-dichlorophenyl |
| I.A1a.377 | 5-Cl | H | 3-CF₃ | —O— | 3-cyanophenyl |
| I.A1a.378 | 5-Cl | H | 3-CF₃ | —O— | 3-(phenoxy)phenyl |
| I.A1a.379 | 5-Cl | H | 3-CF₃ | —O— | 3-(trichloromethyl)phenyl |
| I.A1a.380 | 5-Cl | H | 3-CF₃ | —O— | 3-ethylphenyl |
| I.A1a.381 | 5-Cl | H | 3-CF₃ | —O— | 3-(trichloromethoxy)phenyl |
| I.A1a.382 | 5-Cl | H | 3-CF₃ | —O— | 3-(chlorodifluoromethyl)phenyl |
| I.A1a.383 | 5-Cl | H | 3-CF₃ | —O— | 3-(methylcarbonyl)phenyl |
| I.A1a.384 | 5-Cl | H | 3-CF₃ | —O— | 3-(methylsulfonyl)phenyl |
| I.A1a.385 | 5-Cl | H | 3-CF₃ | —O— | 3-(chloromethyl)phenyl |
| I.A1a.386 | 5-Cl | H | 3-CF₃ | —O— | 5-chloro-2-methylphenyl |
| I.A1a.387 | 5-Cl | H | 3-CF₃ | —O— | 3-(benzyloxy)phenyl |
| I.A1a.388 | 6-Cl | H | H | —O— | phenyl |
| I.A1a.389 | 6-Cl | H | H | —O— | 3-chlorophenyl |
| I.A1a.390 | 6-Cl | H | H | —O— | 2,3-dichlorophenyl |
| I.A1a.391 | 6-Cl | H | H | —O— | 2,5-dichlorophenyl |
| I.A1a.392 | 6-Cl | H | H | —O— | 3,5-dichlorophenyl |
| I.A1a.393 | 6-Cl | H | H | —O— | 3-fluorophenyl |
| I.A1a.394 | 6-Cl | H | H | —O— | 2,3-difluorophenyl |
| I.A1a.395 | 6-Cl | H | H | —O— | 3,5-difluorophenyl |
| I.A1a.396 | 6-Cl | H | H | —O— | 3-methylphenyl |
| I.A1a.397 | 6-Cl | H | H | —O— | 2,3-dimethylphenyl |
| I.A1a.398 | 6-Cl | H | H | —O— | 3,5-dimethylphenyl |
| I.A1a.399 | 6-Cl | H | H | —O— | 3-methoxyphenyl |
| I.A1a.400 | 6-Cl | H | H | —O— | 2,3-dimethoxyphenyl |
| I.A1a.401 | 6-Cl | H | H | —O— | 3,5-dimethoxyphenyl |
| I.A1a.402 | 6-Cl | H | H | —O— | 2,5-dimethoxyphenyl |
| I.A1a.403 | 6-Cl | H | H | —O— | 3-isopropylphenyl |
| I.A1a.404 | 6-Cl | H | H | —O— | 3-(n-butyl)phenyl |
| I.A1a.405 | 6-Cl | H | H | —O— | 3-phenylphenyl |
| I.A1a.406 | 6-Cl | H | H | —O— | 3-(trifluoromethyl)phenyl |
| I.A1a.407 | 6-Cl | H | H | —O— | 3-nitrophenyl |
| I.A1a.408 | 6-Cl | H | H | —O— | 3-bromophenyl |
| I.A1a.409 | 6-Cl | H | H | —O— | 2,3-dichlorophenyl |
| I.A1a.410 | 6-Cl | H | H | —O— | 3-cyanophenyl |
| I.A1a.411 | 6-Cl | H | H | —O— | 3-(phenoxy)phenyl |
| I.A1a.412 | 6-Cl | H | H | —O— | 3-(trichloromethyl)phenyl |
| I.A1a.413 | 6-Cl | H | H | —O— | 3-ethylphenyl |
| I.A1a.414 | 6-Cl | H | H | —O— | 3-(trichloromethoxy)phenyl |
| I.A1a.415 | 6-Cl | H | H | —O— | 3-(chlorodifluoromethyl)phenyl |
| I.A1a.416 | 6-Cl | H | H | —O— | 3-(methylcarbonyl)phenyl |
| I.A1a.417 | 6-CF₃ | H | H | —O— | phenyl |
| I.A1a.418 | 6-CF₃ | H | H | —O— | 3-chlorophenyl |

TABLE A-continued

| No. | R¹ | R² | R³ | X | Q |
|---|---|---|---|---|---|
| I.A1a.419 | 6-CF₃ | H | H | —O— | 3,5-dichlorophenyl |
| I.A1a.420 | 6-CF₃ | H | H | —O— | 3-fluorophenyl |
| I.A1a.421 | 6-CF₃ | H | H | —O— | 3-methylphenyl |
| I.A1a.422 | 6-CF₃ | H | H | —O— | 2,3-dimethylphenyl |
| I.A1a.423 | 6-CF₃ | H | H | —O— | 3,5-dimethylphenyl |
| I.A1a.424 | 6-CF₃ | H | H | —O— | 3-methoxyphenyl |
| I.A1a.425 | 6-CF₃ | H | H | —O— | 2,3-dimethoxyphenyl |
| I.A1a.426 | 6-CF₃ | H | H | —O— | 3-isopropylphenyl |
| I.A1a.427 | 6-CF₃ | H | H | —O— | 3-phenylphenyl |
| I.A1a.428 | 6-CF₃ | H | H | —O— | 3-(trifluoromethyl)phenyl |
| I.A1a.429 | 6-CF₃ | H | H | —O— | 3-nitrophenyl |
| I.A1a.430 | 6-CF₃ | H | H | —O— | 3-bromophenyl |
| I.A1a.431 | 6-CF₃ | H | H | —O— | 3-cyanophenyl |
| I.A1a.432 | 6-CF₃ | H | H | —O— | 3-(phenoxy)phenyl |
| I.A1a.433 | H | 4-CF₃ | H | —O— | phenyl |
| I.A1a.434 | H | 4-CF₃ | H | —O— | 3-chlorophenyl |
| I.A1a.435 | H | 4-CF₃ | H | —O— | 3,5-dichlorophenyl |
| I.A1a.436 | H | 4-CF₃ | H | —O— | 3-fluorophenyl |
| I.A1a.437 | H | 4-CF₃ | H | —O— | 3-methylphenyl |
| I.A1a.438 | H | 4-CF₃ | H | —O— | 2,3-dimethylphenyl |
| I.A1a.439 | H | 4-CF₃ | H | —O— | 3,5-dimethylphenyl |
| I.A1a.440 | H | 4-CF₃ | H | —O— | 3-methoxyphenyl |
| I.A1a.441 | H | 4-CF₃ | H | —O— | 2,3-dimethoxyphenyl |
| I.A1a.442 | H | 4-CF₃ | H | —O— | 3-isopropylphenyl |
| I.A1a.443 | H | 4-CF₃ | H | —O— | 3-phenylphenyl |
| I.A1a.444 | H | 4-CF₃ | H | —O— | 3-(trifluoromethyl)phenyl |
| I.A1a.445 | H | 4-CF₃ | H | —O— | 3-nitrophenyl |
| I.A1a.446 | H | 4-CF₃ | H | —O— | 3-bromophenyl |
| I.A1a.447 | H | 4-CF₃ | H | —O— | 3-cyanophenyl |
| I.A1a.448 | H | 4-CF₃ | H | —O— | 3-(phenoxy)phenyl |
| I.A1a.449 | H | H | 3-NO₂ | —O— | phenyl |
| I.A1a.450 | H | H | 3-NO₂ | —O— | 3-chlorophenyl |
| I.A1a.451 | H | H | 3-NO₂ | —O— | 3,5-dichlorophenyl |
| I.A1a.452 | H | H | 3-NO₂ | —O— | 3-fluorophenyl |
| I.A1a.453 | H | H | 3-NO₂ | —O— | 3-methylphenyl |
| I.A1a.454 | H | H | 3-NO₂ | —O— | 2,3-dimethylphenyl |
| I.A1a.455 | H | H | 3-NO₂ | —O— | 3,5-dimethylphenyl |
| I.A1a.456 | H | H | 3-NO₂ | —O— | 3-methoxyphenyl |
| I.A1a.457 | H | H | 3-NO₂ | —O— | 2,3-dimethoxyphenyl |
| I.A1a.458 | H | H | 3-NO₂ | —O— | 3-isopropylphenyl |
| I.A1a.459 | H | H | 3-NO₂ | —O— | 3-phenylphenyl |
| I.A1a.460 | H | H | 3-NO₂ | —O— | 3-(trifluoromethyl)phenyl |
| I.A1a.461 | H | H | 3-NO₂ | —O— | 3-nitrophenyl |
| I.A1a.462 | H | H | 3-NO₂ | —O— | 3-bromophenyl |
| I.A1a.463 | H | H | 3-NO₂ | —O— | 3-cyanophenyl |
| I.A1a.464 | H | H | 3-NO₂ | —O— | 3-(phenoxy)phenyl |
| I.A1a.465 | 6-Cl | 5-CF₃ | H | —O— | phenyl |
| I.A1a.466 | 6-Cl | 5-CF₃ | H | —O— | 3-chlorophenyl |
| I.A1a.467 | 6-Cl | 5-CF₃ | H | —O— | 3-fluorophenyl |
| I.A1a.468 | 6-Cl | 5-CF₃ | H | —O— | 3-methylphenyl |
| I.A1a.469 | 6-Cl | 5-CF₃ | H | —O— | 3-methoxyphenyl |
| I.A1a.470 | 6-Cl | 5-CF₃ | H | —O— | 3-phenylphenyl |
| I.A1a.471 | 6-Cl | 5-CF₃ | H | —O— | 3-(trifluoromethyl)phenyl |
| I.A1a.472 | 6-Cl | 5-CF₃ | H | —O— | 3-nitrophenyl |
| I.A1a.473 | 6-Cl | 5-CF₃ | H | —O— | 3-cyanophenyl |
| I.A1a.474 | H | 5-CF₃ | 3-CN | —O— | phenyl |
| I.A1a.475 | H | 5-CF₃ | 3-CN | —O— | 3-chlorophenyl |
| I.A1a.476 | H | 5-CF₃ | 3-CN | —O— | 3-fluorophenyl |
| I.A1a.477 | H | 5-CF₃ | 3-CN | —O— | 3-methylphenyl |
| I.A1a.478 | H | 5-CF₃ | 3-CN | —O— | 3-methoxyphenyl |
| I.A1a.479 | H | 5-CF₃ | 3-CN | —O— | 3-phenylphenyl |
| I.A1a.480 | H | 5-CF₃ | 3-CN | —O— | 3-(trifluoromethyl)phenyl |
| I.A1a.481 | H | 5-CF₃ | 3-CN | —O— | 3-nitrophenyl |
| I.A1a.482 | H | 5-CF₃ | 3-CN | —O— | 3-cyanophenyl |
| I.A1a.483 | 6-Cl | 4-CF₃ | H | —O— | phenyl |
| I.A1a.484 | 6-Cl | 4-CF₃ | H | —O— | 3-chlorophenyl |
| I.A1a.485 | 6-Cl | 4-CF₃ | H | —O— | 3-fluorophenyl |
| I.A1a.486 | 6-Cl | 4-CF₃ | H | —O— | 3-methylphenyl |
| I.A1a.487 | 6-Cl | 4-CF₃ | H | —O— | 3-methoxyphenyl |
| I.A1a.488 | 6-Cl | 4-CF₃ | H | —O— | 3-phenylphenyl |
| I.A1a.489 | 6-Cl | 4-CF₃ | H | —O— | 3-(trifluoromethyl)phenyl |
| I.A1a.490 | 6-Cl | 4-CF₃ | H | —O— | 3-nitrophenyl |
| I.A1a.491 | 6-Cl | 4-CF₃ | H | —O— | 3-cyanophenyl |
| I.A1a.492 | 6-Cl | H | 3-CN | —O— | phenyl |
| I.A1a.493 | 6-Cl | H | 3-CN | —O— | 3-chlorophenyl |
| I.A1a.494 | 6-Cl | H | 3-CN | —O— | 3-fluorophenyl |
| I.A1a.495 | 6-Cl | H | 3-CN | —O— | 3-methylphenyl |
| I.A1a.496 | 6-Cl | H | 3-CN | —O— | 3-methoxyphenyl |
| I.A1a.497 | 6-Cl | H | 3-CN | —O— | 3-phenylphenyl |
| I.A1a.498 | 6-Cl | H | 3-CN | —O— | 3-(trifluoromethyl)phenyl |
| I.A1a.499 | 6-Cl | H | 3-CN | —O— | 3-nitrophenyl |
| I.A1a.500 | 6-Cl | H | 3-CN | —O— | 3-cyanophenyl |
| I.A1a.501 | 6-CH₃ | 4-CH₃ | 3-CN | —O— | phenyl |
| I.A1a.502 | 6-CH₃ | 4-CH₃ | 3-CN | —O— | 3-chlorophenyl |
| I.A1a.503 | 6-CH₃ | 4-CH₃ | 3-CN | —O— | 3-fluorophenyl |
| I.A1a.504 | 6-CH₃ | 4-CH₃ | 3-CN | —O— | 3-methylphenyl |
| I.A1a.505 | 6-CH₃ | 4-CH₃ | 3-CN | —O— | 3-methoxyphenyl |
| I.A1a.506 | 6-CH₃ | 4-CH₃ | 3-CN | —O— | 3-phenylphenyl |
| I.A1a.507 | 6-CH₃ | 4-CH₃ | 3-CN | —O— | 3-(trifluoromethyl)phenyl |
| I.A1a.508 | 6-CH₃ | 4-CH₃ | 3-CN | —O— | 3-nitrophenyl |
| I.A1a.509 | 6-CH₃ | 4-CH₃ | 3-CN | —O— | 3-cyanophenyl |
| I.A1a.510 | 5-CF₃ | H | 3-Cl | —O— | 3,4-dichlorophenyl |
| I.A1a.511 | 6-Cl | H | 3-NO₂ | —O— | 3-chlorophenyl |
| I.A1a.512 | 6-Cl | 5-NO₂ | H | —O— | 3-chlorophenyl |
| I.A1a.513 | 6-Cl | 5-CN | H | —O— | 3-chlorophenyl |

TABLE B

| No. | R¹ | R² | R³ | X | Q |
|---|---|---|---|---|---|
| I.A1a.1001 | H | H | H | —S— | phenyl |
| I.A1a.1002 | H | H | H | —S— | 2-chlorophenyl |
| I.A1a.1003 | H | H | H | —S— | 3-chlorophenyl |
| I.A1a.1004 | H | H | H | —S— | 4-chlorophenyl |
| I.A1a.1005 | H | H | H | —S— | 2,3-dichlorophenyl |
| I.A1a.1006 | H | H | H | —S— | 2,5-dichlorophenyl |
| I.A1a.1007 | H | H | H | —S— | 3,5-dichlorophenyl |
| I.A1a.1008 | H | H | H | —S— | 2,4-dichlorophenyl |

TABLE B-continued

| No. | R¹ | R² | R³ | X | Q |
|---|---|---|---|---|---|
| I.Ala.1009 | H | H | H | —S— | 2,6-dichlorophenyl |
| I.Ala.1010 | H | H | H | —S— | 2-fluorophenyl |
| I.Ala.1011 | H | H | H | —S— | 3-fluorophenyl |
| I.Ala.1012 | H | H | H | —S— | 4-fluorophenyl |
| I.Ala.1013 | H | H | H | —S— | 2,3-difluorophenyl |
| I.Ala.1014 | H | H | H | —S— | 3,5-difluorophenyl |
| I.Ala.1015 | H | H | H | —S— | 2-methylphenyl |
| I.Ala.1016 | H | H | H | —S— | 3-methylphenyl |
| I.Ala.1017 | H | H | H | —S— | 4-methylphenyl |
| I.Ala.1018 | H | H | H | —S— | 2,3-dimethylphenyl |
| I.Ala.1019 | H | H | H | —S— | 3,5-dimethylphenyl |
| I.Ala.1020 | H | H | H | —S— | 2-methoxyphenyl |
| I.Ala.1021 | H | H | H | —S— | 3-methoxyphenyl |
| I.Ala.1022 | H | H | H | —S— | 4-methoxyphenyl |
| I.Ala.1023 | H | H | H | —S— | 2,3-dimethoxyphenyl |
| I.Ala.1024 | H | H | H | —S— | 3,5-dimethoxyphenyl |
| I.Ala.1025 | H | H | H | —S— | 2,5-dimethoxyphenyl |
| I.Ala.1026 | H | H | H | —S— | 3-isopropylphenyl |
| I.Ala.1027 | H | H | H | —S— | 3-(n-butyl)phenyl |
| I.Ala.1028 | H | H | H | —S— | 3-phenylphenyl |
| I.Ala.1029 | H | H | H | —S— | 3-trifluoromethylphenyl |
| I.Ala.1030 | H | H | H | —S— | 3-nitrophenyl |
| I.Ala.1031 | H | H | H | —S— | 3-bromophenyl |
| I.Ala.1032 | H | H | H | —S— | 2,3-dichlorophenyl |
| I.Ala.1033 | H | H | H | —S— | 3-cyanophenyl |
| I.Ala.1034 | H | H | H | —S— | 3-phenoxyphenyl |
| I.Ala.1035 | H | H | H | —S— | 3-(trichloromethyl)phenyl |
| I.Ala.1036 | H | H | H | —S— | 3-ethylphenyl |
| I.Ala.1037 | H | H | H | —S— | 3-(trichloromethoxy)phenyl |
| I.Ala.1038 | H | H | H | —S— | 3-(chlorodifluoromethyl)-phenyl |
| I.Ala.1039 | H | H | H | —S— | 3-(methylcarbonyl)phenyl |
| I.Ala.1040 | H | H | H | —S— | 3-(methylsulfonyl)phenyl |
| I.Ala.1041 | H | H | H | —S— | 3-(chloromethyl)phenyl |
| I.Ala.1042 | H | H | H | —S— | 5-chloro-2-methoxy-phenyl |
| I.Ala.1043 | H | H | H | —S— | 3-(benzyloxy)phenyl |
| I.Ala.1044 | H | H | 3-Cl | —S— | phenyl |
| I.Ala.1045 | H | H | 3-Cl | —S— | 2-chlorophenyl |
| I.Ala.1046 | H | H | 3-Cl | —S— | 3-chlorophenyl |
| I.Ala.1047 | H | H | 3-Cl | —S— | 4-chlorophenyl |
| I.Ala.1048 | H | H | 3-Cl | —S— | 2,3-dichlorophenyl |
| I.Ala.1049 | H | H | 3-Cl | —S— | 2,5-dichlorophenyl |
| I.Ala.1050 | H | H | 3-Cl | —S— | 3,5-dichlorophenyl |
| I.Ala.1051 | H | H | 3-Cl | —S— | 2,4-dichlorophenyl |
| I.Ala.1052 | H | H | 3-Cl | —S— | 2,6-dichlorophenyl |
| I.Ala.1053 | H | H | 3-Cl | —S— | 2-fluorophenyl |
| I.Ala.1054 | H | H | 3-Cl | —S— | 3-fluorophenyl |
| I.Ala.1055 | H | H | 3-Cl | —S— | 4-fluorophenyl |
| I.Ala.1056 | H | H | 3-Cl | —S— | 2,3-difluorophenyl |
| I.Ala.1057 | H | H | 3-Cl | —S— | 3,5-difluorophenyl |
| I.Ala.1058 | H | H | 3-Cl | —S— | 2-methylphenyl |
| I.Ala.1059 | H | H | 3-Cl | —S— | 3-methylphenyl |
| I.Ala.1060 | H | H | 3-Cl | —S— | 4-methylphenyl |
| I.Ala.1061 | H | H | 3-Cl | —S— | 2,3-dimethylphenyl |
| I.Ala.1062 | H | H | 3-Cl | —S— | 3,5-dimethylphenyl |
| I.Ala.1063 | H | H | 3-Cl | —S— | 2-methoxyphenyl |
| I.Ala.1064 | H | H | 3-Cl | —S— | 3-methoxyphenyl |
| I.Ala.1065 | H | H | 3-Cl | —S— | 4-methoxyphenyl |
| I.Ala.1066 | H | H | 3-Cl | —S— | 2,3-dimethoxyphenyl |
| I.Ala.1067 | H | H | 3-Cl | —S— | 3,5-dimethoxyphenyl |
| I.Ala.1068 | H | H | 3-Cl | —S— | 2,5-dimethoxyphenyl |
| I.Ala.1069 | H | H | 3-Cl | —S— | 3-isopropylphenyl |
| I.Ala.1070 | H | H | 3-Cl | —S— | 3-(n-butyl)phenyl |
| I.Ala.1071 | H | H | 3-Cl | —S— | 3-phenylphenyl |
| I.Ala.1072 | H | H | 3-Cl | —S— | 3-(trifluoromethyl)phenyl |
| I.Ala.1073 | H | H | 3-Cl | —S— | 3-nitrophenyl |
| I.Ala.1074 | H | H | 3-Cl | —S— | 3-bromophenyl |
| I.Ala.1075 | H | H | 3-Cl | —S— | 2,3-dichlorophenyl |
| I.Ala.1076 | H | H | 3-Cl | —S— | 3-cyanophenyl |
| I.Ala.1077 | H | H | 3-Cl | —S— | 3-phenyloxyphenyl |
| I.Ala.1078 | H | H | 3-Cl | —S— | 3-trichloromethylphenyl |
| I.Ala.1079 | H | H | 3-Cl | —S— | 3-ethylphenyl |
| I.Ala.1080 | H | H | 3-Cl | —S— | 3-(trichloromethoxy)phenyl |
| I.Ala.1081 | H | H | 3-Cl | —S— | 3-(chlorodifluoromethyl)-phenyl |
| I.Ala.1082 | H | H | 3-Cl | —S— | 3-(methylcarbonyl)phenyl |
| I.Ala.1083 | H | H | 3-Cl | —S— | 3-(methylsulfonyl)phenyl |

TABLE B-continued

| No. | R¹ | R² | R³ | X | Q |
|---|---|---|---|---|---|
| I.Ala.1084 | H | H | 3-Cl | —S— | 3-(chloromethyl)phenyl |
| I.Ala.1085 | H | H | 3-Cl | —S— | 5-chloro-2-methoxyphenyl |
| I.Ala.1086 | H | H | 3-Cl | —S— | 3-benzyloxyphenyl |
| I.Ala.1087 | H | H | 3-CF₃ | —S— | phenyl |
| I.Ala.1088 | H | H | 3-CF₃ | —S— | 2-chlorophenyl |
| I.Ala.1089 | H | H | 3-CF₃ | —S— | 3-chlorophenyl |
| I.Ala.1090 | H | H | 3-CF₃ | —S— | 4-chlorophenyl |
| I.Ala.1091 | H | H | 3-CF₃ | —S— | 2,3-dichlorophenyl |
| I.Ala.1092 | H | H | 3-CF₃ | —S— | 2,5-dichlorophenyl |
| I.Ala.1093 | H | H | 3-CF₃ | —S— | 3,5-dichlorophenyl |
| I.Ala.1094 | H | H | 3-CF₃ | —S— | 2,4-dichlorophenyl |
| I.Ala.1095 | H | H | 3-CF₃ | —S— | 2,6-dichlorophenyl |
| I.Ala.1096 | H | H | 3-CF₃ | —S— | 2-fluorophenyl |
| I.Ala.1097 | H | H | 3-CF₃ | —S— | 3-fluorophenyl |
| I.Ala.1098 | H | H | 3-CF₃ | —S— | 4-fluorophenyl |
| I.Ala.1099 | H | H | 3-CF₃ | —S— | 2,3-difluorophenyl |
| I.Ala.1100 | H | H | 3-CF₃ | —S— | 3,5-difluorophenyl |
| I.Ala.1101 | H | H | 3-CF₃ | —S— | 2-methylphenyl |
| I.Ala.1102 | H | H | 3-CF₃ | —S— | 3-methylphenyl |
| I.Ala.1103 | H | H | 3-CF₃ | —S— | 4-methylphenyl |
| I.Ala.1104 | H | H | 3-CF₃ | —S— | 2,3-dimethylphenyl |
| I.Ala.1105 | H | H | 3-CF₃ | —S— | 3,5-dimethylphenyl |
| I.Ala.1106 | H | H | 3-CF₃ | —S— | 2-methoxyphenyl |
| I.Ala.1107 | H | H | 3-CF₃ | —S— | 3-methoxyphenyl |
| I.Ala.1108 | H | H | 3-CF₃ | —S— | 4-methoxyphenyl |
| I.Ala.1109 | H | H | 3-CF₃ | —S— | 2,3-dimethoxyphenyl |
| I.Ala.1110 | H | H | 3-CF₃ | —S— | 3,5-dimethoxyphenyl |
| I.Ala.1111 | H | H | 3-CF₃ | —S— | 2,5-dimethoxyphenyl |
| I.Ala.1112 | H | H | 3-CF₃ | —S— | 3-isopropylphenyl |
| I.Ala.1113 | H | H | 3-CF₃ | —S— | 3-(n-butyl)phenyl |
| I.Ala.1114 | H | H | 3-CF₃ | —S— | 3-phenylphenyl |
| I.Ala.1115 | H | H | 3-CF₃ | —S— | 3-(trifluoromethyl)phenyl |
| I.Ala.1116 | H | H | 3-CF₃ | —S— | 3-nitrophenyl |
| I.Ala.1117 | H | H | 3-CF₃ | —S— | 3-bromophenyl |
| I.Ala.1118 | H | H | 3-CF₃ | —S— | 2,3-dichlorophenyl |
| I.Ala.1119 | H | H | 3-CF₃ | —S— | 3-cyanophenyl |
| I.Ala.1120 | H | H | 3-CF₃ | —S— | 3-phenoxyphenyl |
| I.Ala.1121 | H | H | 3-CF₃ | —S— | 3-(trichloromethyl)phenyl |
| I.Ala.1122 | H | H | 3-CF₃ | —S— | 3-ethylphenyl |
| I.Ala.1123 | H | H | 3-CF₃ | —S— | 3-(trichloromethoxy)phenyl |
| I.Ala.1124 | H | H | 3-CF₃ | —S— | 3-(chlorodifluoromethyl)-phenyl |
| I.Ala.1125 | H | H | 3-CF₃ | —S— | 3-(methylcarbonyl)phenyl |
| I.Ala.1126 | H | H | 3-CF₃ | —S— | 3-(methylsulfonyl)phenyl |
| I.Ala.1127 | H | H | 3-CF₃ | —S— | 3-(chloromethyl)phenyl |
| I.Ala.1128 | H | H | 3-CF₃ | —S— | 5-chloro-2-methoxyphenyl |
| I.Ala.1129 | H | H | 3-CF₃ | —S— | 3-(benzyloxy)phenyl |
| I.Ala.1130 | H | H | 3-CN | —S— | phenyl |
| I.Ala.1131 | H | H | 3-CN | —S— | 2-chlorophenyl |
| I.Ala.1132 | H | H | 3-CN | —S— | 3-chlorophenyl |
| I.Ala.1133 | H | H | 3-CN | —S— | 4-chlorophenyl |
| I.Ala.1134 | H | H | 3-CN | —S— | 2,3-dichlorophenyl |
| I.Ala.1135 | H | H | 3-CN | —S— | 2,5-dichlorophenyl |
| I.Ala.1136 | H | H | 3-CN | —S— | 3,5-dichlorophenyl |
| I.Ala.1137 | H | H | 3-CN | —S— | 2,4-dichlorophenyl |
| I.Ala.1138 | H | H | 3-CN | —S— | 2,6-dichlorophenyl |
| I.Ala.1139 | H | H | 3-CN | —S— | 2-fluorophenyl |
| I.Ala.1140 | H | H | 3-CN | —S— | 3-fluorophenyl |
| I.Ala.1141 | H | H | 3-CN | —S— | 4-fluorophenyl |
| I.Ala.1142 | H | H | 3-CN | —S— | 2,3-difluorophenyl |
| I.Ala.1143 | H | H | 3-CN | —S— | 3,5-difluorophenyl |
| I.Ala.1144 | H | H | 3-CN | —S— | 2-methylphenyl |
| I.Ala.1145 | H | H | 3-CN | —S— | 3-methylphenyl |
| I.Ala.1146 | H | H | 3-CN | —S— | 4-methylphenyl |
| I.Ala.1147 | H | H | 3-CN | —S— | 2,3-dimethylphenyl |
| I.Ala.1148 | H | H | 3-CN | —S— | 3,5-dimethylphenyl |
| I.Ala.1149 | H | H | 3-CN | —S— | 2-methoxyphenyl |
| I.Ala.1150 | H | H | 3-CN | —S— | 3-methoxyphenyl |
| I.Ala.1151 | H | H | 3-CN | —S— | 4-methoxyphenyl |
| I.Ala.1152 | H | H | 3-CN | —S— | 2,3-dimethoxyphenyl |
| I.Ala.1153 | H | H | 3-CN | —S— | 3,5-dimethoxyphenyl |
| I.Ala.1154 | H | H | 3-CN | —S— | 2,5-dimethoxyphenyl |
| I.Ala.1155 | H | H | 3-CN | —S— | 3-isopropylphenyl |
| I.Ala.1156 | H | H | 3-CN | —S— | 3-(n-butyl)phenyl |
| I.Ala.1157 | H | H | 3-CN | —S— | 3-phenylphenyl |
| I.Ala.1158 | H | H | 3-CN | —S— | 3-(trifluoromethyl)phenyl |
| I.Ala.1159 | H | H | 3-CN | —S— | 3-nitrophenyl |

TABLE B-continued

| No. | R¹ | R² | R³ | X | Q |
|---|---|---|---|---|---|
| I.Ala.1160 | H | H | 3-CN | —S— | 3-bromophenyl |
| I.Ala.1161 | H | H | 3-CN | —S— | 2,3-dichlorophenyl |
| I.Ala.1162 | H | H | 3-CN | —S— | 3-cyanophenyl |
| I.Ala.1163 | H | H | 3-CN | —S— | 3-phenoxyphenyl |
| I.Ala.1164 | H | H | 3-CN | —S— | 3-(trichloromethyl)phenyl |
| I.Ala.1165 | H | H | 3-CN | —S— | 3-ethylphenyl |
| I.Ala.1166 | H | H | 3-CN | —S— | 3-trichloromethoxyphenyl |
| I.Ala.1167 | H | H | 3-CN | —S— | 3-(chlorodifluoro)phenyl |
| I.Ala.1168 | H | H | 3-CN | —S— | 3-(methylcarbonyl)phenyl |
| I.Ala.1169 | H | H | 3-CN | —S— | 3-(methylsulfonyl)phenyl |
| I.Ala.1170 | H | H | 3-CN | —S— | 3-(chloromethyl)phenyl |
| I.Ala.1171 | H | H | 3-CN | —S— | 5-chloro-2-methoxyphenyl |
| I.Ala.1172 | H | H | 3-CN | —S— | 3-benzyloxyphenyl |
| I.Ala.1173 | 5-Cl | H | H | —S— | phenyl |
| I.Ala.1174 | 5-Cl | H | H | —S— | 2-chloro |
| I.Ala.1175 | 5-Cl | H | H | —S— | 3-chloro |
| I.Ala.1176 | 5-Cl | H | H | —S— | 4-chloro |
| I.Ala.1177 | 5-Cl | H | H | —S— | 2,3-dichlorophenyl |
| I.Ala.1178 | 5-Cl | H | H | —S— | 2,5-dichlorophenyl |
| I.Ala.1179 | 5-Cl | H | H | —S— | 3,5-dichlorophenyl |
| I.Ala.1180 | 5-Cl | H | H | —S— | 2,4-dichlorophenyl |
| I.Ala.1181 | 5-Cl | H | H | —S— | 2,6-dichlorophenyl |
| I.Ala.1182 | 5-Cl | H | H | —S— | 2-fluorophenyl |
| I.Ala.1183 | 5-Cl | H | H | —S— | 3-fluorophenyl |
| I.Ala.1184 | 5-Cl | H | H | —S— | 4-fluorophenyl |
| I.Ala.1185 | 5-Cl | H | H | —S— | 2,3-difluorophenyl |
| I.Ala.1186 | 5-Cl | H | H | —S— | 3,5-difluorophenyl |
| I.Ala.1187 | 5-Cl | H | H | —S— | 2-methylphenyl |
| I.Ala.1188 | 5-Cl | H | H | —S— | 3-methylphenyl |
| I.Ala.1189 | 5-Cl | H | H | —S— | 4-methylphenyl |
| I.Ala.1190 | 5-Cl | H | H | —S— | 2,3-dimethylphenyl |
| I.Ala.1191 | 5-Cl | H | H | —S— | 3,5-dimethylphenyl |
| I.Ala.1192 | 5-Cl | H | H | —S— | 2-methoxyphenyl |
| I.Ala.1193 | 5-Cl | H | H | —S— | 3-methoxyphenyl |
| I.Ala.1194 | 5-Cl | H | H | —S— | 4-methoxyphenyl |
| I.Ala.1195 | 5-Cl | H | H | —S— | 2,3-dimethoxyphenyl |
| I.Ala.1196 | 5-Cl | H | H | —S— | 3,5-dimethoxyphenyl |
| I.Ala.1197 | 5-Cl | H | H | —S— | 2,5-dimethoxyphenyl |
| I.Ala.1198 | 5-Cl | H | H | —S— | 3-isopropylphenyl |
| I.Ala.1199 | 5-Cl | H | H | —S— | 3-(n-butyl)phenyl |
| I.Ala.1200 | 5-Cl | H | H | —S— | 3-(phenyl)phenyl |
| I.Ala.1201 | 5-Cl | H | H | —S— | 3-(trifluoromethyl)phenyl |
| I.Ala.1202 | 5-Cl | H | H | —S— | 3-nitrophenyl |
| I.Ala.1203 | 5-Cl | H | H | —S— | 3-bromophenyl |
| I.Ala.1204 | 5-Cl | H | H | —S— | 2,3-dichlorophenyl |
| I.Ala.1205 | 5-Cl | H | H | —S— | 3-cyanophenyl |
| I.Ala.1206 | 5-Cl | H | H | —S— | 3-(phenoxy)phenyl |
| I.Ala.1207 | 5-Cl | H | H | —S— | 3-(trichloromethyl)phenyl |
| I.Ala.1208 | 5-Cl | H | H | —S— | 3-ethylphenyl |
| I.Ala.1209 | 5-Cl | H | H | —S— | 3-(trichloromethoxy)phenyl |
| I.Ala.1210 | 5-Cl | H | H | —S— | 3-(chlorodifluoromethyl)-phenyl |
| I.Ala.1211 | 5-Cl | H | H | —S— | 3-(methylcarbonyl)phenyl |
| I.Ala.1212 | 5-Cl | H | H | —S— | 3-(methylsulfonyl)phenyl |
| I.Ala.1213 | 5-Cl | H | H | —S— | 3-(chloromethyl)phenyl |
| I.Ala.1214 | 5-Cl | H | H | —S— | 5-chloro-2-methoxyphenyl |
| I.Ala.1215 | 5-Cl | H | H | —S— | 3-(benzyloxy)phenyl |
| I.Ala.1216 | 5-CF₃ | H | H | —S— | phenyl |
| I.Ala.1217 | 5-CF₃ | H | H | —S— | 2-chlorophenyl |
| I.Ala.1218 | 5-CF₃ | H | H | —S— | 3-chlorophenyl |
| I.Ala.1219 | 5-CF₃ | H | H | —S— | 4-chlorophenyl |
| I.Ala.1220 | 5-CF₃ | H | H | —S— | 2,3-dichlorophenyl |
| I.Ala.1221 | 5-CF₃ | H | H | —S— | 2,5-dichlorophenyl |
| I.Ala.1222 | 5-CF₃ | H | H | —S— | 3,5-dichlorophenyl |
| I.Ala.1223 | 5-CF₃ | H | H | —S— | 2,4-dichlorophenyl |
| I.Ala.1224 | 5-CF₃ | H | H | —S— | 2,6-dichlorophenyl |
| I.Ala.1225 | 5-CF₃ | H | H | —S— | 2-fluorophenyl |
| I.Ala.1226 | 5-CF₃ | H | H | —S— | 3-fluorophenyl |
| I.Ala.1227 | 5-CF₃ | H | H | —S— | 4-fluorophenyl |
| I.Ala.1228 | 5-CF₃ | H | H | —S— | 2,3-difluorophenyl |
| I.Ala.1229 | 5-CF₃ | H | H | —S— | 3,5-difluorophenyl |
| I.Ala.1230 | 5-CF₃ | H | H | —S— | 2-methylphenyl |
| I.Ala.1231 | 5-CF₃ | H | H | —S— | 3-methylphenyl |
| I.Ala.1232 | 5-CF₃ | H | H | —S— | 4-methylphenyl |
| I.Ala.1233 | 5-CF₃ | H | H | —S— | 2,3-dimethylphenyl |
| I.Ala.1234 | 5-CF₃ | H | H | —S— | 3,5-dimethylphenyl |
| I.Ala.1235 | 5-CF₃ | H | H | —S— | 2-methoxyphenyl |

TABLE B-continued

| No. | R¹ | R² | R³ | X | Q |
|---|---|---|---|---|---|
| I.Ala.1236 | 5-CF₃ | H | H | —S— | 3-methoxyphenyl |
| I.Ala.1237 | 5-CF₃ | H | H | —S— | 4-methoxyphenyl |
| I.Ala.1238 | 5-CF₃ | H | H | —S— | 2,3-dimethoxyphenyl |
| I.Ala.1239 | 5-CF₃ | H | H | —S— | 3,5-dimethoxyphenyl |
| I.Ala.1240 | 5-CF₃ | H | H | —S— | 2,5-dimethoxyphenyl |
| I.Ala.1241 | 5-CF₃ | H | H | —S— | 3-isopropylphenyl |
| I.Ala.1242 | 5-CF₃ | H | H | —S— | 3-(n-butyl)phenyl |
| I.Ala.1243 | 5-CF₃ | H | H | —S— | 3-phenylphenyl |
| I.Ala.1244 | 5-CF₃ | H | H | —S— | 3-(trifluoromethyl)phenyl |
| I.Ala.1245 | 5-CF₃ | H | H | —S— | 3-nitrophenyl |
| I.Ala.1246 | 5-CF₃ | H | H | —S— | 3-bromophenyl |
| I.Ala.1247 | 5-CF₃ | H | H | —S— | 2,3-dichlorophenyl |
| I.Ala.1248 | 5-CF₃ | H | H | —S— | 3-cyanophenyl |
| I.Ala.1249 | 5-CF₃ | H | H | —S— | 3-(phenoxy)phenyl |
| I.Ala.1250 | 5-CF₃ | H | H | —S— | 3-(trichloromethyl)phenyl |
| I.Ala.1251 | 5-CF₃ | H | H | —S— | 3-ethylphenyl |
| I.Ala.1252 | 5-CF₃ | H | H | —S— | 3-(trichloromethoxy)phenyl |
| I.Ala.1253 | 5-CF₃ | H | H | —S— | 3-(chlorodifluoromethyl)-phenyl |
| I.Ala.1254 | 5-CF₃ | H | H | —S— | 3-(methylcarbonyl)phenyl |
| I.Ala.1255 | 5-CF₃ | H | H | —S— | 3-(methylsulfonyl)phenyl |
| I.Ala.1256 | 5-CF₃ | H | H | —S— | 3-(chloromethyl)phenyl |
| I.Ala.1257 | 5-CF₃ | H | H | —S— | 5-chloro-2-methoxyphenyl |
| I.Ala.1258 | 5-CF₃ | H | H | —S— | 3-(benzyloxy)phenyl |
| I.Ala.1259 | 5-CN | H | H | —S— | phenyl |
| I.Ala.1260 | 5-CN | H | H | —S— | 2-chlorophenyl |
| I.Ala.1261 | 5-CN | H | H | —S— | 3-chlorophenyl |
| I.Ala.1262 | 5-CN | H | H | —S— | 4-chlorophenyl |
| I.Ala.1263 | 5-CN | H | H | —S— | 2,3-dichlorophenyl |
| I.Ala.1264 | 5-CN | H | H | —S— | 2,5-dichlorophenyl |
| I.Ala.1265 | 5-CN | H | H | —S— | 3,5-dichlorophenyl |
| I.Ala.1266 | 5-CN | H | H | —S— | 2,4-dichlorophenyl |
| I.Ala.1267 | 5-CN | H | H | —S— | 2,6-dichlorophenyl |
| I.Ala.1268 | 5-CN | H | H | —S— | 2-fluorophenyl |
| I.Ala.1269 | 5-CN | H | H | —S— | 3-fluorophenyl |
| I.Ala.1270 | 5-CN | H | H | —S— | 4-fluorophenyl |
| I.Ala.1271 | 5-CN | H | H | —S— | 2,3-difluorophenyl |
| I.Ala.1272 | 5-CN | H | H | —S— | 3,5-difluorophenyl |
| I.Ala.1273 | 5-CN | H | H | —S— | 2-methylphenyl |
| I.Ala.1274 | 5-CN | H | H | —S— | 3-methylphenyl |
| I.Ala.1275 | 5-CN | H | H | —S— | 4-methylphenyl |
| I.Ala.1276 | 5-CN | H | H | —S— | 2,3-dimethylphenyl |
| I.Ala.1277 | 5-CN | H | H | —S— | 3,5-dimethylphenyl |
| I.Ala.1278 | 5-CN | H | H | —S— | 2-methoxyphenyl |
| I.Ala.1279 | 5-CN | H | H | —S— | 3-methoxyphenyl |
| I.Ala.1280 | 5-CN | H | H | —S— | 4-methoxyphenyl |
| I.Ala.1281 | 5-CN | H | H | —S— | 2,3-dimethoxyphenyl |
| I.Ala.1282 | 5-CN | H | H | —S— | 3,5-dimethoxyphenyl |
| I.Ala.1283 | 5-CN | H | H | —S— | 2,5-dimethoxyphenyl |
| I.Ala.1284 | 5-CN | H | H | —S— | 3-isopropylphenyl |
| I.Ala.1285 | 5-CN | H | H | —S— | 3-(n-butyl)phenyl |
| I.Ala.1286 | 5-CN | H | H | —S— | 3-phenylphenyl |
| I.Ala.1287 | 5-CN | H | H | —S— | 3-(trifluoromethyl)phenyl |
| I.Ala.1288 | 5-CN | H | H | —S— | 3-nitrophenyl |
| I.Ala.1289 | 5-CN | H | H | —S— | 3-bromophenyl |
| I.Ala.1290 | 5-CN | H | H | —S— | 2,3-dichlorophenyl |
| I.Ala.1291 | 5-CN | H | H | —S— | 3-cyanophenyl |
| I.Ala.1292 | 5-CN | H | H | —S— | 3-(phenoxy)phenyl |
| I.Ala.1293 | 5-CN | H | H | —S— | 3-(trichloromethyl)phenyl |
| I.Ala.1294 | 5-CN | H | H | —S— | 3-ethylphenyl |
| I.Ala.1295 | 5-CN | H | H | —S— | 3-(trichloromethoxy)phenyl |
| I.Ala.1296 | 5-CN | H | H | —S— | 3-(chlorodifluoromethyl)-phenyl |
| I.Ala.1297 | 5-CN | H | H | —S— | 3-(methylcarbonyl)phenyl |
| I.Ala.1298 | 5-CN | H | H | —S— | 3-(methylsulfonyl)phenyl |
| I.Ala.1299 | 5-CN | H | H | —S— | 3-(chloromethyl)phenyl |
| I.Ala.1300 | 5-CN | H | H | —S— | 5-chloro-2-methoxyphenyl |
| I.Ala.1301 | 5-CN | H | H | —S— | 3-(benzyloxy)phenyl |
| I.Ala.1302 | 5-CF₃ | H | 3-Cl | —S— | phenyl |
| I.Ala.1303 | 5-CF₃ | H | 3-Cl | —S— | 2-chlorophenyl |
| I.Ala.1304 | 5-CF₃ | H | 3-Cl | —S— | 3-chlorophenyl |
| I.Ala.1305 | 5-CF₃ | H | 3-Cl | —S— | 4-chlorophenyl |
| I.Ala.1306 | 5-CF₃ | H | 3-Cl | —S— | 2,3-dichlorophenyl |
| I.Ala.1307 | 5-CF₃ | H | 3-Cl | —S— | 2,5-dichlorophenyl |
| I.Ala.1308 | 5-CF₃ | H | 3-Cl | —S— | 3,5-dichlorophenyl |
| I.Ala.1309 | 5-CF₃ | H | 3-Cl | —S— | 2,4-dichlorophenyl |
| I.Ala.1310 | 5-CF₃ | H | 3-Cl | —S— | 2,6-dichlorophenyl |

TABLE B-continued

| No. | R¹ | R² | R³ | X | Q |
|---|---|---|---|---|---|
| I.Ala.1311 | 5-CF₃ | H | 3-Cl | —S— | 2-fluorophenyl |
| I.Ala.1312 | 5-CF₃ | H | 3-Cl | —S— | 3-fluorophenyl |
| I.Ala.1313 | 5-CF₃ | H | 3-Cl | —S— | 4-fluorophenyl |
| I.Ala.1314 | 5-CF₃ | H | 3-Cl | —S— | 2,3-difluorophenyl |
| I.Ala.1315 | 5-CF₃ | H | 3-Cl | —S— | 3,5-difluorophenyl |
| I.Ala.1316 | 5-CF₃ | H | 3-Cl | —S— | 2-methylphenyl |
| I.Ala.1317 | 5-CF₃ | H | 3-Cl | —S— | 3-methylphenyl |
| I.Ala.1318 | 5-CF₃ | H | 3-Cl | —S— | 4-methylphenyl |
| I.Ala.1319 | 5-CF₃ | H | 3-Cl | —S— | 2,3-dimethylphenyl |
| I.Ala.1320 | 5-CF₃ | H | 3-Cl | —S— | 3,5-dimethylphenyl |
| I.Ala.1321 | 5-CF₃ | H | 3-Cl | —S— | 2-methoxyphenyl |
| I.Ala.1322 | 5-CF₃ | H | 3-Cl | —S— | 3-methoxyphenyl |
| I.Ala.1323 | 5-CF₃ | H | 3-Cl | —S— | 4-methoxyphenyl |
| I.Ala.1324 | 5-CF₃ | H | 3-Cl | —S— | 2,3-dimethoxyphenyl |
| I.Ala.1325 | 5-CF₃ | H | 3-Cl | —S— | 3,5-dimethoxyphenyl |
| I.Ala.1326 | 5-CF₃ | H | 3-Cl | —S— | 2,5-dimethoxyphenyl |
| I.Ala.1327 | 5-CF₃ | H | 3-Cl | —S— | 3-isopropylphenyl |
| I.Ala.1328 | 5-CF₃ | H | 3-Cl | —S— | 3-(n-butyl)phenyl |
| I.Ala.1329 | 5-CF₃ | H | 3-Cl | —S— | 3-phenylphenyl |
| I.Ala.1330 | 5-CF₃ | H | 3-Cl | —S— | 3-(trifluoromethyl)phenyl |
| I.Ala.1331 | 5-CF₃ | H | 3-Cl | —S— | 3-nitrophenyl |
| I.Ala.1332 | 5-CF₃ | H | 3-Cl | —S— | 3-bromophenyl |
| I.Ala.1333 | 5-CF₃ | H | 3-Cl | —S— | 2,3-dichlorophenyl |
| I.Ala.1334 | 5-CF₃ | H | 3-Cl | —S— | 3-cyanophenyl |
| I.Ala.1335 | 5-CF₃ | H | 3-Cl | —S— | 3-(phenoxy)phenyl |
| I.Ala.1336 | 5-CF₃ | H | 3-Cl | —S— | 3-(trichloromethyl)phenyl |
| I.Ala.1337 | 5-CF₃ | H | 3-Cl | —S— | 3-ethylphenyl |
| I.Ala.1338 | 5-CF₃ | H | 3-Cl | —S— | 3-(trichloromethoxy)phenyl |
| I.Ala.1339 | 5-CF₃ | H | 3-Cl | —S— | 3-(chlorodifluoromethyl)-phenyl |
| I.Ala.1340 | 5-CF₃ | H | 3-Cl | —S— | 3-(methylcarbonyl)phenyl |
| I.Ala.1341 | 5-CF₃ | H | 3-Cl | —S— | 3-(methylsulfonyl)phenyl |
| I.Ala.1342 | 5-CF₃ | H | 3-Cl | —S— | 3-(chloromethyl)phenyl |
| I.Ala.1343 | 5-CF₃ | H | 3-Cl | —S— | 5-chloro-2-methoxyphenyl |
| I.Ala.1344 | 5-CF₃ | H | 3-Cl | —S— | 3-(benzyloxy)phenyl |
| I.Ala.1345 | 5-Cl | H | 3-CF₃ | —S— | phenyl |
| I.Ala.1346 | 5-Cl | H | 3-CF₃ | —S— | 2-chlorophenyl |
| I.Ala.1347 | 5-Cl | H | 3-CF₃ | —S— | 3-chlorophenyl |
| I.Ala.1348 | 5-Cl | H | 3-CF₃ | —S— | 4-chlorophenyl |
| I.Ala.1349 | 5-Cl | H | 3-CF₃ | —S— | 2,3-dichlorophenyl |
| I.Ala.1350 | 5-Cl | H | 3-CF₃ | —S— | 2,5-dichlorophenyl |
| I.Ala.1351 | 5-Cl | H | 3-CF₃ | —S— | 3,5-dichlorophenyl |
| I.Ala.1352 | 5-Cl | H | 3-CF₃ | —S— | 2,4-dichlorophenyl |
| I.Ala.1353 | 5-Cl | H | 3-CF₃ | —S— | 2,6-dichlorophenyl |
| I.Ala.1354 | 5-Cl | H | 3-CF₃ | —S— | 2-fluorophenyl |
| I.Ala.1355 | 5-Cl | H | 3-CF₃ | —S— | 3-fluorophenyl |
| I.Ala.1356 | 5-Cl | H | 3-CF₃ | —S— | 4-fluorophenyl |
| I.Ala.1357 | 5-Cl | H | 3-CF₃ | —S— | 2,3-difluorophenyl |
| I.Ala.1358 | 5-Cl | H | 3-CF₃ | —S— | 3,5-difluorophenyl |
| I.Ala.1359 | 5-Cl | H | 3-CF₃ | —S— | 2-methylphenyl |
| I.Ala.1360 | 5-Cl | H | 3-CF₃ | —S— | 3-methylphenyl |
| I.Ala.1361 | 5-Cl | H | 3-CF₃ | —S— | 4-methylphenyl |
| I.Ala.1362 | 5-Cl | H | 3-CF₃ | —S— | 2,3-dimethylphenyl |
| I.Ala.1363 | 5-Cl | H | 3-CF₃ | —S— | 3,5-dimethylphenyl |
| I.Ala.1364 | 5-Cl | H | 3-CF₃ | —S— | 2-methoxyphenyl |
| I.Ala.1365 | 5-Cl | H | 3-CF₃ | —S— | 3-methoxyphenyl |
| I.Ala.1366 | 5-Cl | H | 3-CF₃ | —S— | 4-methoxyphenyl |
| I.Ala.1367 | 5-Cl | H | 3-CF₃ | —S— | 2,3-dimethoxyphenyl |
| I.Ala.1368 | 5-Cl | H | 3-CF₃ | —S— | 3,5-dimethoxyphenyl |
| I.Ala.1369 | 5-Cl | H | 3-CF₃ | —S— | 2,5-dimethoxyphenyl |
| I.Ala.1370 | 5-Cl | H | 3-CF₃ | —S— | 3-isopropylphenyl |
| I.Ala.1371 | 5-Cl | H | 3-CF₃ | —S— | 3-(n-butyl)phenyl |
| I.Ala.1372 | 5-Cl | H | 3-CF₃ | —S— | 3-phenylphenyl |
| I.Ala.1373 | 5-Cl | H | 3-CF₃ | —S— | 3-(trifluoromethyl)phenyl |
| I.Ala.1374 | 5-Cl | H | 3-CF₃ | —S— | 3-nitrophenyl |
| I.Ala.1375 | 5-Cl | H | 3-CF₃ | —S— | 3-broniophenyl |
| I.Ala.1376 | 5-Cl | H | 3-CF₃ | —S— | 2,3-dichlorophenyl |
| I.Ala.1377 | 5-Cl | H | 3-CF₃ | —S— | 3-cyanophenyl |
| I.Ala.1378 | 5-Cl | H | 3-CF₃ | —S— | 3-(phenoxy)phenyl |
| I.Ala.1379 | 5-Cl | H | 3-CF₃ | —S— | 3-(trichloromethyl)phenyl |
| I.Ala.1380 | 5-Cl | H | 3-CF₃ | —S— | 3-ethylphenyl |
| I.Ala.1381 | 5-Cl | H | 3-CF₃ | —S— | 3-(trichloromethoxy)phenyl |
| I.Ala.1382 | 5-Cl | H | 3-CF₃ | —S— | 3-(chlorodifluoromethyl)-phenyl |
| I.Ala.1383 | 5-Cl | H | 3-CF₃ | —S— | 3-(methylcarbonyl)phenyl |
| I.Ala.1384 | 5-Cl | H | 3-CF₃ | —S— | 3-(methylsulfonyl)phenyl |
| I.Ala.1385 | 5-Cl | H | 3-CF₃ | —S— | 3-(chloromethyl)phenyl |

TABLE B-continued

| No. | R¹ | R² | R³ | X | Q |
|---|---|---|---|---|---|
| I.Ala.1386 | 5-Cl | H | 3-CF₃ | —S— | 5-chloro-2-methylphenyl |
| I.Ala.1387 | 5-Cl | H | 3-CF₃ | —S— | 3-(benzyloxy)phenyl |
| I.Ala.1388 | 6-Cl | H | H | —S— | phenyl |
| I.Ala.1389 | 6-Cl | H | H | —S— | 3-chlorophenyl |
| I.Ala.1390 | 6-Cl | H | H | —S— | 2,3-dichlorophenyl |
| I.Ala.1391 | 6-Cl | H | H | —S— | 2,5-dichlorophenyl |
| I.Ala.1392 | 6-Cl | H | H | —S— | 3,5-dichlorophenyl |
| I.Ala.1393 | 6-Cl | H | H | —S— | 3-fluorophenyl |
| I.Ala.1394 | 6-Cl | H | H | —S— | 2,3-difluorophenyl |
| I.Ala.1395 | 6-Cl | H | H | —S— | 3,5-difluorophenyl |
| I.Ala.1396 | 6-Cl | H | H | —S— | 3-methylphenyl |
| I.Ala.1397 | 6-Cl | H | H | —S— | 2,3-dimethylphenyl |
| I.Ala.1398 | 6-Cl | H | H | —S— | 3,5-dimethylphenyl |
| I.Ala.1399 | 6-Cl | H | H | —S— | 3-methoxyphenyl |
| I.Ala.1400 | 6-Cl | H | H | —S— | 2,3-dimethoxyphenyl |
| I.Ala.1401 | 6-Cl | H | H | —S— | 3,5-dimethoxyphenyl |
| I.Ala.1402 | 6-Cl | H | H | —S— | 2,5-dimethoxyphenyl |
| I.Ala.1403 | 6-Cl | H | H | —S— | 3-isopropylphenyl |
| I.Ala.1404 | 6-Cl | H | H | —S— | 3-(n-butyl)phenyl |
| I.Ala.1405 | 6-Cl | H | H | —S— | 3-phenylphenyl |
| I.Ala.1406 | 6-Cl | H | H | —S— | 3-(trifluoromethyl)phenyl |
| I.Ala.1407 | 6-Cl | H | H | —S— | 3-nitrophenyl |
| I.Ala.1408 | 6-Cl | H | H | —S— | 3-bromophenyl |
| I.Ala.1409 | 6-Cl | H | H | —S— | 2,3-dichlorophenyl |
| I.Ala.1410 | 6-Cl | H | H | —S— | 3-cyanophenyl |
| I.Ala.1411 | 6-Cl | H | H | —S— | 3-(phenoxy)phenyl |
| I.Ala.1412 | 6-Cl | H | H | —S— | 3-(trichloromethyl)phenyl |
| I.Ala.1413 | 6-Cl | H | H | —S— | 3-ethylphenyl |
| I.Ala.1414 | 6-Cl | H | H | —S— | 3-(trichloromethoxy)phenyl |
| I.Ala.1415 | 6-Cl | H | H | —S— | 3-(chlorodifluoromethyl)-phenyl |
| I.Ala.1416 | 6-Cl | H | H | —S— | 3-(methylcarbonyl)phenyl |
| I.Ala.1417 | 6-CF₃ | H | H | —S— | phenyl |
| I.Ala.1418 | 6-CF₃ | H | H | —S— | 3-chlorophenyl |
| I.Ala.1419 | 6-CF₃ | H | H | —S— | 3,5-dichlorophenyl |
| I.Ala.1420 | 6-CF₃ | H | H | —S— | 3-fluorophenyl |
| I.Ala.1421 | 6-CF₃ | H | H | —S— | 3-methylphenyl |
| I.Ala.1422 | 6-CF₃ | H | H | —S— | 2,3-dimethylphenyl |
| I.Ala.1423 | 6-CF₃ | H | H | —S— | 3,5-dimethylphenyl |
| I.Ala.1424 | 6-CF₃ | H | H | —S— | 3-methoxyphenyl |
| I.Ala.1425 | 6-CF₃ | H | H | —S— | 2,3-dimethoxyphenyl |
| I.Ala.1426 | 6-CF₃ | H | H | —S— | 3-isopropylphenyl |
| I.Ala.1427 | 6-CF₃ | H | H | —S— | 3-phenylphenyl |
| I.Ala.1428 | 6-CF₃ | H | H | —S— | 3-(trifluoromethyl)phenyl |
| I.Ala.1429 | 6-CF₃ | H | H | —S— | 3-nitrophenyl |
| I.Ala.1430 | 6-CF₃ | H | H | —S— | 3-bromophenyl |
| I.Ala.1431 | 6-CF₃ | H | H | —S— | 3-cyanophenyl |
| I.Ala.1432 | 6-CF₃ | H | H | —S— | 3-(phenoxy)phenyl |
| I.Ala.1433 | H | 4-CF₃ | H | —S— | phenyl |
| I.Ala.1434 | H | 4-CF₃ | H | —S— | 3-chlorophenyl |
| I.Ala.1435 | H | 4-CF₃ | H | —S— | 3,5-dichlorophenyl |
| I.Ala.1436 | H | 4-CF₃ | H | —S— | 3-fluorophenyl |
| I.Ala.1437 | H | 4-CF₃ | H | —S— | 3-methylphenyl |
| I.Ala.1438 | H | 4-CF₃ | H | —S— | 2,3-dimethylphenyl |
| I.Ala.1439 | H | 4-CF₃ | H | —S— | 3,5-dimethylphenyl |
| I.Ala.1440 | H | 4-CF₃ | H | —S— | 3-methoxyphenyl |
| I.Ala.1441 | H | 4-CF₃ | H | —S— | 2,3-dimethoxyphenyl |
| I.Ala.1442 | H | 4-CF₃ | H | —S— | 3-isopropylphenyl |
| I.Ala.1443 | H | 4-CF₃ | H | —S— | 3-phenylphenyl |
| I.Ala.1444 | H | 4-CF₃ | H | —S— | 3-(trifluoromethyl)phenyl |
| I.Ala.1445 | M | 4-CF₃ | H | —S— | 3-nitrophenyl |
| I.Ala.1446 | H | 4-CF₃ | H | —S— | 3-bromophenyl |
| I.Ala.1447 | H | 4-CF₃ | H | —S— | 3-cyanophenyl |
| I.Ala.1448 | H | 4-CF₃ | H | —S— | 3-(phenoxy)phenyl |
| I.Ala.1449 | H | H | 3-NO₂ | —S— | phenyl |
| I.Ala.1450 | H | H | 3-NO₂ | —S— | 3-chlorophenyl |
| I.Ala.1451 | H | H | 3-NO₂ | —S— | 3,5-dichlorophenyl |
| I.Ala.1452 | H | H | 3-NO₂ | —S— | 3-fluorophenyl |
| I.Ala.1453 | H | H | 3-NO₂ | —S— | 3-methylphenyl |
| I.Ala.1454 | H | H | 3-NO₂ | —S— | 2,3-dimethylphenyl |
| I.Ala.1455 | H | H | 3-NO₂ | —S— | 3,5-dimethylphenyl |
| I.Ala.1456 | H | H | 3-NO₂ | —S— | 3-methoxyphenyl |
| I.Ala.1457 | H | H | 3-No2 | —S— | 2,3-dimethoxyphenyl |
| I.Ala.1458 | H | H | 3-NO₂ | —S— | 3-isopropylphenyl |
| I.Ala.1459 | H | H | 3-NO₂ | —S— | 3-phenylphenyl |
| I.Ala.1460 | H | H | 3-NO₂ | —S— | 3-(trifluoromethyl)phenyl |
| I.Ala.1461 | H | H | 3-NO₂ | —S— | 3-nitrophenyl |

TABLE B-continued

| No. | R¹ | R² | R³ | X | Q |
|---|---|---|---|---|---|
| I.Ala.1462 | H | H | 3-NO₂ | —S— | 3-bromophenyl |
| I.Ala.1463 | H | H | 3-NO₂ | —S— | 3-cyanophenyl |
| I.Ala.1464 | H | H | 3-NO₂ | —S— | 3-(phenoxy)phenyl |
| I.Ala.1465 | 6-Cl | 5-CF₃ | H | —S— | phenyl |
| I.Ala.1466 | 6-Cl | 5-CF₃ | H | —S— | 3-chlorophenyl |
| I.Ala.1467 | 6-Cl | 5-CF₃ | H | —S— | 3-fluorophenyl |
| I.Ala.1468 | 6-Cl | 5-CF₃ | H | —S— | 3-methylphenyl |
| I.Ala.1469 | 6-Cl | 5-CF₃ | H | —S— | 3-methoxyphenyl |
| I.Ala.1470 | 6-Cl | 5-CF₃ | H | —S— | 3-phenylphenyl |
| I.Ala.1471 | 6-Cl | 5-CF₃ | H | —S— | 3-(trifluoromethyl)phenyl |
| I.Ala.1472 | 6-Cl | 5-CF₃ | H | —S— | 3-nitrophenyl |
| I.Ala.1473 | 6-Cl | 5-CF₃ | H | —S— | 3-cyanophenyl |
| I.Ala.1474 | H | 5-CF₃ | 3-CN | —S— | phenyl |
| I.Ala.1475 | H | 5-CF₃ | 3-CN | —S— | 3-chlorophenyl |
| I.Ala.1476 | H | 5-CF₃ | 3-CN | —S— | 3-fluorophenyl |
| I.Ala.1477 | H | 5-CF₃ | 3-CN | —S— | 3-methylphenyl |
| I.Ala.1478 | H | 5-CF₃ | 3-CN | —S— | 3-methoxyphenyl |
| I.Ala.1479 | H | 5-CF₃ | 3-CN | —S— | 3-phenylphenyl |
| I.Ala.1480 | H | 5-CF₃ | 3-CN | —S— | 3-(trifluoromethyl)phenyl |
| I.AIa.1481 | H | 5-CF₃ | 3-CN | —S— | 3-nitrophenyl |
| I.Ala.1482 | H | 5-CF₃ | 3-CN | —S— | 3-cyanophenyl |
| I.Ala.1483 | 6-Cl | 4-CF₃ | H | —S— | phenyl |
| I.Ala.1484 | 6-Cl | 4-CF₃ | H | —S— | 3-chlorophenyl |
| I.Ala.1485 | 6-Cl | 4-CF₃ | H | —S— | 3-fluorophenyl |
| I.Ala.1486 | 6-Cl | 4-CF₃ | H | —S— | 3-methylphenyl |
| I.Ala.1487 | 6-Cl | 4-CF₃ | H | —S— | 3-methoxyphenyl |
| I.Ala.1488 | 6-Cl | 4-CF₃ | H | —S— | 3-phenylphenyl |
| I.Ala.1489 | 6-Cl | 4-CF₃ | H | —S— | 3-(trifluoromethyl)phenyl |
| I.Ala.1490 | 6-Cl | 4-CF₃ | H | —S— | 3-nitrophenyl |
| I.Ala.1491 | 6-Cl | 4-CF₃ | H | —S— | 3-cyanophenyl |
| I.Ala.1492 | 6-Cl | H | 3-CN | —S— | phenyl |
| I.Ala.1493 | 6-Cl | H | 3-CN | —S— | 3-chlorophenyl |
| I.Ala.1494 | 6-Cl | H | 3-CN | —S— | 3-fluorophenyl |
| I.Ala.1495 | 6-Cl | H | 3-CN | —S— | 3-methylphenyl |
| I.Ala.1496 | 6-Cl | H | 3-CN | —S— | 3-methoxyphenyl |
| I.Ala.1497 | 6-Cl | H | 3-CN | —S— | 3-phenylphenyl |
| I.Ala.1498 | 6-Cl | H | 3-CN | —S— | 3-(trifluoromethyl)phenyl |
| I.Ala.1499 | 6-Cl | H | 3-CN | —S— | 3-nitrophenyl |
| I.Ala.1500 | 6-Cl | H | 3-CN | —S— | 3-cyanophenyl |
| I.Ala.1501 | 6-CH₃ | 4-CH₃ | 3-CN | —S— | phenyl |
| I.Ala.1502 | 6-CH₃ | 4-CH₃ | 3-CN | —S— | 3-chlorophenyl |
| I.Ala.1503 | 6-CH₃ | 4-CH₃ | 3-CN | —S— | 3-fluorophenyl |
| I.Ala.1504 | 6-CH₃ | 4-CH₃ | 3-CN | —S— | 3-methylphenyl |
| I.Ala.1505 | 6-CH₃ | 4-CH₃ | 3-CN | —S— | 3-methoxyphenyl |
| I.Ala.1506 | 6-CH₃ | 4-CH₃ | 3-CN | —S— | 3-phenylphenyl |
| I.Ala.1507 | 6-CH₃ | 4-CH₃ | 3-CN | —S— | 3-(trifluoromethyl)phenyl |
| I.Ala.1508 | 6-CH₃ | 4-CH₃ | 3-CN | —S— | 3-nitrophenyl |
| I.Ala.1509 | 6-CH₃ | 4-CH₃ | 3-CN | —S— | 3-cyanophenyl |
| I.Ala.1510 | 5-CF₃ | H | 3-Cl | —O— | 3,4-dichlorophenyl |
| I.Ala.1511 | 6-Cl | H | 3-NO₂ | —O— | 3-chlorophenyl |
| I.Ala.1512 | 6-Cl | 5-NO₂ | H | —O— | 3-chlorophenyl |
| I.Ala.1513 | 6-Cl | 5-CN | H | —O— | 3-chlorophenyl |

TABLE C

| No. | R¹ | R² | R³ | X | Q |
|---|---|---|---|---|---|
| I.A1a.2001 | H | H | H | —NH— | phenyl |
| I.A1a.2002 | H | H | H | —NH— | 2-chlorophenyl |
| I.A1a.2003 | H | H | H | —NH— | 3-chlorophenyl |
| I.A1a.2004 | H | H | H | —NH— | 4-chlorophenyl |
| I.A1a.2005 | H | H | H | —NH— | 2,3-dichlorophenyl |
| I.A1a.2006 | H | H | H | —NH— | 2,5-dichlorophenyl |
| I.A1a.2007 | H | H | H | —NH— | 3,5-dichlorophenyl |
| I.A1a.2008 | H | H | H | —NH— | 2,4-dichlorophenyl |
| I.A1a.2009 | H | H | H | —NH— | 2,6-dichlorophenyl |
| I.A1a.2010 | H | H | H | —NH— | 2-fluorophenyl |
| I.A1a.2011 | H | H | H | —NH— | 3-fluorophenyl |
| I.A1a.2012 | H | H | H | —NH— | 4-fluorophenyl |
| I.A1a.2013 | H | H | H | —NH— | 2,3-difluorophenyl |
| I.A1a.2014 | H | H | H | —NH— | 3,5-difluorophenyl |
| I.A1a.2015 | H | H | H | —NH— | 2-methylphenyl |
| I.A1a.2016 | H | H | H | —NH— | 3-methylphenyl |
| I.A1a.2017 | H | H | H | —NH— | 4-methylphenyl |
| I.A1a.2018 | H | H | H | —NH— | 2,3-dimethylphenyl |
| I.A1a.2019 | H | H | H | —NH— | 3,5-dimethylphenyl |
| I.A1a.2020 | H | H | H | —NH— | 2-methoxyphenyl |
| I.A1a.2021 | H | H | H | —NH— | 3-methoxyphenyl |
| I.A1a.2022 | H | H | H | —NH— | 4-methoxyphenyl |
| I.A1a.2023 | H | H | H | —NH— | 2,3-dimethoxy- |

TABLE C-continued

| No. | R¹ | R² | R³ | X | Q |
|---|---|---|---|---|---|
| I.A1a.2024 | H | H | H | —NH— | 3,5-dimethoxyphenyl |
| I.A1a.2025 | H | H | H | —NH— | 2,5-dimethoxyphenyl |
| I.A1a.2026 | H | H | H | —NH— | 3-isopropylphenyl |
| I.A1a.2027 | H | H | H | —NH— | 3-(n-butyl)phenyl |
| I.A1a.2028 | H | H | H | —NH— | 3-phenylphenyl |
| I.A1a.2029 | H | H | H | —NH— | 3-trifluoromethylphenyl |
| I.A1a.2030 | H | H | H | —NH— | 3-nitrophenyl |
| I.A1a.2031 | H | H | H | —NH— | 3-bromophenyl |
| I.A1a.2032 | H | H | H | —NH— | 2,3-dichlorophenyl |
| I.A1a.2033 | H | H | H | —NH— | 3-cyanophenyl |
| I.A1a.2034 | H | H | H | —NH— | 3-phenoxyphenyl |
| I.A1a.2035 | H | H | H | —NH— | 3-(trichloromethyl)phenyl |
| I.A1a.2036 | H | H | H | —NH— | 3-ethylphenyl |
| I.A1a.2037 | H | H | H | —NH— | 3-(trichloromethoxy)phenyl |
| I.A1a.2038 | H | H | H | —NH— | 3-(chlorodifluoromethyl)phenyl |
| I.A1a.2039 | H | H | H | —NH— | 3-(methylcarbonyl)phenyl |
| I.A1a.2040 | H | H | H | —NH— | 3-(methylsulfonyl)phenyl |
| I.A1a.2041 | H | H | H | —NH— | 3-(chloromethyl)phenyl |
| I.A1a.2042 | H | H | H | —NH— | 5-chloro-2-methoxyphenyl |
| I.A1a.2043 | H | H | H | —NH— | 3-(benzyloxy)phenyl |
| I.A1a.2044 | H | H | 3-Cl | —NH— | phenyl |
| I.A1a.2045 | H | H | 3-Cl | —NH— | 2-chlorophenyl |
| I.A1a.2046 | H | H | 3-Cl | —NH— | 3-chlorophenyl |
| I.A1a.2047 | H | H | 3-Cl | —NH— | 4-chlorophenyl |
| I.A1a.2048 | H | H | 3-Cl | —NH— | 2,3-dichlorophenyl |
| I.A1a.2049 | H | H | 3-Cl | —NH— | 2,5-dichlorophenyl |
| I.A1a.2050 | H | H | 3-Cl | —NH— | 3,5-dichlorophenyl |
| I.A1a.2051 | H | H | 3-Cl | —NH— | 2,4-dichlorophenyl |
| I.A1a.2052 | H | H | 3-Cl | —NH— | 2,6-dichlorophenyl |
| I.A1a.2053 | H | H | 3-Cl | —NH— | 2-fluorophenyl |
| I.A1a.2054 | H | H | 3-Cl | —NH— | 3-fluorophenyl |
| I.A1a.2055 | H | H | 3-Cl | —NH— | 4-fluorophenyl |
| I.A1a.2056 | H | H | 3-Cl | —NH— | 2,3-difluorophenyl |
| I.A1a.2057 | H | H | 3-Cl | —NH— | 3,5-difluorophenyl |
| I.A1a.2058 | H | H | 3-Cl | —NH— | 2-methylphenyl |
| I.A1a.2059 | H | H | 3-Cl | —NH— | 3-methylphenyl |
| I.A1a.2060 | H | H | 3-Cl | —NH— | 4-methylphenyl |
| I.A1a.2061 | H | H | 3-Cl | —NH— | 2,3-dimethylphenyl |
| I.A1a.2062 | H | H | 3-Cl | —NH— | 3,5-dimethylphenyl |
| I.A1a.2063 | H | H | 3-Cl | —NH— | 2-methoxyphenyl |
| I.A1a.2064 | H | H | 3-Cl | —NH— | 3-methoxyphenyl |
| I.A1a.2065 | H | H | 3-Cl | —NH— | 4-methoxyphenyl |
| I.A1a.2066 | H | H | 3-Cl | —NH— | 2,3-dimethoxyphenyl |
| I.A1a.2067 | H | H | 3-Cl | —NH— | 3,5-dimethoxyphenyl |
| I.A1a.2068 | H | H | 3-Cl | —NH— | 2,5-dimethoxyphenyl |
| I.A1a.2069 | H | H | 3-Cl | —NH— | 3-isopropylphenyl |
| I.A1a.2070 | H | H | 3-Cl | —NH— | 3-(n-butyl)phenyl |
| I.A1a.2071 | H | H | 3-Cl | —NH— | 3-phenylphenyl |
| I.A1a.2072 | H | H | 3-Cl | —NH— | 3-(trifluoromethyl)phenyl |
| I.A1a.2073 | H | H | 3-Cl | —NH— | 3-nitrophenyl |
| I.A1a.2074 | H | H | 3-Cl | —NH— | 3-bromophenyl |
| I.A1a.2075 | H | H | 3-Cl | —NH— | 2,3-dichlorophenyl |
| I.A1a.2076 | H | H | 3-Cl | —NH— | 3-cyanophenyl |
| I.A1a.2077 | H | H | 3-Cl | —NH— | 3-phenyloxyphenyl |
| I.A1a.2078 | H | H | 3-Cl | —NH— | 3-trichloromethylphenyl |
| I.A1a.2079 | H | H | 3-Cl | —NH— | 3-ethylphenyl |
| I.A1a.2080 | H | H | 3-Cl | —NH— | 3-(trichloromethoxy)phenyl |
| I.A1a.2081 | H | H | 3-Cl | —NH— | 3-(chlorodifluoromethyl)phenyl |
| I.A1a.2082 | H | H | 3-Cl | —NH— | 3-(methylcarbonyl)phenyl |
| I.A1a.2083 | H | H | 3-Cl | —NH— | 3-(methylsulfonyl)phenyl |
| I.A1a.2084 | H | H | 3-Cl | —NH— | 3-(chloromethyl)phenyl |
| I.A1a.2085 | H | H | 3-Cl | —NH— | 5-chloro-2-methoxyphenyl |
| I.A1a.2086 | H | H | 3-Cl | —NH— | 3-benzyloxyphenyl |
| I.A1a.2087 | H | H | 3-CF₃ | —NH— | phenyl |
| I.A1a.2088 | H | H | 3-CF₃ | —NH— | 2-chlorophenyl |
| I.A1a.2089 | H | H | 3-CF₃ | —NH— | 3-chlorophenyl |
| I.A1a.2090 | H | H | 3-CF₃ | —NH— | 4-chlorophenyl |
| I.A1a.2091 | H | H | 3-CF₃ | —NH— | 2,3-dichlorophenyl |
| I.A1a.2092 | H | H | 3-CF₃ | —NH— | 2,5-dichlorophenyl |
| I.A1a.2093 | H | H | 3-CF₃ | —NH— | 3,5-dichlorophenyl |
| I.A1a.2094 | H | H | 3-CF₃ | —NH— | 2,4-dichlorophenyl |
| I.A1a.2095 | H | H | 3-CF₃ | —NH— | 2,6-dichlorophenyl |
| I.A1a.2096 | H | H | 3-CF₃ | —NH— | 2-fluorophenyl |
| I.A1a.2097 | H | H | 3-CF₃ | —NH— | 3-fluorophenyl |
| I.A1a.2098 | H | H | 3-CF₃ | —NH— | 4-fluorophenyl |
| I.A1a.2099 | H | H | 3-CF₃ | —NH— | 2,3-difluorophenyl |
| I.A1a.2100 | H | H | 3-CF₃ | —NH— | 3,5-difluorophenyl |
| I.A1a.2101 | H | H | 3-CF₃ | —NH— | 2-methylphenyl |
| I.A1a.2102 | H | H | 3-CF₃ | —NH— | 3-methylphenyl |
| I.A1a.2103 | H | H | 3-CF₃ | —NH— | 4-methylphenyl |
| I.A1a.2104 | H | H | 3-CF₃ | —NH— | 2,3-dimethylphenyl |
| I.A1a.2105 | H | H | 3-CF₃ | —NH— | 3,5-dimethylphenyl |
| I.A1a.2106 | H | H | 3-CF₃ | —NH— | 2-methoxyphenyl |
| I.A1a.2107 | H | H | 3-CF₃ | —NH— | 3-methoxyphenyl |
| I.A1a.2108 | H | H | 3-CF₃ | —NH— | 4-methoxyphenyl |
| I.A1a.2109 | H | H | 3-CF₃ | —NH— | 2,3-dimethoxyphenyl |
| I.A1a.2110 | H | H | 3-CF₃ | —NH— | 3,5-dimethoxyphenyl |
| I.A1a.2111 | H | H | 3-CF₃ | —NH— | 2,5-dimethoxyphenyl |
| I.A1a.2112 | H | H | 3-CF₃ | —NH— | 3-isopropylphenyl |
| I.A1a.2113 | H | H | 3-CF₃ | —NH— | 3-(n-butyl)phenyl |
| I.A1a.2114 | H | H | 3-CF₃ | —NH— | 3-phenylphenyl |
| I.A1a.2115 | H | H | 3-CF₃ | —NH— | 3-(trifluoromethyl)phenyl |
| I.A1a.2116 | H | H | 3-CF₃ | —NH— | 3-nitrophenyl |
| I.A1a.2117 | H | H | 3-CF₃ | —NH— | 3-bromophenyl |
| I.A1a.2118 | H | H | 3-CF₃ | —NH— | 2,3-dichlorophenyl |
| I.A1a.2119 | H | H | 3-CF₃ | —NH— | 3-cyanophenyl |
| I.A1a.2120 | H | H | 3-CF₃ | —NH— | 3-phenoxyphenyl |
| I.A1a.2121 | H | H | 3-CF₃ | —NH— | 3-(trichloromethyl)phenyl |
| I.A1a.2122 | H | H | 3-CF₃ | —NH— | 3-ethylphenyl |
| I.A1a.2123 | H | H | 3-CF₃ | —NH— | 3-(trichloro- |

TABLE C-continued

| No. | R¹ | R² | R³ | X | Q |
|---|---|---|---|---|---|
| I.A1a.2124 | H | H | 3-CF₃ | —NH— | 3-(chlorodifluoro-methyl)phenyl |
| I.A1a.2125 | H | H | 3-CF₃ | —NH— | 3-(methyl-carbonyl)phenyl |
| I.A1a.2126 | H | H | 3-CF₃ | —NH— | 3-(methyl-sulfonyl)phenyl |
| I.A1a.2127 | H | H | 3-CF₃ | —NH— | 3-(chloro-methyl)phenyl |
| I.A1a.2128 | H | H | 3-CF₃ | —NH— | 5-chloro-2-methoxyphenyl |
| I.A1a.2129 | H | H | 3-CF₃ | —NH— | 3-(benzyl-oxy)phenyl |
| I.A1a.2130 | H | H | 3-CN | —NH— | phenyl |
| I.A1a.2131 | H | H | 3-CN | —NH— | 2-chlorophenyl |
| I.A1a.2132 | H | H | 3-CN | —NH— | 3-chlorophenyl |
| I.A1a.2133 | H | H | 3-CN | —NH— | 4-chlorophenyl |
| I.A1a.2134 | H | H | 3-CN | —NH— | 2,3-dichlorophenyl |
| I.A1a.2135 | H | H | 3-CN | —NH— | 2,5-dichlorophenyl |
| I.A1a.2136 | H | H | 3-CN | —NH— | 3,5-dichlorophenyl |
| I.A1a.2137 | H | H | 3-CN | —NH— | 2,4-dichlorophenyl |
| I.A1a.2138 | H | H | 3-CN | —NH— | 2,6-dichlorophenyl |
| I.A1a.2139 | H | H | 3-CN | —NH— | 2-fluorophenyl |
| I.A1a.2140 | H | H | 3-CN | —NH— | 3-fluorophenyl |
| I.A1a.2141 | H | H | 3-CN | —NH— | 4-fluorophenyl |
| I.A1a.2142 | H | H | 3-CN | —NH— | 2,3-difluorophenyl |
| I.A1a.2143 | H | H | 3-CN | —NH— | 3,5-difluorophenyl |
| I.A1a.2144 | H | H | 3-CN | —NH— | 2-methylphenyl |
| I.A1a.2145 | H | H | 3-CN | —NH— | 3-methylphenyl |
| I.A1a.2146 | H | H | 3-CN | —NH— | 4-methylphenyl |
| I.A1a.2147 | H | H | 3-CN | —NH— | 2,3-dimethylphenyl |
| I.A1a.2148 | H | H | 3-CN | —NH— | 3,5-dimethylphenyl |
| I.A1a.2149 | H | H | 3-CN | —NH— | 2-methoxyphenyl |
| I.A1a.2150 | H | H | 3-CN | —NH— | 3-methoxyphenyl |
| I.A1a.2151 | H | H | 3-CN | —NH— | 4-methoxyphenyl |
| I.A1a.2152 | H | H | 3-CN | —NH— | 2,3-dimethoxyphenyl |
| I.A1a.2153 | H | H | 3-CN | —NH— | 3,5-dimethoxyphenyl |
| I.A1a.2154 | H | H | 3-CN | —NH— | 2,5-dimethoxyphenyl |
| I.A1a.2155 | H | H | 3-CN | —NH— | 3-isopropyl-phenyl |
| I.A1a.2156 | H | H | 3-CN | —NH— | 3-(n-butyl)phenyl |
| I.A1a.2157 | H | H | 3-CN | —NH— | 3-phenylphenyl |
| I.A1a.2158 | H | H | 3-CN | —NH— | 3-(trifluoro-methyl)phenyl |
| I.A1a.2159 | H | H | 3-CN | —NH— | 3-nitrophenyl |
| I.A1a.2160 | H | H | 3-CN | —NH— | 3-bromophenyl |
| I.A1a.2161 | H | H | 3-CN | —NH— | 2,3-dichlorophenyl |
| I.A1a.2162 | H | H | 3-CN | —NH— | 3-cyanophenyl |
| I.A1a.2163 | H | H | 3-CN | —NH— | 3-phenoxyphenyl |
| I.A1a.2164 | H | H | 3-CN | —NH— | 3-(trichloro-methyl)phenyl |
| I.A1a.2165 | H | H | 3-CN | —NH— | 3-ethylphenyl |
| I.A1a.2166 | H | H | 3-CN | —NH— | 3-trichloro-methoxyphenyl |
| I.A1a.2167 | H | H | 3-CN | —NH— | 3-(chlorodi-fluoro)phenyl |
| I.A1a.2168 | H | H | 3-CN | —NH— | 3-(methyl-carbonyl)phenyl |
| I.A1a.2169 | H | H | 3-CN | —NH— | 3-(methylsul-fonyl)phenyl |
| I.A1a.2170 | H | H | 3-CN | —NH— | 3-(chloro-methyl)phenyl |
| I.A1a.2171 | H | H | 3-CN | —NH— | 5-chloro-2-methoxyphenyl |
| I.A1a.2172 | H | H | 3-CN | —NH— | 3-benzyloxy-phenyl |
| I.A1a.2173 | 5-Cl | H | H | —NH— | phenyl |
| I.A1a.2174 | 5-Cl | H | H | —NH— | 2-chloro |
| I.A1a.2175 | 5-Cl | H | H | —NH— | 3-chloro |
| I.A1a.2176 | 5-Cl | H | H | —NH— | 4-chloro |
| I.A1a.2177 | 5-Cl | H | H | —NH— | 2,3-dichlorophenyl |
| I.A1a.2178 | 5-Cl | H | H | —NH— | 2,5-dichlorophenyl |
| I.A1a.2179 | 5-Cl | H | H | —NH— | 3,5-dichlorophenyl |
| I.A1a.2180 | 5-Cl | H | H | —NH— | 2,4-dichlorophenyl |
| I.A1a.2181 | 5-Cl | H | H | —NH— | 2,6-dichlorophenyl |
| I.A1a.2182 | 5-Cl | H | H | —NH— | 2-fluorophenyl |
| I.A1a.2183 | 5-Cl | H | H | —NH— | 3-fluorophenyl |
| I.A1a.2184 | 5-Cl | H | H | —NH— | 4-fluorophenyl |
| I.A1a.2185 | 5-Cl | H | H | —NH— | 2,3-difluorophenyl |
| I.A1a.2186 | 5-Cl | H | H | —NH— | 3,5-difluorophenyl |
| I.A1a.2187 | 5-Cl | H | H | —NH— | 2-methylphenyl |
| I.A1a.2188 | 5-Cl | H | H | —NH— | 3-methylphenyl |
| I.A1a.2189 | 5-Cl | H | H | —NH— | 4-methylphenyl |
| I.A1a.2190 | 5-Cl | H | H | —NH— | 2,3-dimethylphenyl |
| I.A1a.2191 | 5-Cl | H | H | —NH— | 3,5-dimethylphenyl |
| I.A1a.2192 | 5-Cl | H | H | —NH— | 2-methoxyphenyl |
| I.A1a.2193 | 5-Cl | H | H | —NH— | 3-methoxyphenyl |
| I.A1a.2194 | 5-Cl | H | H | —NH— | 4-methoxyphenyl |
| I.A1a.2195 | 5-Cl | H | H | —NH— | 2,3-dimethoxyphenyl |
| I.A1a.2196 | 5-Cl | H | H | —NH— | 3,5-dimethoxyphenyl |
| I.A1a.2197 | 5-Cl | H | H | —NH— | 2,5-dimethoxyphenyl |
| I.A1a.2198 | 5-Cl | H | H | —NH— | 3-isopropylphenyl |
| I.A1a.2199 | 5-Cl | H | H | —NH— | 3-(n-butyl)phenyl |
| I.A1a.2200 | 5-Cl | H | H | —NH— | 3-(phenyl)phenyl |
| I.A1a.2201 | 5-Cl | H | H | —NH— | 3-(trifluoro-methyl)phenyl |
| I.A1a.2202 | 5-Cl | H | H | —NH— | 3-nitrophenyl |
| I.A1a.2203 | 5-Cl | H | H | —NH— | 3-bromophenyl |
| I.A1a.2204 | 5-Cl | H | H | —NH— | 2,3-dichlorophenyl |
| I.A1a.2205 | 5-Cl | H | H | —NH— | 3-cyanophenyl |
| I.A1a.2206 | 5-Cl | H | H | —NH— | 3-(phenoxy)phenyl |
| I.A1a.2207 | 5-Cl | H | H | —NH— | 3-(trichloro-methyl)phenyl |
| I.A1a.2208 | 5-Cl | H | H | —NH— | 3-ethylphenyl |
| I.A1a.2209 | 5-Cl | H | H | —NH— | 3-(trichloro-methoxy)phenyl |
| I.A1a.2210 | 5-Cl | H | H | —NH— | 3-(chlorodifluoro-methyl)phenyl |
| I.A1a.2211 | 5-Cl | H | H | —NH— | 3-(methyl-carbonyl)phenyl |
| I.A1a.2212 | 5-Cl | H | H | —NH— | 3-(methylsul-fonyl)phenyl |
| I.A1a.2213 | 5-Cl | H | H | —NH— | 3-(chloro-methyl)phenyl |
| I.A1a.2214 | 5-Cl | H | H | —NH— | 5-chloro-2-methoxyphenyl |
| I.A1a.2215 | 5-Cl | H | H | —NH— | 3-(benzyl-oxy)phenyl |
| I.A1a.2216 | 5-CF₃ | H | H | —NH— | phenyl |
| I.A1a.2217 | 5-CF₃ | H | H | —NH— | 2-chlorophenyl |
| I.A1a.2218 | 5-CF₃ | H | H | —NH— | 3-chlorophenyl |
| I.A1a.2219 | 5-CF₃ | H | H | —NH— | 4-chlorophenyl |
| I.A1a.2220 | 5-CF₃ | H | H | —NH— | 2,3-dichlorophenyl |
| I.A1a.2221 | 5-CF₃ | H | H | —NH— | 2,5-dichlorophenyl |
| I.A1a.2222 | 5-CF₃ | H | H | —NH— | 3,5-dichloro- |

TABLE C-continued

| No. | R¹ | R² | R³ | X | Q |
|---|---|---|---|---|---|
| I.A1a.2223 | 5-CF₃ | H | H | —NH— | 2,4-dichlorophenyl |
| I.A1a.2224 | 5-CF₃ | H | H | —NH— | 2,6-dichlorophenyl |
| I.A1a.2225 | 5-CF₃ | H | H | —NH— | 2-fluorophenyl |
| I.A1a.2226 | 5-CF₃ | H | H | —NH— | 3-fluorophenyl |
| I.A1a.2227 | 5-CF₃ | H | H | —NH— | 4-fluorophenyl |
| I.A1a.2228 | 5-CF₃ | H | H | —NH— | 2,3-difluorophenyl |
| I.A1a.2229 | 5-CF₃ | H | H | —NH— | 3,5-difluorophenyl |
| I.A1a.2230 | 5-CF₃ | H | H | —NH— | 2-methylphenyl |
| I.A1a.2231 | 5-CF₃ | H | H | —NH— | 3-methylphenyl |
| I.A1a.2232 | 5-CF₃ | H | H | —NH— | 4-methylphenyl |
| I.A1a.2233 | 5-CF₃ | H | H | —NH— | 2,3-dimethylphenyl |
| I.A1a.2234 | 5-CF₃ | H | H | —NH— | 3,5-dimethylphenyl |
| I.A1a.2235 | 5-CF₃ | H | H | —NH— | 2-methoxyphenyl |
| I.A1a.2236 | 5-CF₃ | H | H | —NH— | 3-methoxyphenyl |
| I.A1a.2237 | 5-CF₃ | H | H | —NH— | 4-methoxyphenyl |
| I.A1a.2238 | 5-CF₃ | H | H | —NH— | 2,3-dimethoxyphenyl |
| I.A1a.2239 | 5-CF₃ | H | H | —NH— | 3,5-dimethoxyphenyl |
| I.A1a.2240 | 5-CF₃ | H | H | —NH— | 2,5-dimethoxyphenyl |
| I.A1a.2241 | 5-CF₃ | H | H | —NH— | 3-isopropylphenyl |
| I.A1a.2242 | 5-CF₃ | H | H | —NH— | 3-(n-butyl)phenyl |
| I.A1a.2243 | 5-CF₃ | H | H | —NH— | 3-phenylphenyl |
| I.A1a.2244 | 5-CF₃ | H | H | —NH— | 3-(trifluoromethyl)phenyl |
| I.A1a.2245 | 5-CF₃ | H | H | —NH— | 3-nitrophenyl |
| I.A1a.2246 | 5-CF₃ | H | H | —NH— | 3-bromophenyl |
| I.A1a.2247 | 5-CF₃ | H | H | —NH— | 2,3-dichlorophenyl |
| I.A1a.2248 | 5-CF₃ | H | H | —NH— | 3-cyanophenyl |
| I.A1a.2249 | 5-CF₃ | H | H | —NH— | 3-(phenoxy)phenyl |
| I.A1a.2250 | 5-CF₃ | H | H | —NH— | 3-(trichloromethyl)phenyl |
| I.A1a.2251 | 5-CF₃ | H | H | —NH— | 3-ethylphenyl |
| I.A1a.2252 | 5-CF₃ | H | H | —NH— | 3-(trichloromethoxy)phenyl |
| I.A1a.2253 | 5-CF₃ | H | H | —NH— | 3-(chlorodifluoromethyl)phenyl |
| I.A1a.2254 | 5-CF₃ | H | H | —NH— | 3-(methylcarbonyl)phenyl |
| I.A1a.2255 | 5-CF₃ | H | H | —NH— | 3-(methylsulfonyl)phenyl |
| I.A1a.2256 | 5-CF₃ | H | H | —NH— | 3-(chloromethyl)phenyl |
| I.A1a.2257 | 5-CF₃ | H | H | —NH— | 5-chloro-2-methoxyphenyl |
| I.A1a.2258 | 5-CF₃ | H | H | —NH— | 3-(benzyloxy)phenyl |
| I.A1a.2259 | 5-CN | H | H | —NH— | phenyl |
| I.A1a.2260 | 5-CN | H | H | —NH— | 2-chlorophenyl |
| I.A1a.2261 | 5-CN | H | H | —NH— | 3-chlorophenyl |
| I.A1a.2262 | 5-CN | H | H | —NH— | 4-chlorophenyl |
| I.A1a.2263 | 5-CN | H | H | —NH— | 2,3-dichlorophenyl |
| I.A1a.2264 | 5-CN | H | H | —NH— | 2,5-dichlorophenyl |
| I.A1a.2265 | 5-CN | H | H | —NH— | 3,5-dichlorophenyl |
| I.A1a.2266 | 5-CN | H | H | —NH— | 2,4-dichlorophenyl |
| I.A1a.2267 | 5-CN | H | H | —NH— | 2,6-dichlorophenyl |
| I.A1a.2268 | 5-CN. | H | H | —NH— | 2-fluorophenyl |
| I.A1a.2269 | 5-CN | H | H | —NH— | 3-fluorophenyl |
| I.A1a.2270 | 5-CN | H | H | —NH— | 4-fluorophenyl |
| I.A1a.2271 | 5-CN | H | H | —NH— | 2,3-difluorophenyl |
| I.A1a.2272 | 5-CN | H | H | —NH— | 3,5-difluorophenyl |
| I.A1a.2273 | 5-CN | H | H | —NH— | 2-methylphenyl |
| I.A1a.2274 | 5-CN | H | H | —NH— | 3-methylphenyl |
| I.A1a.2275 | 5-CN | H | H | —NH— | 4-methylphenyl |
| I.A1a.2276 | 5-CN | H | H | —NH— | 2,3-dimethylphenyl |
| I.A1a.2277 | 5-CN | H | H | —NH— | 3,5-dimethylphenyl |
| I.A1a.2278 | 5-CN | H | H | —NH— | 2-methoxyphenyl |
| I.A1a.2279 | 5-CN | H | H | —NH— | 3-methoxyphenyl |
| I.A1a.2280 | 5-CN | H | H | —NH— | 4-methoxyphenyl |
| I.A1a.2281 | 5-CN | H | H | —NH— | 2,3-dimethoxyphenyl |
| I.A1a.2282 | 5-CN | H | H | —NH— | 3,5-dimethoxyphenyl |
| I.A1a.2283 | 5-CN | H | H | —NH— | 2,5-dimethoxyphenyl |
| I.A1a.2284 | 5-CN | H | H | —NH— | 3-isopropylphenyl |
| I.A1a.2285 | 5-CN | H | H | —NH— | 3-(n-butyl)phenyl |
| I.A1a.2286 | 5-CN | H | H | —NH— | 3-phenylphenyl |
| I.A1a.2287 | 5-CN | H | H | —NH— | 3-(trifluoromethyl)phenyl |
| I.A1a.2288 | 5-CN | H | H | —NH— | 3-nitrophenyl |
| I.A1a.2289 | 5-CN | H | H | —NH— | 3-bromophenyl |
| I.A1a.2290 | 5-CN | H | H | —NH— | 2,3-dichlorophenyl |
| I.A1a.2291 | 5-CN | H | H | —NH— | 3-cyanophenyl |
| I.A1a.2292 | 5-CN | H | H | —NH— | 3-(phenoxy)phenyl |
| I.A1a.2293 | 5-CN | H | H | —NH— | 3-(trichloromethyl)phenyl |
| I.A1a.2294 | 5-CN | H | H | —NH— | 3-ethylphenyl |
| I.A1a.2295 | 5-CN | H | H | —NH— | 3-(trichloromethoxy)phenyl |
| I.A1a.2296 | 5-CN | H | H | —NH— | 3-(chlorodifluoromethyl)phenyl |
| I.A1a.2297 | 5-CN | H | H | —NH— | 3-(methylcarbonyl)phenyl |
| I.A1a.2298 | 5-CN | H | H | —NH— | 3-(methylsulfonyl)phenyl |
| I.A1a.2299 | 5-CN | H | H | —NH— | 3-(chloromethyl)phenyl |
| I.A1a.2300 | 5-CN | H | H | —NH— | 5-chloro-2-methoxyphenyl |
| I.A1a.2301 | 5-CN | H | H | —NH— | 3-(benzyloxy)phenyl |
| I.A1a.2302 | 5-CF₃ | H | 3-Cl | —NH— | phenyl |
| I.A1a.2303 | 5-CF₃ | H | 3-Cl | —NH— | 2-chlorophenyl |
| I.A1a.2304 | 5-CF₃ | H | 3-Cl | —NH— | 3-chlorophenyl |
| I.A1a.2305 | 5-CF₃ | H | 3-Cl | —NH— | 4-chlorophenyl |
| I.A1a.2306 | 5-CF₃ | H | 3-Cl | —NH— | 2,3-dichlorophenyl |
| I.A1a.2307 | 5-CF₃ | H | 3-Cl | —NH— | 2,5-dichlorophenyl |
| I.A1a.2308 | 5-CF₃ | H | 3-Cl | —NH— | 3,5-dichlorophenyl |
| I.A1a.2309 | 5-CF₃ | H | 3-Cl | —NH— | 2,4-dichlorophenyl |
| I.A1a.2310 | 5-CF₃ | H | 3-Cl | —NH— | 2,6-dichlorophenyl |
| I.A1a.2311 | 5-CF₃ | H | 3-Cl | —NH— | 2-fluorophenyl |
| I.A1a.2312 | 5-CF₃ | H | 3-Cl | —NH— | 3-fluorophenyl |
| I.A1a.2313 | 5-CF₃ | H | 3-Cl | —NH— | 4-fluorophenyl |
| I.A1a.2314 | 5-CF₃ | H | 3-Cl | —NH— | 2,3-difluorophenyl |
| I.A1a.2315 | 5-CF₃ | H | 3-Cl | —NH— | 3,5-difluorophenyl |
| I.A1a.2316 | 5-CF₃ | H | 3-Cl | —NH— | 2-methylphenyl |
| I.A1a.2317 | 5-CF₃ | H | 3-Cl | —NH— | 3-methylphenyl |
| I.A1a.2318 | 5-CF₃ | H | 3-Cl | —NH— | 4-methylphenyl |
| I.A1a.2319 | 5-CF₃ | H | 3-Cl | —NH— | 2,3-dimethylphenyl |
| I.A1a.2320 | 5-CF₃ | H | 3-Cl | —NH— | 3,5-dimethylphenyl |
| I.A1a.2321 | 5-CF₃ | H | 3-Cl | —NH— | 2-methoxyphenyl |

TABLE C-continued

| No. | R¹ | R² | R³ | X | Q |
|---|---|---|---|---|---|
| I.A1a.2322 | 5-CF₃ | H | 3-Cl | —NH— | 3-methoxyphenyl |
| I.A1a.2323 | 5-CF₃ | H | 3-Cl | —NH— | 4-methoxyphenyl |
| I.A1a.2324 | 5-CF₃ | H | 3-Cl | —NH— | 2,3-dimethoxyphenyl |
| I.A1a.2325 | 5-CF₃ | H | 3-Cl | —NH— | 3,5-dimethoxyphenyl |
| I.A1a.2326 | 5-CF₃ | H | 3-Cl | —NH— | 2,5-dimethoxyphenyl |
| I.A1a.2327 | 5-CF₃ | H | 3-Cl | —NH— | 3-isopropylphenyl |
| I.A1a.2328 | 5-CF₃ | H | 3-Cl | —NH— | 3-(n-butyl)phenyl |
| I.A1a.2329 | 5-CF₃ | H | 3-Cl | —NH— | 3-phenylphenyl |
| I.A1a.2330 | 5-CF₃ | H | 3-Cl | —NH— | 3-(trifluoromethyl)phenyl |
| I.A1a.2331 | 5-CF₃ | H | 3-Cl | —NH— | 3-nitrophenyl |
| I.A1a.2332 | 5-CF₃ | H | 3-Cl | —NH— | 3-bromophenyl |
| I.A1a.2333 | 5-CF₃ | H | 3-Cl | —NH— | 2,3-dichlorophenyl |
| I.A1a.2334 | 5-CF₃ | H | 3-Cl | —NH— | 3-cyanophenyl |
| I.A1a.2335 | 5-CF₃ | H | 3-Cl | —NH— | 3-(phenoxy)phenyl |
| I.A1a.2336 | 5-CF₃ | H | 3-Cl | —NH— | 3-(trichloromethyl)phenyl |
| I.A1a.2337 | 5-CF₃ | H | 3-Cl | —NH— | 3-ethylphenyl |
| I.A1a.2338 | 5-CF₃ | H | 3-Cl | —NH— | 3-(trichloromethoxy)phenyl |
| I.A1a.2339 | 5-CF₃ | H | 3-Cl | —NH— | 3-(chlorodifluoromethyl)phenyl |
| I.A1a.2340 | 5-CF₃ | H | 3-Cl | —NH— | 3-(methylcarbonyl)phenyl |
| I.A1a.2341 | 5-CF₃ | H | 3-Cl | —NH— | 3-(methylsulfonyl)phenyl |
| I.A1a.2342 | 5-CF₃ | H | 3-Cl | —NH— | 3-(chloromethyl)phenyl |
| I.A1a.2343 | 5-CF₃ | H | 3-Cl | —NH— | 5-chloro-2-methoxyphenyl |
| I.A1a.2344 | 5-CF₃ | H | 3-Cl | —NH— | 3-(benzyloxy)phenyl |
| I.A1a.2345 | 5-Cl | H | 3-CF₃ | —NH— | phenyl |
| I.A1a.2346 | 5-Cl | H | 3-CF₃ | —NH— | 2-chlorophenyl |
| I.A1a.2347 | 5-Cl | H | 3-CF₃ | —NH— | 3-chlorophenyl |
| I.A1a.2348 | 5-Cl | H | 3-CF₃ | —NH— | 4-chlorophenyl |
| I.A1a.2349 | 5-Cl | H | 3-CF₃ | —NH— | 2,3-dichlorophenyl |
| I.A1a.2350 | 5-Cl | H | 3-CF₃ | —NH— | 2,5-dichlorophenyl |
| I.A1a.2351 | 5-Cl | H | 3-CF₃ | —NH— | 3,5-dichlorophenyl |
| I.A1a.2352 | 5-Cl | H | 3-CF₃ | —NH— | 2,4-dichlorophenyl |
| I.A1a.2353 | 5-Cl | H | 3-CF₃ | —NH— | 2,6-dichlorophenyl |
| I.A1a.2354 | 5-Cl | H | 3-CF₃ | —NH— | 2-fluorophenyl |
| I.A1a.2355 | 5-Cl | H | 3-CF₃ | —NH— | 3-fluorophenyl |
| I.A1a.2356 | 5-Cl | H | 3-CF₃ | —NH— | 4-fluorophenyl |
| I.A1a.2357 | 5-Cl | H | 3-CF₃ | —NH— | 2,3-difluorophenyl |
| I.A1a.2358 | 5-Cl | H | 3-CF₃ | —NH— | 3,5-difluorophenyl |
| I.A1a.2359 | 5-Cl | H | 3-CF₃ | —NH— | 2-methylphenyl |
| I.A1a.2360 | 5-Cl | H | 3-CF₃ | —NH— | 3-methylphenyl |
| I.A1a.2361 | 5-Cl | H | 3-CF₃ | —NH— | 4-methylphenyl |
| I.A1a.2362 | 5-Cl | H | 3-CF₃ | —NH— | 2,3-dimethylphenyl |
| I.A1a.2363 | 5-Cl | H | 3-CF₃ | —NH— | 3,5-dimethylphenyl |
| I.A1a.2364 | 5-Cl | H | 3-CF₃ | —NH— | 2-methoxyphenyl |
| I.A1a.2365 | 5-Cl | H | 3-CF₃ | —NH— | 3-methoxyphenyl |
| I.A1a.2366 | 5-Cl | H | 3-CF₃ | —NH— | 4-methoxyphenyl |
| I.A1a.2367 | 5-Cl | H | 3-CF₃ | —NH— | 2,3-dimethoxyphenyl |
| I.A1a.2368 | 5-Cl | H | 3-CF₃ | —NH— | 3,5-dimethoxyphenyl |
| I.A1a.2369 | 5-Cl | H | 3-CF₃ | —NH— | 2,5-dimethoxyphenyl |
| I.A1a.2370 | 5-Cl | H | 3-CF₃ | —NH— | 3-isopropylphenyl |
| I.A1a.2371 | 5-Cl | H | 3-CF₃ | —NH— | 3-(n-butyl)phenyl |
| I.A1a.2372 | 5-Cl | H | 3-CF₃ | —NH— | 3-phenylphenyl |
| I.A1a.2373 | 5-Cl | H | 3-CF₃ | —NH— | 3-(trifluoromethyl)phenyl |
| I.A1a.2374 | 5-Cl | H | 3-CF₃ | —NH— | 3-nitrophenyl |
| I.A1a.2375 | 5-Cl | H | 3-CF₃ | —NH— | 3-bromophenyl |
| I.A1a.2376 | 5-Cl | H | 3-CF₃ | —NH— | 2,3-dichlorophenyl |
| I.A1a.2377 | 5-Cl | H | 3-CF₃ | —NH— | 3-cyanophenyl |
| I.A1a.2378 | 5-Cl | H | 3-CF₃ | —NH— | 3-(phenoxy)phenyl |
| I.A1a.2379 | 5-Cl | H | 3-CF₃ | —NH— | 3-(trichloromethyl)phenyl |
| I.A1a.2380 | 5-Cl | H | 3-CF₃ | —NH— | 3-ethylphenyl |
| I.A1a.2381 | 5-Cl | H | 3-CF₃ | —NH— | 3-(trichloromethoxy)phenyl |
| I.A1a.2382 | 5-Cl | H | 3-CF₃ | —NH— | 3-(chlorodifluoromethyl)phenyl |
| I.A1a.2383 | 5-Cl | H | 3-CF₃ | —NH— | 3-(methylcarbonyl)phenyl |
| I.A1a.2384 | 5-Cl | H | 3-CF₃ | —NH— | 3-(methylsulfonyl)phenyl |
| I.A1a.2385 | 5-Cl | H | 3-CF₃ | —NH— | 3-(chloromethyl)phenyl |
| I.A1a.2386 | 5-Cl | H | 3-CF₃ | —NH— | 5-chloro-2-methylphenyl |
| I.A1a.2387 | 5-Cl | H | 3-CF₃ | —NH— | 3-(benzyloxy)phenyl |
| I.A1a.2388 | 6-Cl | H | H | —NH— | phenyl |
| I.A1a.2389 | 6-Cl | H | H | —NH— | 3-chlorophenyl |
| I.A1a.2390 | 6-Cl | H | H | —NH— | 2,3-dichlorophenyl |
| I.A1a.2391 | 6-Cl | H | H | —NH— | 2,5-dichlorophenyl |
| I.A1a.2392 | 6-Cl | H | H | —NH— | 3,5-dichlorophenyl |
| I.A1a.2393 | 6-Cl | H | H | —NH— | 3-fluorophenyl |
| I.A1a.2394 | 6-Cl | H | H | —NH— | 2,3-difluorophenyl |
| I.A1a.2395 | 6-Cl | H | H | —NH— | 3,5-difluorophenyl |
| I.A1a.2396 | 6-Cl | H | H | —NH— | 3-methylphenyl |
| I.A1a.2397 | 6-Cl | H | H | —NH— | 2,3-dimethylphenyl |
| I.A1a.2398 | 6-Cl | H | H | —NH— | 3,5-dimethylphenyl |
| I.A1a.2399 | 6-Cl | H | H | —NH— | 3-methoxyphenyl |
| I.A1a.2400 | 6-Cl | H | H | —NH— | 2,3-dimethoxyphenyl |
| I.A1a.2401 | 6-Cl | H | H | —NH— | 3,5-dimethoxyphenyl |
| I.A1a.2402 | 6-Cl | H | H | —NH— | 2,5-dimethoxyphenyl |
| I.A1a.2403 | 6-Cl | H | H | —NH— | 3-isopropylphenyl |
| I.A1a.2404 | 6-Cl | H | H | —NH— | 3-(n-butyl)phenyl |
| I.A1a.2405 | 6-Cl | H | H | —NH— | 3-phenylphenyl |
| I.A1a.2406 | 6-Cl | H | H | —NH— | 3-(trifluoromethyl)phenyl |
| I.A1a.2407 | 6-Cl | H | H | —NH— | 3-nitrophenyl |
| I.A1a.2408 | 6-Cl | H | H | —NH— | 3-bromophenyl |
| I.A1a.2409 | 6-Cl | H | H | —NH— | 2,3-dichlorophenyl |
| I.A1a.2410 | 6-Cl | H | H | —NH— | 3-cyanophenyl |
| I.A1a.2411 | 6-Cl | H | H | —NH— | 3-(phenoxy)phenyl |
| I.A1a.2412 | 6-Cl | H | H | —NH— | 3-(trichloromethyl)phenyl |
| I.A1a.2413 | 6-Cl | H | H | —NH— | 3-ethylphenyl |
| I.A1a.2414 | 6-Cl | H | H | —NH— | 3-(trichloromethoxy)phenyl |
| I.A1a.2415 | 6-Cl | H | H | —NH— | 3-(chlorodifluoromethyl)phenyl |
| I.A1a.2416 | 6-Cl | H | H | —NH— | 3-(methylcarbonyl)phenyl |
| I.A1a.2417 | 6-CF₃ | H | H | —NH— | phenyl |
| I.A1a.2418 | 6-CF₃ | H | H | —NH— | 3-chlorophenyl |
| I.A1a.2419 | 6-CF₃ | H | H | —NH— | 3,5-dichloro- |

TABLE C-continued

| No. | R¹ | R² | R³ | X | Q |
|---|---|---|---|---|---|
| I.A1a.2420 | 6-CF₃ | H | H | —NH— | phenyl |
| | | | | | 3-fluorophenyl |
| I.A1a.2421 | 6-CF₃ | H | H | —NH— | 3-methylphenyl |
| I.A1a.2422 | 6-CF₃ | H | H | —NH— | 2,3-dimethylphenyl |
| I.A1a.2423 | 6-CF₃ | H | H | —NH— | 3,5-dimethylphenyl |
| I.A1a.2424 | 6-CF₃ | H | H | —NH— | 3-methoxyphenyl |
| I.A1a.2425 | 6-CF₃ | H | H | —NH— | 2,3-dimethoxyphenyl |
| I.A1a.2426 | 6-CF₃ | H | H | —NH— | 3-isopropylphenyl |
| I.A1a.2427 | 6-CF₃ | H | H | —NH— | 3-phenylphenyl |
| I.A1a.2428 | 6-CF₃ | H | H | —NH— | 3-(trifluoromethyl)phenyl |
| I.A1a.2429 | 6-CF₃ | H | H | —NH— | 3-nitrophenyl |
| I.A1a.2430 | 6-CF₃ | H | H | —NH— | 3-bromophenyl |
| I.A1a.2431 | 6-CF₃ | H | H | —NH— | 3-cyanophenyl |
| I.A1a.2432 | 6-CF₃ | H | H | —NH— | 3-(phenoxy)phenyl |
| I.A1a.2433 | H | 4-CF₃ | H | —NH— | phenyl |
| I.A1a.2434 | H | 4-CF₃ | H | —NH— | 3-chlorophenyl |
| I.A1a.2435 | H | 4-CF₃ | H | —NH— | 3,5-dichlorophenyl |
| I.A1a.2436 | H | 4-CF₃ | H | —NH— | 3-fluorophenyl |
| I.A1a.2437 | H | 4-CF₃ | H | —NH— | 3-methylphenyl |
| I.A1a.2438 | H | 4-CF₃ | H | —NH— | 2,3-dimethylphenyl |
| I.A1a.2439 | H | 4-CF₃ | H | —NH— | 3,5-dimethylphenyl |
| I.A1a.2440 | H | 4-CF₃ | H | —NH— | 3-methoxyphenyl |
| I.A1a.2441 | H | 4-CF₃ | H | —NH— | 2,3-dimethoxyphenyl |
| I.A1a.2442 | H | 4-CF₃ | H | —NH— | 3-isopropylphenyl |
| I.A1a.2443 | H | 4-CF₃ | H | —NH— | 3-phenylphenyl |
| I.A1a.2444 | H | 4-CF₃ | H | —NH— | 3-(trifluoromethyl)phenyl |
| I.A1a.2445 | H | 4-CF₃ | H | —NH— | 3-nitrophenyl |
| I.A1a.2446 | H | 4-CF₃ | H | —NH— | 3-bromophenyl |
| I.A1a.2447 | H | 4-CF₃ | H | —NH— | 3-cyanophenyl |
| I.A1a.2448 | H | 4-CF₃ | H | —NH— | 3-(phenoxy)phenyl |
| I.A1a.2449 | H | H | 3-NO₂ | —NH— | phenyl |
| I.A1a.2450 | H | H | 3-NO₂ | —NH— | 3-chlorophenyl |
| I.A1a.2451 | H | H | 3-NO₂ | —NH— | 3,5-dichlorophenyl |
| I.A1a.2452 | H | H | 3-NO₂ | —NH— | 3-fluorophenyl |
| I.A1a.2453 | H | H | 3-NO₂ | —NH— | 3-methylphenyl |
| I.A1a.2454 | H | H | 3-NO₂ | —NH— | 2,3-dimethylphenyl |
| I.A1a.2455 | H | H | 3-NO₂ | —NH— | 3,5-dimethylphenyl |
| I.A1a.2456 | H | H | 3-NO₂ | —NH— | 3-methoxyphenyl |
| I.A1a.2457 | H | H | 3-NO₂ | —NH— | 2,3-dimethoxyphenyl |
| I.A1a.2458 | H | H | 3-NO₂ | —NH— | 3-isopropylphenyl |
| I.A1a.2459 | H | H | 3-NO₂ | —NH— | 3-phenylphenyl |
| I.A1a.2460 | H | H | 3-NO₂ | —NH— | 3-(trifluoromethyl)phenyl |
| I.A1a.2461 | H | H | 3-NO₂ | —NH— | 3-nitrophenyl |
| I.A1a.2462 | H | H | 3-NO₂ | —NH— | 3-bromophenyl |
| I.A1a.2463 | H | H | 3-NO₂ | —NH— | 3-cyanophenyl |
| I.A1a.2464 | H | H | 3-NO₂ | —NH— | 3-(phenoxy)phenyl |
| I.A1a.2465 | 6-Cl | 5-CF₃ | H | —NH— | phenyl |
| I.A1a.2466 | 6-Cl | 5-CF₃ | H | —NH— | 3-chlorophenyl |
| I.A1a.2467 | 6-Cl | 5-CF₃ | H | —NH— | 3-fluorophenyl |
| I.A1a.2468 | 6-Cl | 5-CF₃ | H | —NH— | 3-methylphenyl |
| I.A1a.2469 | 6-Cl | 5-CF₃ | H | —NH— | 3-methoxyphenyl |
| I.A1a.2470 | 6-Cl | 5-CF₃ | H | —NH— | 3-phenylphenyl |
| I.A1a.2471 | 6-Cl | 5-CF₃ | H | —NH— | 3-(trifluoromethyl)phenyl |
| I.A1a.2472 | 6-Cl | 5-CF₃ | H | —NH— | 3-nitrophenyl |
| I.A1a.2473 | 6-Cl | 5-CF₃ | H | —NH— | 3-cyanophenyl |
| I.A1a.2474 | H | 5-CF₃ | 3-CN | —NH— | phenyl |
| I.A1a.2475 | H | 5-CF₃ | 3-CN | —NH— | 3-chlorophenyl |
| I.A1a.2476 | H | 5-CF₃ | 3-CN | —NH— | 3-fluorophenyl |
| I.A1a.2477 | H | 5-CF₃ | 3-CN | —NH— | 3-methylphenyl |
| I.A1a.2478 | H | 5-CF₃ | 3-CN | —NH— | 3-methoxyphenyl |
| I.A1a.2479 | H | 5-CF₃ | 3-CN | —NH— | 3-phenylphenyl |
| I.A1a.2480 | H | 5-CF₃ | 3-CN | —NH— | 3-(trifluoromethyl)phenyl |
| I.A1a.2481 | H | 5-CF₃ | 3-CN | —NH— | 3-nitrophenyl |
| I.A1a.2482 | H | 5-CF₃ | 3-CN | —NH— | 3-cyanophenyl |
| I.A1a.2483 | 6-Cl | 4-CF₃ | H | —NH— | phenyl |
| I.A1a.2484 | 6-Cl | 4-CF₃ | H | —NH— | 3-chlorophenyl |
| I.A1a.2485 | 6-Cl | 4-CF₃ | H | —NH— | 3-fluorophenyl |
| I.A1a.2486 | 6-Cl | 4-CF₃ | H | —NH— | 3-methylphenyl |
| I.A1a.2487 | 6-Cl | 4-CF₃ | H | —NH— | 3-methoxyphenyl |
| I.A1a.2488 | 6-Cl | 4-CF₃ | H | —NH— | 3-phenylphenyl |
| I.A1a.2489 | 6-Cl | 4-CF₃ | H | —NH— | 3-(trifluoromethyl)phenyl |
| I.A1a.2490 | 6-Cl | 4-CF₃ | H | —NH— | 3-nitrophenyl |
| I.A1a.2491 | 6-Cl | 4-CF₃ | H | —NH— | 3-cyanophenyl |
| I.A1a.2492 | 6-Cl | H | 3-CN | —NH— | phenyl |
| I.A1a.2493 | 6-Cl | H | 3-CN | —NH— | 3-chlorophenyl |
| I.A1a.2494 | 6-Cl | H | 3-CN | —NH— | 3-fluorophenyl |
| I.A1a.2495 | 6-Cl | H | 3-CN | —NH— | 3-methylphenyl |
| I.A1a.2496 | 6-Cl | H | 3-CN | —NH— | 3-methoxyphenyl |
| I.A1a.2497 | 6-Cl | H | 3-CN | —NH— | 3-phenylphenyl |
| I.A1a.2498 | 6-Cl | H | 3-CN | —NH— | 3-(trifluoromethyl)phenyl |
| I.A1a.2499 | 6-Cl | H | 3-CN | —NH— | 3-nitrophenyl |
| I.A1a.2500 | 6-Cl | H | 3-CN | —NH— | 3-cyanophenyl |
| I.A1a.2501 | 6-CH₃ | 4-CH₃ | 3-CN | —NH— | phenyl |
| I.A1a.2502 | 6-CH₃ | 4-CH₃ | 3-CN | —NH— | 3-chlorophenyl |
| I.A1a.2503 | 6-CH₃ | 4-CH₃ | 3-CN | —NH— | 3-fluorophenyl |
| I.A1a.2504 | 6-CH₃ | 4-CH₃ | 3-CN | —NH— | 3-methylphenyl |
| I.A1a.2505 | 6-CH₃ | 4-CH₃ | 3-CN | —NH— | 3-methoxyphenyl |
| I.A1a.2506 | 6-CH₃ | 4-CH₃ | 3-CN | —NH— | 3-phenylphenyl |
| I.A1a.2507 | 6-CH₃ | 4-CH₃ | 3-CN | —NH— | 3-(trifluoromethyl)phenyl |
| I.A1a.2508 | 6-CH₃ | 4-CH₃ | 3-CN | —NH— | 3-nitrophenyl |
| I.A1a.2509 | 6-CH₃ | 4-CH₃ | 3-CN | —NH— | 3-cyanophenyl |
| I.A1a.2510 | 5-CF₃ | H | 3-Cl | —NH— | 3,4-dichlorophenyl |
| I.A1a.2511 | 6-Cl | H | 3-NO₂ | —NH— | 3-chlorophenyl |
| I.A1a.2512 | 6-Cl | 5-NO₂ | H | —NH— | 3-chlorophenyl |
| I.A1a.2513 | 6-Cl | 5-CN | H | —NH— | 3-chlorophenyl |

Other particularly preferred compounds of the formula I in which A=A1 are those which follows:

TABLE ABC-1

The compounds I.A1b.001–I.A1b.515, I.A1b.1001 to I.A1b.1515 and I.A1b.2001 to I.A1b.2515, which differ from the corresponding compounds I.A1a.001–I.A1a.515, I.A1a.1001 to I.A1a.1515 and I.A1a.2001 to I.A1a.2515 only by the fact that Alk is 1,2-propylidene:

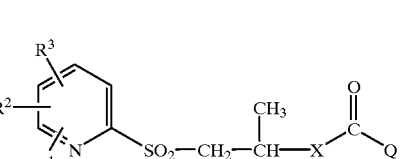

I.A1b

TABLE ABC-2

The compounds I.A1c.001–I.A1c.515, I.A1c.1001 to I.A1c.1515 and I.A1c.2001 to I.A1c.2515, which differ from the corresponding compounds I.A1a.001–I.A1a.515, I.A1a.1001 to I.A1a.1515 and I.A1a.2001 to I.A1a.2515 only by the fact that Alk is 2,3-propylidene:

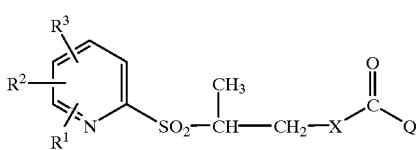

I.A1c

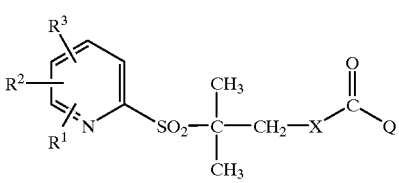

I.A1g

TABLE ABC-3

The compounds I.A1d.001–I.A1d.515, I.A1d.1001 to I.A1d.1515 and I.A1d.2001 to I.A1d.2515, which differ from the corresponding compounds I.A1a.001–I.A1a.515, I.A1a.1001 to I.A1a.1515 and I.A1a.2001 to I.A1a.2515 only by the fact that Alk is 1,2-butylidene:

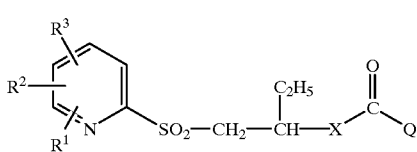

I.A1d

TABLE ABC-7

The compounds I.A1h.001–I.A1h.515, I.A1h.1001 to I.A1h.1515 and I.A1h.2001 to I.A1h.2515, which differ from the corresponding compounds I.A1a.001–I.A1a.515, I.A1a.1001 to I.A1a.1515 and I.A1a.2001 to I.A1a.2515 only by the fact that Alk is 2,3-pentylidene:

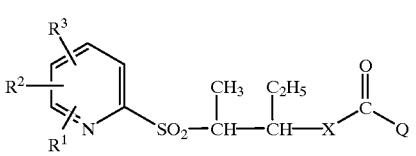

I.A1h

TABLE ABC-4

The compounds I.A1e.001–I.A1e.515, I.A1e.1001 to I.A1e.1515 and I.A1e.2001 to I.A1e.2515, which differ from the corresponding compounds I.A1a.001–I.A1a.515, I.A1a.1001 to I.A1a.1515 and I.A1a.2001 to I.A1a.2515 only by the fact that Alk is 3,4-butylidene:

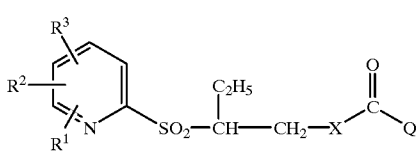

I.A1e

TABLE ABC-8

The compounds I.A1i.001–I.A1i.515, I.A1i.1001 to I.A1i.1515 and I.A1i.2001 to I.A1i.2515, which differ from the corresponding compounds I.A1a.001–I.A1a.515, I.A1a.1001 to I.A1a.1515 and I.A1a.2001 to I.A1a.2515 only by the fact that Alk is 3,4-pentylidene:

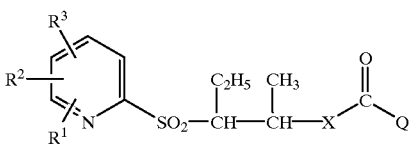

I.A1i

TABLE ABC-5

The compounds I.A1f.001–I.A1f.515, I.A1f.1001 to I.A1f.1515 and I.A1f.2001 to I.A1f.2515, which differ from the corresponding compounds I.A1a.001–I.A1a.515, I.A1a.1001 to I.A1a.1515 and I.A1a.2001 to I.A1a.2515 only by the fact that Alk is 2,3-butylidene:

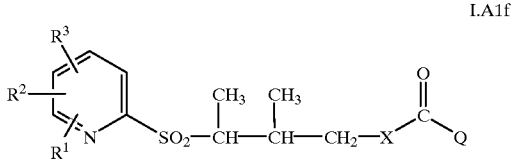

I.A1f

TABLE ABC-9

The compounds I.A1k.001–I.A1k.515, I.A1k.1001 to I.A1k.1515 and I.A1k.2001 to I.A1k.2515, which differ from the corresponding compounds I.A1a.001–I.A1a.515, I.A1a.1001 to I.A1a.1515 and I.A1a.2001 to I.A1a.2515 only by the fact that Alk is 3,4-hexylidene:

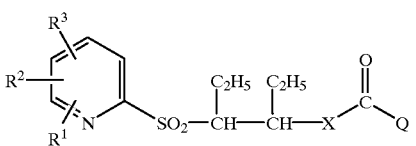

I.A1k

TABLE ABC-6

The compounds I.A1g.001–I.A1g.515, I.A1g.1001 to I.A1g.1515 and I.A1g.2001 to I.A1g.2515, which differ from the corresponding compounds I.A1a.001–I.A1a.515, I.A1a.1001 to I.A1a.1515 and I.A1a.2001 to I.A1a.2515 only by the fact that Alk is 2-methyl-2,3-propylidene:

TABLE ABC-10

The compounds I.A1m.001–I.A1m.515, I.A1m.1001 to I.A1m.1515 and I.A1m.2001 to I.A1m.2515, which differ from the corresponding compounds I.A1a.001–I.A1a.515, I.A1a.1001 to I.A1a.1515 and I.A1a.2001 to I.A1a.2515 only by the fact that m is zero:

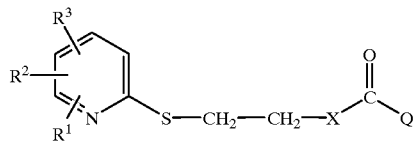

I.A1m

TABLE ABC-11

The compounds I.A1n.001–I.A1n.515, I.A1n.1001 to I.A1n.1515 and I.A1n.2001 to I.A1n.2515, which differ from the corresponding compounds I.A1a.001–I.A1a.515, I.A1a.1001 to I.A1a.1515 and I.A1a.2001 to I.A1a.2515 only by the fact that m is 1:

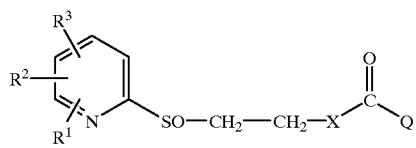

I.A1n

TABLE ABC-12

The compounds I.A1o.001–I.A1o.515, I.A1o.1001 to I.A1o.1515 and I.A1o.2001 to I.A1o.2515, which differ from the corresponding compounds I.A1a.001–I.A1a.515, I.A1a.1001 to I.A1a.1515 and I.A1a.2001 to I.A1a.2515 only by the fact that Alk is 1-methyl-2,3-propylidene and m is zero:

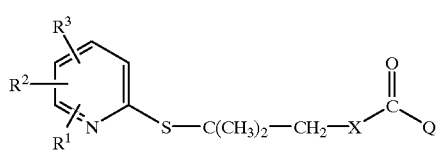

I.A1o

Other compounds I which are preferred with a view to their activity against harmful fungi are those which follow:

TABLE DEF-1

Compounds of the Formula I.A7-1

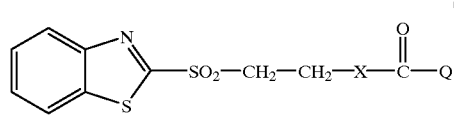

(I.A7-1)

where X and Q together correspond in each case to one line of Tables D, E and F.

TABLE DEF-2

Compounds of the Formula I.A7-2

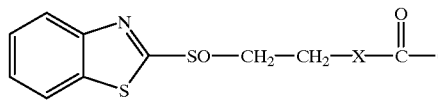

(I.A7-2)

where X and Q together correspond in each case to one line of Tables D, E and F.

TABLE DEF-3

Compounds of the Formula I.A7-3

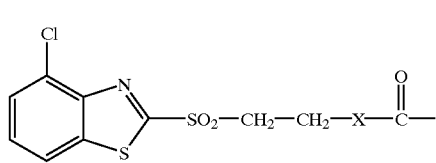

(I.A7-3)

where X and Q together correspond in each case to one line of Tables D, E and F.

TABLE DEF-4

Compounds of the formula I.A7-4

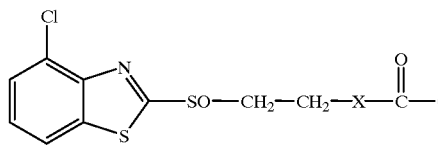

(I.A7-4)

where X and Q together correspond in each case to one line of Tables D, E and F.

TABLE DEF-5

Compounds of the formula I.A7-5

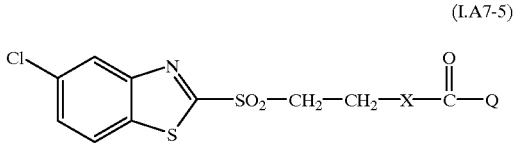

(I.A7-5)

where X and Q together correspond in each case to one line of Tables D, E and F.

TABLE DEF-6

Compounds of the formula I.A7-6

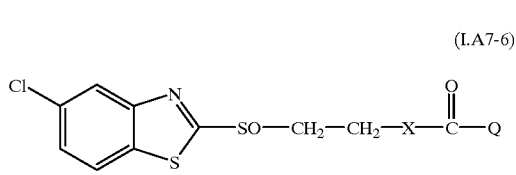
(I.A7-6)

where X and Q together correspond in each case to one line of Tables D, E and F.

TABLE DEF-7

Compounds of the formula I.A7-7

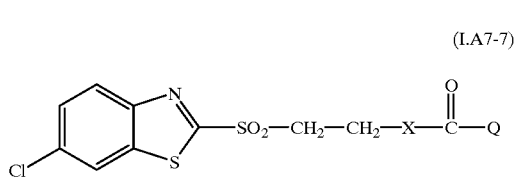
(I.A7-7)

where X and Q together correspond in each case to one line of Tables D, E and F.

TABLE DEF-8

Compounds of the formula I.A7-8

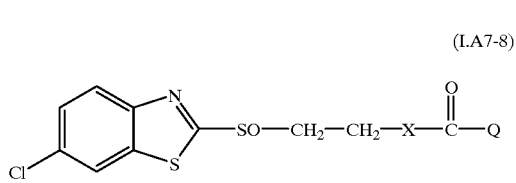
(I.A7-8)

where X and Q together correspond in each case to one line of Tables D, E and F.

TABLE DEF-9

Compounds of the formula I.A7-9

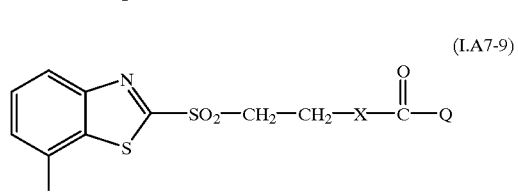
(I.A7-9)

where X and Q together correspond in each case to one line of Tables D, E and F.

TABLE DEF-10

Compounds of the formula I.A7-10

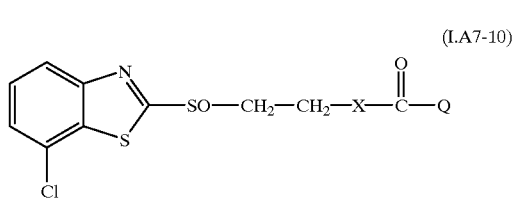
(I.A7-10)

where X and Q together correspond in each case to one line of Tables D, E and F.

TABLE DEF-11

Compounds of the formula I.A7-11

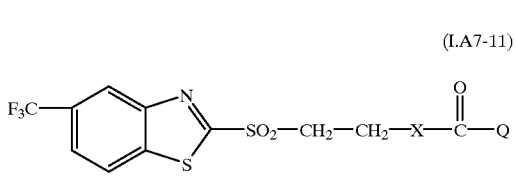
(I.A7-11)

where X and Q together correspond in each case to one line of Tables D, E and F.

TABLE DEF-12

Compounds of the formula I.A7-12

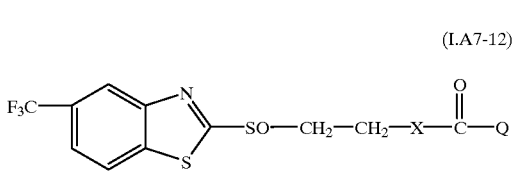
(I.A7-12)

where X and Q together correspond in each case to one line of Tables D, E and F.

TABLE DEF-13

Compounds of the formula I.A7-13

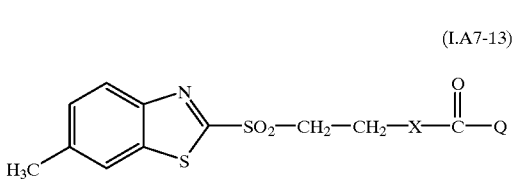
(I.A7-13)

where X and Q together correspond in each case to one line of Tables D, E and F.

TABLE DEF-14

Compounds of the formula I.A7-14

(I.A7-14)

where X and Q together correspond in each case to one line of Tables D, E and F.

TABLE DEF-15

Compounds of the formula I.A7-15

(I.A7-15)

where X and Q together correspond in each case to one line of Tables D, E and F.

TABLE DEF-16

Compounds of the formula I.A7-16

(I.A7-16)

where X and Q together correspond in each case to one line of Tables D, E and F.

TABLE DEF-17

Compounds of the formula I.A7-17

(I.A7-17)

where X and Q together correspond in each case to one line of Tables D, E and F.

TABLE DEF-18

Compounds of the formula I.A7-18

(I.A7-18)

where X and Q together correspond in each case to one line of Tables D, E and F.

TABLE DEF-19

Compounds of the formula I.A8-1

(I.A8-1)

where X and Q together correspond in each case to one line of Tables D, E and F.

TABLE DEF-20

Compounds of the formula I.A8-2

(I.A8-2)

where X and Q together correspond in each case to one line of Tables D, E and F.

TABLE DEF-21

Compounds of the formula I.A6-1

(I.A6-1)

where X and Q together correspond in each case to one line of Tables D, E and F.

TABLE DEF-22

Compounds of the formula I.A6-2

(I.A6-2)

where X and Q together correspond in each case to one line of Tables D, E and F.

TABLE DEF-23

Compounds of the formula I.A4-1

(I.A4-1)

[Structure: pyrimidine-SO$_2$-CH$_2$-CH$_2$-X-C(=O)-Q]

where X and Q together correspond in each case to one line of Tables D, E and F.

TABLE DEF-24

Compounds of the formula I.A4-2

(I.A4-2)

[Structure: pyrazine-SO-CH$_2$-CH$_2$-X-C(=O)-Q]

where X and Q together correspond in each case to one line of Tables D, E and F.

TABLE DEF-25

Compounds of the formula I.A2-1

(I.A2-1)

[Structure: pyrimidine-SO$_2$-CH$_2$-CH$_2$-X-C(=O)-Q]

where X and Q together correspond in each case to one line of Tables D, E and F.

TABLE DEF-26

Compounds of the formula I.A2-2

(I.A2-2)

[Structure: pyrimidine-SO-CH$_2$-CH$_2$-X-C(=O)-Q]

where X and Q together correspond in each case to one line of Tables D, E and F.

TABLE DEF-27

Compounds of the formula I.A2-3

(I.A2-3)

[Structure: 4-methylpyrimidine-SO$_2$-CH$_2$-CH$_2$-X-C(=O)-Q]

where X and Q together correspond in each case to one line of Tables D, E and F.

TABLE DEF-28

Compounds of the formula I.A2-4

(I.A2-4)

[Structure: 4-methylpyrimidine-SO-CH$_2$-CH$_2$-X-C(=O)-Q]

where X and Q together correspond in each case to one line of Tables D, E and F.

TABLE DEF-29

Compounds of the formula I.A2-5

(I.A2-5)

[Structure: 5-methylpyrimidine-SO$_2$-CH$_2$-CH$_2$-X-C(=O)-Q]

where X and Q together correspond in each case to one line of Tables D, E and F.

TABLE DEF-30

Compounds of the formula I.A2-6

(I.A2-6)

[Structure: 5-methylpyrimidine-SO-CH$_2$-CH$_2$-X-C(=O)-Q]

where X and Q together correspond in each case to one line of Tables D, E and F.

TABLE DEF-31

Compounds of the formula I.A2-7

(I.A2-7)

[Structure: 5-trifluoromethylpyrimidine-SO$_2$-CH$_2$-CH$_2$-X-C(=O)-Q]

where X and Q together correspond in each case to one line of Tables D, E and F.

TABLE DEF-32

Compounds of the formula I.A2-8

(I.A2-8)

[Structure: 5-trifluoromethylpyrimidine-SO-CH$_2$-CH$_2$-X-C(=O)-Q]

where X and Q together correspond in each case to one line of Tables D, E and F.

TABLE DEF-33

Compounds of the formula I.A3-1

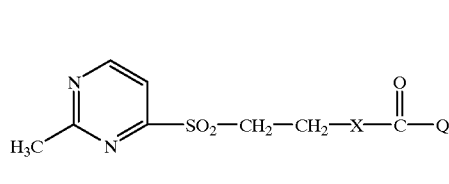
(I.A3-1)

where X and Q together correspond in each case to one line of Tables D, E and F.

TABLE DEF-34

Compounds of the formula I.A3-2

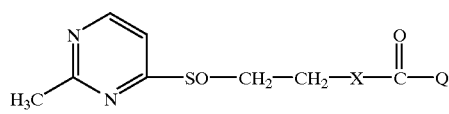
(I.A3-2)

where X and Q together correspond in each case to one line of Tables D, E and F.

TABLE DEF-35

Compounds of the formula I.A3-3

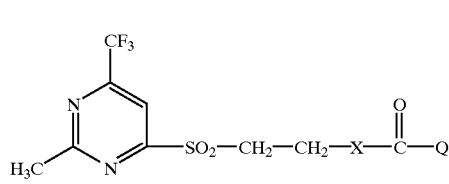
(I.A3-3)

where X and Q together correspond in each case to one line of Tables D, E and F.

TABLE DEF-36

Compounds of the formula I.A3-4

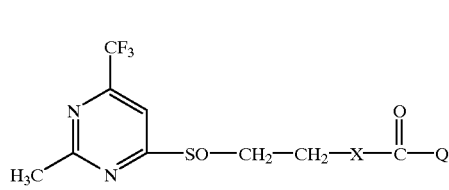
(I.A3-4)

where X and Q together correspond in each case to one line of Tables D, E and F.

TABLE DEF-37

Compounds of the formula I.A3-5

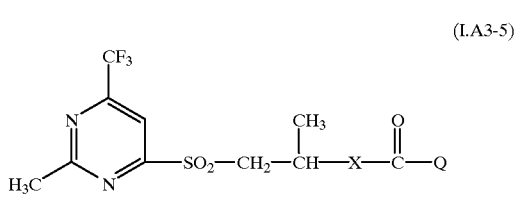
(I.A3-5)

where X and Q together correspond in each case to one line of Tables D, E and F.

TABLE DEF-38

Compounds of the formula I.A3-6

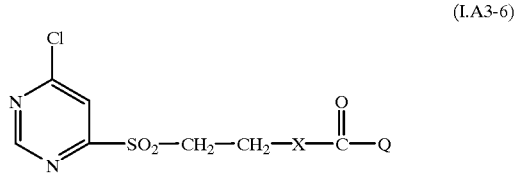
(I.A3-6)

where X and Q together correspond in each case to one line of Tables D, E and F.

TABLE DEF-39

Compounds of the formula I.A3-7

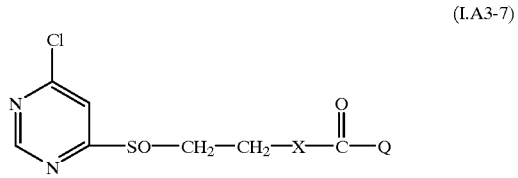
(I.A3-7)

where X and Q together correspond in each case to one line of Tables D, E and F.

TABLE DEF-40

Compounds of the formula I.A8-3

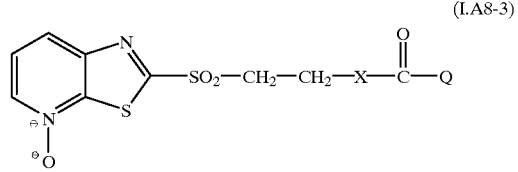
(I.A8-3)

where X and Q together correspond in each case to one line of Tables D, E and F.

TABLE DEF-41

Compounds of the formula I.A8-4

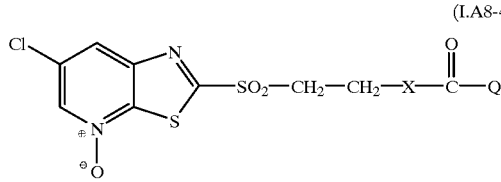

(I.A8-4)

where X and Q together correspond in each case to one line of Tables D, E and F.

TABLE D

| No. | X | R⁴ |
|---|---|---|
| D.1 | —O— | phenyl |
| D.2 | —O— | 2-chlorophenyl |
| D.3 | —O— | 3-chlorophenyl |
| D.4 | —O— | 4-chlorophenyl |
| D.5 | —O— | 2,3-dichlorophenyl |
| D.6 | —O— | 2,5-dichlorophenyl |
| D.7 | —O— | 3,5-dichlorophenyl |
| D.8 | —O— | 2,4-dichlorophenyl |
| D.9 | —O— | 2,6-dichlorophenyl |
| D.10 | —O— | 2-fluorophenyl |
| D.11 | —O— | 3-fluorophenyl |
| D.12 | —O— | 4-fluorophenyl |
| D.13 | —O— | 2,3-difluorophenyl |
| D.14 | —O— | 3,5-difluorophenyl |
| D.15 | —O— | 2-methylphenyl |
| D.16 | —O— | 3-methylphenyl |
| D.17 | —O— | 4-methylphenyl |
| D.18 | —O— | 2,3-dimethylphenyl |
| D.19 | —O— | 3,5-dimethylphenyl |
| D.20 | —O— | 2-methoxyphenyl |
| D.21 | —O— | 3-methoxyphenyl |
| D.22 | —O— | 4-methoxyphenyl |
| D.23 | —O— | 2,3-dimethoxyphenyl |
| D.24 | —O— | 3,5-dimethoxyphenyl |
| D.25 | —O— | 2,5-dimethoxyphenyl |
| D.26 | —O— | 3-isopropylphenyl |
| D.27 | —O— | 3-(n-butyl)phenyl |
| D.28 | —O— | 3-phenylphenyl |
| D.29 | —O— | 3-trifluoromethylphenyl |
| D.30 | —O— | 3-nitrophenyl |
| D.31 | —O— | 3-bromophenyl |
| D.32 | —O— | 2,3-dichlorophenyl |
| D.33 | —O— | 3-cyanophenyl |
| D.34 | —O— | 3-phenoxyphenyl |
| D.35 | —O— | 3-(trichloromethyl)phenyl |
| D.36 | —O— | 3-ethylphenyl |
| D.37 | —O— | 3-(trichloromethoxy)phenyl |
| D.38 | —O— | 3-(chlorodifluoromethyl)phenyl |
| D.39 | —O— | 3-(methylcarbonyl)phenyl |
| D.40 | —O— | 3-(methylsulfonyl)phenyl |
| D.41 | —O— | 3-(chloromethyl)phenyl |
| D.42 | —O— | 5-chloro-2-methoxyphenyl |
| D.43 | —O— | 3-(benzyloxy)phenyl |

TABLE E

| No. | X | Q |
|---|---|---|
| E.1 | —S— | phenyl |
| E.2 | —S— | 2-chlorophenyl |
| E.3 | —S— | 3-chlorophenyl |
| E.4 | —S— | 4-chlorophenyl |
| E.5 | —S— | 2,3-dichlorophenyl |
| E.6 | —S— | 2,5-dichlorophenyl |
| E.7 | —S— | 3,5-dichlorophenyl |
| E.8 | —S— | 2,4-dichlorophenyl |
| E.9 | —S— | 2,6-dichlorophenyl |
| E.10 | —S— | 2-fluorophenyl |
| E.11 | —S— | 3-fluorophenyl |
| E.12 | —S— | 4-fluorophenyl |
| E.13 | —S— | 2,3-difluorophenyl |
| E.14 | —S— | 3,5-difluorophenyl |
| E.15 | —S— | 2-methylphenyl |
| E.16 | —S— | 3-methylphenyl |
| E.17 | —S— | 4-methylphenyl |
| E.18 | —S— | 2,3-dimethylphenyl |
| E.19 | —S— | 3,5-dimethylphenyl |
| E.20 | —S— | 2-methoxyphenyl |
| E.21 | —S— | 3-methoxyphenyl |
| E.22 | —S— | 4-methoxyphenyl |
| E.23 | —S— | 2,3-dimethoxyphenyl |
| E.24 | —S— | 3,5-dimethoxyphenyl |
| E.25 | —S— | 2,5-dimethoxyphenyl |
| E.26 | —S— | 3-isopropylphenyl |
| E.27 | —S— | 3-(n-butyl)phenyl |
| E.28 | —S— | 3-phenylphenyl |
| E.29 | —S— | 3-trifluoromethylphenyl |
| E.30 | —S— | 3-nitrophenyl |
| E.31 | —S— | 3-bromophenyl |
| E.32 | —S— | 2,3-dichlorophenyl |
| E.33 | —S— | 3-cyanophenyl |
| E.34 | —S— | 3-phenoxyphenyl |
| E.35 | —S— | 3-(trichloromethyl)phenyl |
| E.36 | —S— | 3-ethylphenyl |
| E.37 | —S— | 3-(trichloromethoxy)phenyl |
| E.38 | —S— | 3-(chlorodifluoromethyl)phenyl |
| E.39 | —S— | 3-(methylcarbonyl)phenyl |
| E.40 | —S— | 3-(methylsulfonyl)phenyl |
| E.41 | —S— | 3-(chloromethyl)phenyl |
| E.42 | —S— | 5-chloro-2-methoxyphenyl |
| E.43 | —S— | 3-(benzyloxy)phenyl |

TABLE F

| No. | X | Q |
|---|---|---|
| F.1 | —NH— | phenyl |
| F.2 | —NH— | 2-chlorophenyl |
| F.3 | —NH— | 3-chlorophenyl |
| F.4 | —NH— | 4-chlorophenyl |
| F.5 | —NH— | 2,3-dichlorophenyl |
| F.6 | —NH— | 2,5-dichlorophenyl |
| F.7 | —NH— | 3,5-dichlorophenyl |
| F.8 | —NH— | 2,4-dichlorophenyl |
| F.9 | —NH— | 2,6-dichlorophenyl |
| F.10 | —NH— | 2-fluorophenyl |
| F.11 | —NH— | 3-fluorophenyl |
| F.12 | —NH— | 4-fluorophenyl |
| F.13 | —NH— | 2,3-difluorophenyl |
| F.14 | —NH— | 3,5-difluorophenyl |
| F.15 | —NH— | 2-methylphenyl |
| F.16 | —NH— | 3-methylphenyl |
| F.17 | —NH— | 4-methylphenyl |
| F.18 | —NH— | 2,3-dimethylphenyl |
| F.19 | —NH— | 3,5-dimethylphenyl |
| F.20 | —NH— | 2-methoxyphenyl |
| F.21 | —NH— | 3-methoxyphenyl |
| F.22 | —NH— | 4-methoxyphenyl |
| F.23 | —NH— | 2,3-dimethoxyphenyl |
| F.24 | —NH— | 3,5-dimethoxyphenyl |
| F.25 | —NH— | 2,5-dimethoxyphenyl |
| F.26 | —NH— | 3-isopropylphenyl |
| F.27 | —NH— | 3-(n-butyl)phenyl |
| F.28 | —NH— | 3-phenylphenyl |
| F.29 | —NH— | 3-trifluoromethylphenyl |
| F.30 | —NH— | 3-nitrophenyl |
| F.31 | —NH— | 3-bromophenyl |
| F.32 | —NH— | 2,3-dichlorophenyl |
| F.33 | —NH— | 3-cyanophenyl |
| F.34 | —NH— | 3-phenoxyphenyl |

TABLE F-continued

| No. | X | Q |
|---|---|---|
| F.35 | —NH— | 3-(trichloromethyl)phenyl |
| F.36 | —NH— | 3-ethylphenyl |
| F.37 | —NH— | 3-(trichloromethoxy)phenyl |
| F.38 | —NH— | 3-(chlorodifluoromethyl)phenyl |
| F.39 | —NH— | 3-(methylcarbonyl)phenyl |
| F.40 | —NH— | 3-(methylsulfonyl)phenyl |
| F.41 | —NH— | 3-(chloromethyl)phenyl |
| F.42 | —NH— | 5-chloro-2-methoxyphenyl |
| F.43 | —NH— | 3-(benzyloxy)phenyl |

The compounds of the formula I may contain one or more chiral centers, in which case they are normally obtained in the form of enantiomer or diastereomer mixtures. If desired, the mixtures can be separated into the essentially pure isomers by means of the methods customary for this purpose, eg. by means of crystallization or chromatography on an optically active absorbate. Pure optically active isomers may also be prepared for example from suitable optically active starting materials.

The compounds I, their salts and N-oxides are suitable, both in the form of isomer mixtures and in the form of the pure isomers, for controlling harmful fungi and animal pests. They are distinguished by an outstanding activity against a broad spectrum of phytopathogenic fungi, in particular from the class of Phycomycetes. Some of them act systemically and can be employed as foliar- or soil-acting fungicides.

The novel compounds I are suitable for controlling harmful fungi.

Depending on their chemical and physical properties, the compounds I can be formulated with customary formulation auxiliaries, ie. those known to the expert. The products of this process are termed herein "compositions". Examples of suitable formulation auxiliaries are solid or liquid carriers, surfactants and tacifiers.

Liquid carriers are to be understood as meaning liquid solvents, such as wter and organic solvents, the latter acting as an auxiliary solvent, especially when water is used as the solvent. The following organic solvents can be used: aromatics such as xylene, toluene and alkylnapthalenes, chlorinated aromatics or chlorinated aliphatic hydrocarbons such as chlorobenzenes, chlorethylenes and methylene chloride, aliphatic hydrocarbons such as cyclohexane and paraffins, eg. mineral oil fractions, alcohols such as butanol, isobutanol, cyclohexanol and glycol and the relevant ethers and esters, ketones such as acetone, emthyl ethyl ketone, methyl isobutyl ketone and cyclohexanone, and aprotic dipolar solvents such as dimethylformamide, n-methyl-2-pyrrolidone and dimethyl sulfoxide.

Examples of solid carriers are: ground natural minerals and mineral earths such as silicas, silicates, kaolins, clays, bole, loess, talc, chalk, limestone, lime, dolomite, magnesium oxide, quarz, attapulgite, montmorillonite and diatomaceous earth; ground synthetic minerals such as highly-disperse silica, or mills of synthetic alumina and of synthetic silicates. Examples of solid carriers which are particularly suitable for granules are: crushed and fracitonated natural rocks such as calcite, marble, pumice, sepiolite; synthetic granules of inorganic and organic mills; granules of organic material such as sawdust, coconut shells, maize cobs or tobacco stalks.

Suitable surfactants and nonionic and anionic emulsifiers/foam formers and dispersants:

fatty acid polyoxyethylene esters such as lauryl alcohol polyoxyethylene ether acetate, alkyl polyoxyethylene ethers or alkyl polyoxypropylene ethers, such as of isotridecyl alcohol and fatty alcohol polyoxyethylene ether, alkylaryl alcohol polyoxyethylene ethers such as octylphenol polyoxyethylene ether, tributylphenol polyoxyethylene ether, ethoxylated iso-octylphenol, octylphenol or nonylphenol or castor oil, sorbitol esters, arylsulfonic acids, alkylsulfonic acids, alkylsulfuric acids, alkali metal, alkaline earth metal and ammonium salts of arylsulfonic acids, eg. ligno-, phenol-, naphthalene- and dibutylnaphthalenesulfonic acid, alkylsulfonic acids, alkylarylsulfonic acids, alkylsulfuric acids, lauryl ether sulfuric acids and fatty alcohol sulfuric acids, fatty acids, sulfated hexa-, hepta- and octadecanols and fatty alcohol glycol ethers, condensates of sulfonated naphthalene and its derivatives with formaldehyde, condensates of naphthalenesulfonic acids with phenol and formaldehyde, protein hydrolysates and in particular as dispersants: lignin-sulfite waste liquors and methylcellulose.

Examples of tackifiers are: carboxymethylcellulose; natural and synthetic polymers in the form of powders, granules or latices, such as gum arabic, polyvinyl alcohol, polyvinyl acetate, natural phospholipids such as cephalins and lecitins, and synthetic phospholipids.

The compositions may furthermore comprise one or more representatives of the following groups of substances; colorants, other known active ingredients, trace elements and other additives.

Examples of suitable colorants are inorganic pigments such as iron oxide, titanium oxide, Prussian Blue, and furthermore organic pigments such as alizarin, azo and metal phthalocyanine colorants. Other known active ingredients are to be noted as meaning, for example, other fungicides, and insecticides, acaricides, herbicides and growth regulators. Examples of trace elements are salts of iron, manganese, boron, copper, cobalt, molybdenum and zinc. Other suitable additives are, for example, mineral and vegetable oils.

Furthermore, the compositions may be mixed with other components of practical importance, such as fertilizers or other finished compositions which comprise active ingredient.

The compositions are prepared in a manner known per se, i.e. depending on the chemical and physical properties of the substances employed, for example by mixing, concomitant grinding, spraying on, extruding, granulating or dissolving in water, the latter—if desired—with the aide of an organic solvent. Powders, materials for spreading and dust may be obtained, for example, by mixing or concomitantly grinding the compounds I with a solid carrier.

Depending on the substances employed, examples of the compositions are solutions, emulsions, suspensions, powders, foams, pastes, granules, aerosols or microencapsulations in polymeric substances or in coating materials for seed.

If appropriate, the compositions, which are generally commercially available in the form of concentrates, are dissolved, diluted etc. in the customary manner, normally using water in the case of wettable powders, water-dispersible granules, emulsifiable concentrates, dispersions, and, in some cases, also in the case of microgranules. Preparations in the form of dust and granules, and sprayable solutions, are usually not diluted further with other inert substances prior to use.

The compositions are applied in a manner known per se, for example by spraying, atomizing, dusting, spreading or pouring. The plants are generally sprayed or dusted with the compositions. Alternatively or additionally, the seeds of the plants are treated in a manner known per se.

Examples of such preparations are:

I. a solution of 90 parts by weight of a compound I according to the invention and 10 parts by weight of N-methyl-2-pyrrolidone, which is suitable for use in the form of microdrops;

II. a mixture of 20 parts by weight of a compound I according to the invention, 80 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely distributing the solution in water;

III. an aqueous dispersion of 20 parts by weight of a compound I according to the invention, 40 parts by weight of cyclohexanone, 30 parts by weight of isobutanol, 20 parts by weight of the adduct of 40 mol of ethylene oxide to 1 mol of castor oil;

IV. an aqueous dispersion of 20 parts by weight of a compound I according to the invention, 25 parts by weight of cyclohexanol, 65 parts by weight of a mineral oil fraction of boiling point 210 to 280° C. and 10 parts by weight of the adduct of 40 mol of ethylene oxide to 1 mol of castor oil;

V. a mixture, ground in a hammer mill, of 80 parts by weight of a compound I according to the invention, 3 parts by weight of sodium diisobutylnaphthalene-1-sulfonate, 10 parts by weight of the sodium salt of a lignosulfonic acid from a sulfite waste liquor and 7 parts by weight of pulverulent silica gel; a spray mixture was obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 92 parts by weight of pulverulent silica gel and 8 parts by weight of paraffin oil which had been sprayed onto the surface of this silica gel; this preparation imparts good adherence properties to the active ingredient;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a paraffinic mineral oil.

If the compounds I are applied as such, the most important aspect is that they are finely distributed.

The compound I and the compositions according to the invention are distinguished by an outstanding activity against a broad spectrum of phyopathogenic fungi, in particular from the classes of the Ascomycetes,
Basidiomycetes,
Deuteromycetes and
Phycomycetes.

Some of them act systemically and can be employed as foliar- and soil-acting fungicides.

They are especially important for controlling a large number of fungi which infect a variety of crop plants such as wheat, rye, barley, oats, rice, maize, grass, cotton, soya, coffee, sugar cane, grapevines, fruit species, ornamentals, vegetable species such as cucumbers, beans and cucurbits, and the seeds of these plants.

The composition according to the invention and the compounds I, their salts and their N-oxides are applied by treating the harmful fungi, their environment, or the seeds, plants, areas, materials or spaces to be protected against fungal infection with a fungicidally active amount of these substances. Application can be effected before or after infection with the fungi.

Specifically, the compositions according to the invention and the compounds I are suitable for controlling the following plant diseases:

*Erysiphe graminins* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, grapevines, ornamentals and vegetables, *Cercospora arachidicola* in groundnuts, *Pseudocercosporella herpotrichoides* in wheat and barley, *Pyricularia oryzae* in rice, Phytophthora infestans in potatoes and tomatoes, Fusarium and Verticillium species in a variety of plants, *Plasmopara viticola* in grapevines, Pseudoperonospora species in hops and cucumbers, and Alternaria species in vegetables and fruit.

The control of botrytis using the compositions according to the invention or the compounds I is preferred.

The compositions according to the invention or the compounds I may also be employed in the protection of materials (protection of wood), e.g. against *Paecilomyces variotii*.

The compositions according to the invention generally comprise 0.1 to 95, preferably 0.5 to 90, % by weight of the compounds I.

Depending on the nature of the desired effect, the rates of application of the compounds I are from 0.01 to 2.0 kg per ha.

In the case of seed treatment, 0.001 to 50 g, preferably 0.01 to 10 g, of a compound I are generally required per kilogram of seed.

The compounds I may also exist in the compositions according to the invention together with other active ingredients conventionally used in crop protection, e.g. herbicides, insecticides, growth regulators, fungicides, or else fertilizers. A mixture with other fungicides frequently results in a widened fungicidal spectrum of action.

The following list of fungicidal active ingredients together with which the compounds I can be used is intended to illustrate the possible combinations, but not to impose any limitation:

Sulfur, dithiocarbamates and their derivatives, such as iron(III) dimethyldithiocarbamate, zinc dimethyldithiocarbamate, zinc ethylenebisdithiocarbamate, manganes ethylenebisdithiocarbamate, manganese zinc ethylenediamine-bis-dithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

Nitro derivatives such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitro-isophthalate;

Heterocyclic substances such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichlormethylthiotetrahydrophthalimide, N-trichloromethylthiophthalimide, N-Dichlorofluoromethylthio-N',N'-dimethyl-N-phenylsulfamide, 5-ethoxy-3-trichloromethyl-1,2,3-thiadiazole, 2-thiocyanomethylthiobenzothiazole, 1,4-dichloro-2,5-dimethoxybenzene, 4-(2-chlorophenylhydrazone)-3-methyl-5-isoxazolone, pyridine 2-thio-1-oxide, 8-hydroxyguinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-metyl-5,6-dihydro-4H-pyran-3-carboxanilide, 2,4,5-trimethylfuran-3-carboxanilide, N-cyclohexyl-2,5-dimethylfuran-3-carboxamide, N-cyclohexylmethoxy-2,5-dimethylfuran-3-carboxamide, 2-methylbenzanilide, 2-iodobenzanilide, N-formyl-N-morpholine-2,2,2-trichloroethyl acetal, piperazin-1,4-diylbis(2,2,2-trichloroethyl)formamide, 1-(3,4-dichloroanilino)-1-formylamino-2,2,2-trichloroethane, 2,6-dimethyl-N-tridecylmorpholine and its salts, 2,6-dimethyl-N-cyclodedecylmorpholine and its salts, N-[3-(p-tert-butylphenyl)-2-methylpropyl]-cis-2,6-dimethyl-morpholine, N-[3-(p-tert-butylphenyl)-2-methyl-propyl]-piperidine, 1-[2-(2,4-dichlorphenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycrabonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, 1-[3-(2-chlorophenyl)-1-(4-fluorophenyl)-oxiran-2-yl-methyl]-1H-1,2,4-triazole and a variety of fungicides such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, methyl N-(2,6-dimethylphenyl)-N-(2'-methoxyacetyl)-DL-alaninate, N-(2,6-dimethylphenyl)-N-chloroacetyl-D,L-2-aminobutyrolactone, methyl N-(2,6-dimethylphenyl)-N-(phenylacetyl)-DL-alaninate, 5-methyl-5-vinyl-3-(3,5-dichlorphenyl)-2,4-dioxo-1,3-oxazolidine, 3-(3,5-dichlorophenyl)-5-methyl-5-methoxymethyl-1,3-oxazolidine, 3-(3,5-dichlorophenyl)-5-methyl-5-methoxymethyl-1,3-oxazolidine-2,4-dione, 3-(3,5-dichlorphenyl)-1-isopropyl-carbamoylhydantoin, N-(3,5-dichlorphenyl)-1,2-dimethylcyclopropane-1,2-dicarboximide, 2-cyano-[N-(ethylaminocarbonyl)-2-methoximino]-acetamide, 1-[2-(2,4-dichlorophenyl)pentyl]-1H-1,2,4-triazole, 2,4-difluoro-α-(1H-1,2,4-triazolyl-1-methyl)-benzahydryl alcohol, N-(3-chloro-2,6-dinitro-4-trifluoromethyl-phenyl)-5-trifluoromethyl-3-chloro-2-aminopyridine, 1-(bis(4-fluorophenyl)methylsilyl)methyl)-1H-1,2,4-triazole.

Strobilurins such as methyl E-methoximino-[α-(o-tolyloxy)-o-tolyl]acetate, methyl E-2-{2-[6-(2-cyanophenoxy)pyrimidin-4-yl-oxy]-phenyl}-3-methoxyacrylate, methyl E-methoximino-[α-(2-phenoxyphenyl)acetamide, methyl E-methoximino-[α-(2,5-dimethylphenoxy)-o-tolyl]acetamide.

Anilinopyrimidines such as N-(4,6-dimethylpyrimidin-2-yl)aniline, N-[4-methyl-6-(1-propynyl)pyrimidin-2-yl] aniline, N-(4-methyl-6-cyclopropyl-pyrimidin-2-yl)aniline.

Phenylpyrrols such as 4-(2,2-difluoro-1,3-benzodioxol-4-yl)-pyrrol-3-carbonitrile.

Cinnamamides such as 3-(4-chlorophenyl)-3-(3,4-dimethoxyphenyl)acryloylmorpholine.

(2RS,3SR)-1-[3-(2-chlorophenyl)-2-[4-fluorophenyl] oxiran-2-yl-methyl]-1H-1,2,4-triazole.

The protocols shown in the synthesis examples below can be used for obtaining other representatives of the compounds I or II by modifying the starting compounds. The physical data of the resulting products are shown in the tables which follow.

SYNTHESIS EXAMPLES

The chemical shifts (in ppm) of the $^1$H NMR spectra were measured against tetramethylsilane (br=broad signal, s=singulet, d=doublet, m=multiplet).

Example 1

2-[2-(5-Chloro-3-trifluoromethylpyridyl)thio]ethyl 3-chlorobenzoate 18.3 g (0.085 mol) of 2,5-dichloro-3-trifluoromethylpyridine were added to a solution of 5.1 g (0.094 mol) of sodium methanolate and 6.6 g (0.085 mol) of 2-mercaptoethanol in 200 ml of dimethylformamide, whereupon the mixture was stirred for 2 hours at room temperature. The solvent was subsequently distilled off. The residue was poured into 100 ml of water. The mixture was then extracted 3 times using in each case 50 ml of dichloromethane. The combined organic phases were washed three times using in each case 50 ml of water and then dried and finally concentrated. 12 g of 2-(2-hydroxyethylthio)-5-chloro-3-trifluoromethylpyridine remained.

A solution of 7.2 g (0.0415 mol) of 3-chlorobenzoyl chloride in 100 ml of [lacuna] was carefully added dropwise, with ice-cooling to 10.7 g (0.042 mol) of the resulting 2-(2-hydroxyethylthio)-5-chloro-3-trifluoromethylpyridine and 4.3 g (0.0415 mol) of triethylamine in 100 ml of dichloromethane. After the reaction mixture had been stirred for 12 hours at room temperature, it was poured into 100 ml of 10% w/w hydrochloric acid. The mixture was then extracted using 100 ml of dichloromethane. The combined organic phases were washed twice using in each case 50 ml of 10.5% strength aqueous sodium hydrogen carbonate solution and with water and then dried and finally concentrated. The residue was stirred with diisopropyl ether and then separated off. Yield: 10.3 g (62.6%); m.p.:62–66° C.

EXAMPLE 2

2-[2-(5-Chloro-3-trifluoromethylpyridyl)sulfoxy]ethyl 3-chlorobenzoate and 2-[2-(5-chloro-3-trifluoromethylpyridyl)sulfonyl]-ethyl 3-chlorobenzoate.

1.5 g (0.0126 mol) of 30% strength hydrogen peroxide solution were added dropwise at approximately 20° C. to 5 g (0.013 mol) of 2-[2-(5-chloro-3-trifluoromethylpyridyl) thio]ethyl 3-chlorobenzoate and 0.15 g (0.00045 mol) of sodium tungstate in 15 ml of concentrated acetic acid. After the reaction mixture had been stirred for 12 hours at approximately 20° C., it was poured into ice-water. The resulting solids were then separated off and chromatographed on silica gel (eluent: ethyl acetate/cyclohexane=1:1). Yield: first 0.7 g (13%) of 2-(5-chloro-3-trifluoromethylpyridyl) sulfonyl]ethyl 3-chlorobenzoate and then 3.1 g (59.7%) of 2-[2-(5-chloro-3-trifluoromethylpyridyl)sulfoxyl]ethyl 3-chlorobenzoate; m.p.: 108–111° C.

TABLE S1

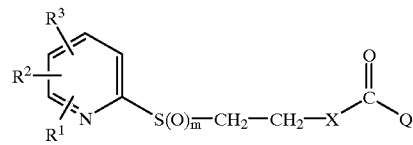

I (A = Al'; Alk = 1, 2-ethylene)

| No. | $R^1$ | $R^2$ | $R^3$ | m | X | Q | Physical data (IR [cm$^{-1}$]; m.p. [° C.]) |
|---|---|---|---|---|---|---|---|
| S1.1 | 5-CF$_3$ | H | H | 0 | —O— | 3-fluorophenyl | oil |
| S1.2 | 5-CF$_3$ | H | H | 1 | —O— | 3-fluorophenyl | 79–81° C. |
| S1.3 | 5-CF$_3$ | H | H | 2 | —O— | 3-fluorophenyl | 91–94° C. |
| S1.4 | 5-CF$_3$ | H | H | 2 | —O— | 3-methylphenyl | 84–86° C. |
| S1.5 | 5-CF$_3$ | H | H | 2 | —O— | 3-(trifluoromethyl)phenyl | 89° C. |
| S1.6 | 5-CF$_3$ | H | H | 2 | —O— | 3-nitrophenyl | 108° C. |
| S1.7 | 5-CF$_3$ | H | H | 2 | —O— | 3-cyanophenyl | 105° C. |
| S1.8 | 5-CF$_3$ | H | H | 2 | —O— | 4-methylphenyl | 107–109° C. |
| S1.9 | 5-CF$_3$ | H | H | 2 | —O— | 2,3-dichlorophenyl | 100–103° C. |
| S1.10 | H | 4-CF$_3$ | H | 0 | —O— | 3-chlorophenyl | oil |
| S1.11 | H | 4-CF$_3$ | H | 1 | —O— | 3-chlorophenyl | 1728, 1383, 1327, 1256, 1145 |
| S1.12 | H | 4-CF$_3$ | H | 2 | —O— | 3-chlorophenyl | 1722, 1325, 1161, 1144, 750 |
| S1.13 | 6-CF$_3$ | H | H | 0 | —O— | 3-chlorophenyl | oil |
| S1.14 | 6-CF$_3$ | H | H | 1 | —O— | 3-chlorophenyl | 55–57° C. |
| S1.15 | 6-CF$_3$ | H | H | 2 | —O— | 3-chlorophenyl | 96–98° C. |
| S1.16 | 5-CF$_3$ | H | 3-Cl | 0 | —O— | 3-chlorophenyl | 62–66° C. |
| S1.17 | 5-CF$_3$ | H | 3-Cl | 1 | —O— | 3-chlorophenyl | 98–101° C. |
| S1.18 | 5-CF$_3$ | H | 3-Cl | 2 | —O— | 3-chlorophenyl | 83° C. |
| S1.19 | 5-CF$_3$ | H | 3-Cl | 2 | —O— | 4-chlorophenyl | 133° C. |
| S1.20 | 5-CF$_3$ | H | 3-Cl | 2 | —O— | 2,3-dichlorophenyl | 125° C. |
| S1.21 | 5-CF$_3$ | H | 3-Cl | 2 | —O— | 3,4-dichlorophenyl | 84–86° C. |
| S1.22 | 5-CF$_3$ | H | 3-Cl | 2 | —O— | 4-methylphenyl | 138–140° C. |
| S1.23 | 5-CF$_3$ | H | 3-Cl | 2 | —O— | 2-methylphenyl | 97–99° C. |
| S1.24 | 6-Cl | 5-CN | H | 0 | —O— | 3-chlorophenyl | 1724, 1576, 1426, 1340, 1256, 1145, 1060, 749 |
| S1.25 | 5-Cl | H | 3-CF$_3$ | 0 | —O— | 3-chlorophenyl | 50–57° C. |
| S1.26 | 5-Cl | H | 3-CF$_3$ | 1 | —O— | 3-chlorophenyl | 108–111° C. |
| S1.27 | 5-Cl | H | 3-CF$_3$ | 2 | —O— | 3-chlorophenyl | oil |
| S1.28 | 6-Cl | 4-CF$_3$ | H | 0 | —O— | 3-chlorophenyl | 1726, 1552, 1366, 1319, 1256, 1179 |
| S1.29 | 6-Cl | 4-CF$_3$ | H | 1 | —O— | 3-chlorophenyl | 1729, 1369, 1318, 1254, 1149 |
| S1.30 | 6-Cl | 4-CF$_3$ | H | 2 | —O— | 3-chlorophenyl | 84–86° C. |
| S1.31 | 6-Cl | 5-CF$_3$ | H | 0 | —O— | 3-chlorophenyl | 1726, 1583, 1350, 1310, 1257, 1149, 1119 |
| S1.32 | 6-Cl | 5-CF$_3$ | H | 1 | —O— | 3-chlorophenyl | 1728, 1575, 1361, 1306, 1255, 1149, 1066, 750 |
| S1.33 | 6-Cl | 5-CF$_3$ | H | 2 | —O— | 3-chlorophenyl | 1730, 1368, 1332, 1308, 1257, 1151 |
| S1.34 | 6-CH$_3$ | 4-CH$_3$ | 3-CN | 0 | —O— | 3-chlorophenyl | 103–105° C. |
| S1.35 | 6-CH$_3$ | 4-CH$_3$ | 3-CN | 1 | —O— | 3-chlorophenyl | oil |

TABLE S1-continued

I (A = Al'; Alk = 1, 2-ethylene)

| No. | R¹ | R² | R³ | m | X | Q | Physical data (IR [cm⁻¹]; m.p. [° C.]) |
|---|---|---|---|---|---|---|---|
| S1.36 | 6-CH₃ | 4-CH₃ | 3-CN | 2 | —O— | 3-chlorophenyl | 105–109° C. |
| S1.37 | 6-CH₃ | 4-CH₃ | 3-CN | 2 | —O— | 3-fluorophenyl | 107–111° C. |
| S1.38 | 6-CH₃ | 4-CH₃ | 3-CN | 2 | —O— | 3-methylphenyl | 92–96° C. |
| S1.39 | 6-CH₃ | 4-CH₃ | 3-CN | 2 | —O— | 3-trifluoromethyl)phenyl | 2220, 1731, 1596, 1336, 1255, 1131, 757 |
| S1.40 | 6-CH₃ | 4-CH₃ | 3-CN | 2 | —O— | 3-methoxyphenyl | 127° C. |
| S1.41 | 6-CH₃ | 4-CH₃ | 3-CN | 2 | —O— | 3-nitrophenyl | 116° C. |
| S1.42 | 6-CH₃ | 4-CH₃ | 3-CN | 2 | —O— | 3-cyanophenyl | 112° C. |
| S1.43 | 6-Cl | H | 3-CN | 0 | —O— | 3-chlorophenyl | 85° C. |
| S1.44 | 6-Cl | H | 3-CN | 2 | —O— | 3-chlorophenyl | oil |
| S1.45 | 6-Cl | H | 3-NO₂ | 0 | —O— | 3-chlorophenyl | 105° C. |
| S1.46 | 6-Cl | H | 3-NO₂ | 1 | —O— | 3-chlorophenyl | 117–119° C. |
| S1.47 | 6-Cl | H | 3-NO₂ | 2 | —O— | 3-chlorophenyl | 129–131° C. |
| S1.48 | 6-Cl | 5-NO₂ | H | 0 | —O— | 3-chlorophenyl | oil |
| S1.49 | 6-Cl | 5-NO₂ | H | 2 | —O— | 3-chlorophenyl | oil |
| S1.50 | 5-CF₃ | H | H | 2 | —O— | 3-chlorophenyl | 94–96 |
| S1.51 | 5-CF₃ | H | H | 0 | —O— | 3-chlorophenyl | oil |
| S1.52 | 5-CF₃ | H | H | 1 | —O— | 3-chlorophenyl | 77–79 |
| S1.53 | H | H | 3-CF₃ | 2 | —O— | 3-chlorophenyl | oil |
| S1.54 | H | H | 3-CF₃ | 2 | —O— | 3-fluorophenyl | oil |
| S1.55 | 5-CF₃ | H | H | 2 | —O— | 3-methoxyphenyl | 73–78 |
| S1.56 | 5-CF₃ | H | 3-Cl | 2 | —O— | 3-chlorophenyl | 82–83 |
| S1.57 | 6-Cl | 4-CF₃ | H | 2 | —O— | 3-methylphenyl | 72–74 |
| S1.58 | 6-Cl | 4-CF₃ | H | 2 | —O— | 3-cyanophenyl | 110–115 |
| S1.59 | 6-CH₃ | 4-CH₃ | 3-CN | 2 | —O— | 3-methylphenyl | 92–96 |
| S1.60 | 6-CH₃ | 4-CH₃ | 3-CN | 2 | —O— | 3-methoxyphenyl | 127 |
| S1.61 | 6-CH₃ | 4-CH₃ | 3-CN | 2 | —O— | 3-trifluoromethylphenyl | oil |
| S1.62 | 6-CH₃ | 4-CH₃ | 3-CN | 2 | —O— | 3-nitrophenyl | 116 |
| S1.63 | 6-CH₃ | 4-CH₃ | 3-CN | 2 | —O— | 3-cyanophenyl | 108–112 |
| S1.64 | 5-CF₃ | H | H | 2 | —NH— | 3-chlorophenyl | 58 |
| S1.65 | 5-CF₃ | H | H | 2 | —NH— | 3-nitrophenyl | 141–145 |
| S1.66 | 5-CF₃ | H | 3-Cl | 2 | —NH— | 3-chlorophenyl | 75–76 |
| S1.67 | 6-CH(CH₃)₂ | 3-CN | H | 2 | —O— | 3-chlorophenyl | 75–77 |
| S1.68 | 6-CH(CH₃)₂ | 3-CN | H | 2 | —O— | 3-cyanophenyl | 74–75 |
| S1.69 | 6-CH(CH₃)₂ | 3-CN | H | 2 | —O— | 3-nitrophenyl | 87 |
| S1.70 | 6-CH(CH₃)₂ | 3-CN | H | 2 | —O— | 3-fluorophenyl | oil |
| S1.71 | 6-Cl | 5-CN | 4-CH₃ | 2 | —O— | 3-chlorophenyl | 137–139 |
| S1.72 | 6-OCH₃ | H | H | 2 | —O— | 3-chlorophenyl | 100–105 |
| S1.73 | 6-Cl | 4-CH₃ | 3-CN | 2 | —O— | 3-chlorophenyl | 100–103 |
| S1.74 | 6-CH₃ | H | H | 2 | —O— | 3-chlorophenyl | 81–86 |
| S1.75 | 4-Cl | 3-NO₂ | H | 2 | —O— | 3-chlorophenyl | 95 |
| S1.76 | H | 3-Cl | 5-CO—NH₂ | 2 | —O— | 3-chlorophenyl | 143 |
| S1.77 | H | 3-Cl | 5-SO₂—CH₃ | 2 | —O— | 3-chlorophenyl | 152 |
| S1.78 | 5-CF₃ | H | H | 0 | —O— | 3-methoxyphenyl | oil |
| S1.79 | 5-CF₃ | H | H | 0 | —NH— | 3-chlorophenyl | 84–85 |
| S1.80 | 6-CH(CH₃)₂ | 3-CN | H | 0 | —O— | 3-fluorophenyl | 85 |
| S1.81 | 6-CH(CH₃)₂ | 3-CN | H | 0 | —O— | 3-nitrophenyl | 75–79 |
| S1.82 | 6-CH(CH₃)₂ | 3-CN | H | 0 | —O— | 3-cyanophenyl | 150 |
| S1.83 | 6-Cl | 4-CH₃ | 3-CN | 0 | —O— | 3-cyanophenyl | 120–122 |
| S1.64 | 4-Cl | 3-NO₂ | H | 0 | —O— | 3-chlorophenyl | 72–74 |
| S1.85 | 6-CH₃ | H | H | 0 | —O— | 3-chlorophenyl | oil |
| S1.86 | H | 3-Cl | 5-SO₂—CH₃ | 0 | —O— | 3-chlorophenyl | 96 |

TABLE S2

I (A = Al'; X = Q)

| No. | R¹ | R² | R³ | Alk | Q | m | Physical data (IR [cm⁻¹]; m.p. [° C.]) |
|---|---|---|---|---|---|---|---|
| S2.1 | 5-CF₃ | H | H | 1,2-propylene | 3-chlorophenyl | 2 | 114° C. |
| S2.2 | 5-CF₃ | H | H | 1,2-propylene | 3-nitrophenyl | 2 | 140° C. |
| S2.3 | 6-CH₃ | 4-CH₃ | 3-CN | 1-methyl-2,3-propylene | 3-chlorophenyl | 0 | oil |
| S2.4 | 5-CF₃ | H | H | —CH₂CH(CH₃)— | 3-chlorophenyl | 2 | 108–114 |
| S2.5 | 5-CF₃ | H | H | —CH₂CH(CH₃)— | 3-nitrophenyl | 2 | 137–140 |
| S2.6 | 5-CF₃ | H | H | —CH₂CH(CH₃)— | 3-cyanophenyl | 2 | 139–145 |
| S2.7 | 5-CF₃ | H | 3-Cl | —CH₂CH(CH₃)— | 3-chlorophenyl | 2 | 98–100 |
| S2.8 | 5-CF₃ | H | 3-Cl | —CH₂CH(CH₃)— | 3-cyanophenyl | 2 | oil |
| S2.9 | 6-Cl | 4CF₃ | H | —CH₂CH(CH₃)— | 3-chlorophenyl | 2 | 92–98 |
| S2.10 | 6-Cl | 4-CF₃ | H | —CH₂CH(CH₃)— | 3-methylphenyl | 2 | 65–70 |
| S2.11 | 6-Cl | 4-CF₃ | H | —CH₂CH(CH₃)— | 3-nitrophenyl | 2 | 128–135 |
| S2.12 | 6-Cl | 4-CF₃ | H | —CH₂CH(CH₃)— | 3-cyanophenyl | 2 | 134–140 |
| S2.13 | 6-CH₃ | 4-CH₃ | 3-CN | —C(CH₃)₂CH₂— | 3-chlorophenyl | 2 | 80–85 |
| S2.14 | 6-CH₃ | 4-CH₃ | 3-CN | —C(CH₃)₂CH₂— | 3-methylphenyl | 2 | 97–100 |
| S2.15 | 6-CH₃ | 4-CH₃ | 3-CN | —C(CH₃)₂CH₂— | 3-chlorophenyl | 0 | oil |

TABLE S3

II (A = Al'; X= O)

| No. | R¹ | R² | R³ | Alk | m | Physical data (¹H NMR (in CDCl₃; pyridine protons) [δ in ppm]; IR [cm⁻¹]) |
|---|---|---|---|---|---|---|
| S3.1 | H | 4-CF₃ | H | 1,2-ethylene | 0 | 7.1; 7.45; 8.55 |
| S3.2 | 6-CF₃ | H | H | 1,2-ethylene | 0 | 7.4; 7.65 |
| S3.3 | 5-Cl | H | 3-CF₃ | 1,2-ethylene | 0 | 7.9; 8.5 |
| S3.4 | 5-CF₃ | H | 3-Cl | 1,2-ethylene | 0 | 7.8; 8.55 |
| S3.5 | 5-CF₃ | H | 3-Cl | 1,2-ethylene | 2 | 8.2; 8.8 |
| S3.6 | 6-Cl | 4-CF₃ | H | 1,2-ethylene | 0 | 7.2; 7.38 |
| 53.7 | 6-Cl | 4-CF₃ | H | 1,2-ethylene | 2 | 7.85; 8.25 |
| S3.8 | 6-CH₃ | 4-CH₃ | 3-CN | 1,2-ethylene | 0 | 6.9 |
| S3.9 | 6-CH₃ | 4-CH₃ | 3-CN | 1,2-ethylene | 2 | 7.45 |
| S3.10 | 6-Cl | H | 3-NO₂ | 1,2-ethylene | 0 | 7.2; 8.26 |
| 53.11 | 6-Cl | 4-CF₃ | H | 1,2-propylene | 0 | 7.2; 7.4 |
| S3.12 | 6-Cl | 4-CF₃ | H | 1,2-propylene | 2 | 7.82; 8.27 |
| S3.13 | 5-CF₃ | H | H | 3-methyl-1,2-propylene | 0 | 7.4; 7.73; 8.65 |
| S3.14 | 5-CF₃ | H | H | 3-methyl-1,2-propylene | 2 | 8.25; 9.05 |
| S3.15 | 5-CF₃ | H | H | 2,3-propylene | 0 | oil |
| S3.16 | 5-CF₃ | H | H | 2,3-propylene | 2 | 8.27; 9.0 |
| S3.17 | 5-CF₃ | H | 3-Cl | 2,3-propylene | 0 | 8.2; 8.85 |
| S3.18 | 6-CH₃ | 4-CH₃ | 3-CN | 1,2-ethylene | 0 | 3400; 2964; 2924; 2210; 1584 |
| S3.19 | 6-Cl | 5-CN | H | 1,2-ethylene | 0 | 7.25; 7.7 |
| S3.20 | 6-Cl | H | 3-CN | 1,2-ethylene | 0 | 3280; 2240; 1562; 1530; 1412; 1340 |

TABLE S4

Structure: R''' on position, R'' and R' on ring with X, fused thiazole with -S(O)ₘ-Alk-O-C(O)-phenyl-R''''

| No. | R' | R'' | R''' | X | m | Alk | R'''' | Physical data (¹H NMR [ppm]; m.p. [° C.]) |
|---|---|---|---|---|---|---|---|---|
| S4.1 | H | H | H | CH | 0 | 1,2-ethylidene | 3-Cl | 8.0–7.3; 4.7; 3.7 |
| S4.2 | H | Cl | H | CH | 0 | 1,2-ethylidene | 3-Cl | 8.0–7.2; 4.7; 3.7 |
| S4.3 | H | Cl | H | CH | 0 | 1,2-ethylidene | 2-Cl | 4.7; 3.6 |
| S4.4 | H | Cl | H | CH | 0 | 1,2-ethylidene | 4-Cl | 4.7; 3.6 |
| S4.5 | H | CF₃ | H | CH | 2 | 1,2-ethylidene | 3-Cl | 128 |
| S4.6 | H | H | H | CH | 2 | 1,2-ethylidene | 3-Cl | 95 |
| S4.7 | H | Cl | H | CH | 2 | 1,2-ethylidene | 2-Cl | 172 |
| S4.8 | H | Cl | H | CH | 2 | 1,2-ethylidene | 4-Cl | >200 |
| S4.9 | H | CF₃ | H | CH | 2 | 1,2-ethylidene | 2-Cl | 164 |
| S4.10 | H | CF₃ | H | CH | 2 | 1,2-ethylidene | 4-Cl | 165 |
| S4.11 | H | Cl | H | CH | 2 | 1,2-ethylidene | 3-Cl | 152 |
| S4.12 | H | Cl | H | CH | 2 | 1,2-ethylidene | 3-F | 148–50 |
| S4.13 | H | H | H | CH | 1 | 1,2-ethylidene | 3-CN | 97–106 |
| S4.14 | H | Cl | H | CH | 1 | 1,2-ethylidene | 3-CH₃ | 140–50 |
| S4.15 | H | Cl | H | CH | 2 | 1,2-ethylidene | 3-CH₃ | 130–5 |
| S4.16 | H | H | Cl | CH | 2 | 1,2-ethylidene | 2-Cl | 90 |
| S4.17 | H | H | Cl | CH | 2 | 1,2-ethylidene | 3-Cl | 85 |
| S4.18 | H | H | Cl | CH | 2 | 1,2-ethylidene | 4-Cl | 145 |
| S4.19 | H | Cl | H | N | 2 | 1,2-ethylidene | 2-Cl | 155–60 |
| S4.20 | H | Cl | H | N | 2 | 1,2-ethylidene | 3-Cl | 155–62 |
| S4.21 | H | Cl | H | N | 2 | 1,2-ethylidene | 4-Cl | 195–99 |
| S4.22 | H | Cl | H | CH | 0 | 1,2-ethylidene | 3-NO₂ | 4.7; 3.6 |
| S4.23 | H | Cl | H | CH | 2 | 1,2-ethylidene | 3-NO₂ | 95–105 |
| S4.24 | H | H | H | CH | 2 | 1,2-ethylidene | 3-NO₂ | 130–35 |
| S4.25 | Cl | H | H | CH | 2 | 1,2-ethylidene | 3-NO₂ | 126–30 |
| S4.26 | Cl | H | H | CH | 2 | 1,2-ethylidene | 3-CN | 124 |
| S4.27 | H | Cl | H | CH | 2 | 1,2-ethylidene | 3-CN | 157–60 |
| S4.28 | H | H | H | CH | 2 | 1,2-ethylidene | 3-CN | 94–110 |
| S4.29 | H | H | H | N | 2 | 1,2-ethylidene | 3-Cl | 161 |
| S4.30 | H | H | H | N | 2 | 1,2-ethylidene | 2-Cl | 105–8 |
| S4.31 | H | H | H | N⁺—O⁻ | 2 | 1,2-ethylidene | 3-Cl | 110 |
| S4.32 | H | H | H | N⁺—O⁻ | 2 | 1,2-ethylidene | 2-Cl | 174-5 |
| S4.33 | H | Cl | H | CH | 0 | 1,2-ethylidene | 3-F | 4.7; 3.6 |
| S4.34 | H | H | H | CH | 0 | 1,2-ethylidene | 3-CN | 4.7; 3.6 |
| S4.35 | CH₃ | H | H | CH | 0 | 1,2-ethylidene | 3-Cl | 4.7; 3.6 |
| S4.36 | OEt | H | H | CH | 0 | 1,2-ethylidene | 3-Cl | 4.7; 3.6 |
| S4.37 | CH₃ | H | H | CH | 2 | 1,2-ethylidene | 3-NO₂ | 160–5 |
| S4.38 | CH₃ | H | H | CH | 2 | 1,2-ethylidene | 3-CN | 127–32 |
| S4.39 | CH₃ | H | H | CH | 2 | 1,2-ethylidene | 3-Cl | 108–11 |
| S4.40 | OEt | H | H | CH | 2 | 1,2-ethylidene | 3-CN | 95–100 |
| S4.41 | OEt | H | H | CH | 2 | 1,2-ethylidene | 3-NO₂ | 140–5 |
| S4.42 | OEt | H | H | CH | 2 | 1,2-ethylidene | 3-Cl | 90–5 |
| S4.43 | F | H | Cl | CH | 2 | 1,2-ethylidene | 3-Cl | 110 |
| S4.44 | H | H | H | N⁺—O⁻ | 2 | 1,2-ethylidene | 3-NO₂ | 115–20 |

TABLE S5

Structure: Pyrimidine with R', R'', R''' substituents, -S(O)ₘ-Alk-O-C(O)-phenyl-R''''

| No. | R' | R'' | R''' | m | Alk | R'''' | Physical data (¹H NMR [ppm]; m.p. [° C.]) |
|---|---|---|---|---|---|---|---|
| S5.1 | H | CH₃ | H | 0 | 1,2-ethylidene | 3-Cl | 8.4; 4.7; 2.2 |
| S5.2 | H | CH₃ | H | 0 | 1,2-ethylidene | 2-Cl | 8.4; 7.8; 3.6; 2.3 |

TABLE S5-continued

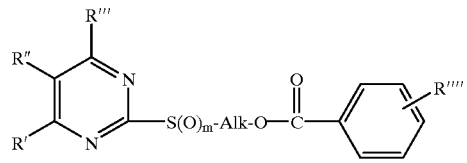

| No. | R' | R" | R''' | m | Alk | R'''' | Physical data ($^1$H NMR [ppm]; m.p. [° C.]) |
|---|---|---|---|---|---|---|---|
| S5.3 | H | CH$_3$ | H | 0 | 1,2-ethylidene | 4-Cl | 8.4; 8.0; 4.6; 2.3 |
| S5.4 | H | CH$_3$ | H | 2 | 1,2-ethylidene | 3-Cl | 98–100 |
| S5.5 | H | CH$_3$ | H | 2 | 1,2-ethylidene | 2-Cl | 102 |
| S5.6 | H | CH$_3$ | H | 2 | 1,2-ethylidene | 4-Cl | 178–80 |
| S5.7 | H | CH$_3$ | H | 0 | CH$_2$CH(CH$_3$) | 2-Cl | 8.4; 5.4; 3.6; 3.4; 2.2; 1.5 |
| S5.8 | H | CH$_3$ | H | 0 | CH$_2$CH(CH$_3$) | 3-Cl | 8.3; 5.4; 1.5 |
| S5.9 | H | CH$_3$ | H | 0 | CH$_2$CH(CH$_3$) | 4-Ckl | 8.3; 5.4; 3.6; 2.2; 1.5 |
| S5.10 | H | CH$_3$ | H | 0 | CH$_2$CH(CH$_3$) | 2,4-Cl$_2$ | 8.4; 7.8; 5.4; 1.5 |
| S5.11 | CH$_3$ | H | H | 0 | 1,2-ethylidene | 2-Cl | 8.4; 7.9; 6.8; 2.4 |
| S5.12 | CH$_3$ | H | H | 0 | 1,2-ethylidene | 3-Cl | 8.4; 6.8; 4.6; 3.6 |
| S5.13 | CH$_3$ | H | H | 0 | 1,2-ethylidene | 4-Cl | 8.4; 8.0; 3.6 |
| S5.14 | CH$_3$ | H | H | 0 | 1,3-propylidene | 2-Cl | 8.4; 4.5; 3.3; 2.4; 2.2 |
| S5.15 | CH$_3$ | H | H | 0 | 1,3-propylidene | 3-Cl | 8.4; 8.1; 8.0; 2.4; 2.2 |
| S5.16 | CH$_3$ | H | H | 0 | 1,3-propylidene | 4-Cl | 8.5; 8.0; 2.2 |
| S5.17 | CH$_3$ | H | H | 0 | CH$_2$CH(CH$_3$) | 2-Cl | 8.4; 6.8; 3.6; 3.4; 1.5 |
| S5.18 | CH$_3$ | H | H | 0 | CH$_2$CH(CH$_3$) | 3-Cl | 8.4; 6.8; 3.6; 3.4 |
| S5.19 | CH$_3$ | H | H | 0 | CH$_2$CH(CH$_3$) | 4-Cl | 8.4; 6.8; 3.7; 3.4; 2.4 |
| S5.20 | CH$_3$ | H | H | 0 | CH$_2$C(CH$_3$)$_2$CH$_2$ | 3-Cl | 8.3; 4.2; 3.5; 2.4; 1.1 |
| S5.21 | CH$_3$ | H | H | 0 | CH$_2$C(CH$_3$)$_2$CH$_2$ | 2-Cl | 8.3; 4.2; 3.5; 2.4; 1.2 |
| S5.22 | H | H | H | 0 | 1,2-ethylidene | 2-Cl | 8.6; 7.0; 4.6; 3.5 |
| S5.23 | H | H | H | 0 | 1,2-ethylidene | 3-Cl | 8.6; 8.9; 7.0; 4.6 |
| S5.24 | H | H | H | 0 | 1,2-ethylidene | 4-Cl | 8.5; 8.0; 4.6; 3.6 |
| S5.25 | H | H | H | 0 | 1,2-ethylidene | 2,4-Cl$_2$ | 8.5; 4.6; 3.6 |
| S5.26 | H | CH$_3$ | H | 2 | CH$_2$CH(CH$_3$) | 4-Cl | 128 |
| S5.27 | H | CH$_3$ | H | 2 | CH$_2$CH(CH$_3$) | 3-Cl | 134 |
| S5.28 | CH$_3$ | H | H | 2 | 1,2-ethylidene | 3-Cl | 82 |
| S5.29 | CH$_3$ | H | H | 2 | 1,2-ethylidene | 4-Cl | 130 |
| S5.30 | CH$_3$ | H | H | 2 | 1,3-propylidene | 2-Cl | 8.8; 4.5; 3.8; 2.7; 2.4 |
| S5.31 | CH$_3$ | H | H | 2 | 1,3-propylidene | 3-Cl | 8.8; 4.5 |
| S5.32 | CH$_3$ | H | H | 2 | 1,3-propylidene | 3-Cl | 8.8; 4.5; 2.4 |
| S5.33 | CH$_3$ | H | H | 2 | CH$_2$C(CH$_3$)$_2$CH$_2$ | 3-Cl | 8.8; 4.3; 2.7; 2.6; 1.3 |
| S5.34 | H | H | H | 2 | 1,2-ethylidene | 2-Cl | 132-4 |
| S5.35 | H | H | H | 2 | 1,2-ethylidene | 3-Cl | 124-6 |
| S5.36 | H | H | H | 2 | 1,2-ethylidene | 4-Cl | 115-8 |
| S5.37 | H | H | H | 2 | 1,2-ethylidene | 2,4-Cl$_2$ | 94 |
| S5.38 | H | CH$_3$ | H | 2 | CH$_2$CH(CH$_3$) | 2-Cl | 8.6; 4.1; 3.7; 1.5 |
| S5.39 | H | H | H | 0 | 1,3-propylidene | 2-Cl | 8.5; 7.9; 4.5; 3.3; 2.3 |
| S5.40 | H | H | H | 0 | 1,3-propylidene | 3-Cl | 8.5; 4.4; 3.3; 2.2 |
| S5.41 | H | H | H | 0 | CH$_2$C(CH$_3$)$_2$CH$_2$ | 2-Cl | 8.5; 4.2; 3.3; 1.2 |
| S5.42 | H | H | H | 0 | CH$_2$C(CH$_3$)$_2$CH$_2$ | 3-Cl | 8.5; 6.9; 4.2; 3.4; 1.1 |
| S5.43 | H | H | H | 0 | CH$_2$C(CH$_3$)$_2$CH$_2$ | 4-Cl | 8.5; 8.0; 3.4; 1.2 |
| S5.44 | H | H | H | 0 | CH$_2$C(CH$_3$)$_2$CH$_2$ | 2,4-Cl$_2$ | 8.5; 6.9; 4.2; |

TABLE S5-continued

| No. | R' | R'' | R''' | m | Alk | R'''' | Physical data (¹H NMR [ppm]; m.p. [° C.]) |
|---|---|---|---|---|---|---|---|
| S5.45 | H | H | H | 0 | $CH_2CH(CH_3)$ | 2-Cl | 3.4; 1.2 8.5; 3.4; 1.5 |
| S5.46 | H | H | H | 0 | $CH_2CH(CH_3)$ | 3-Cl | 8.5; 5.4; 3.4; 1.5 |
| S5.47 | H | H | H | 0 | $CH_2CH(CH_3)$ | 4-Cl | 8.5; 7.0; 1.5 |
| S5.48 | H | $CH_3$ | H | 2 | $CH_2CH(CH_3)$ | 2,4-$Cl_2$ | 138 |
| S5.49 | $CH_3$ | H | H | 2 | $CH_2CH(CH_3)$ | 2-Cl | 8.6; 5.6; 4.1; 2.5; 1.6 |
| S5.50 | $CH_3$ | H | H | 2 | $CH_2CH(CH_3)$ | 3-Cl | 55–60 |
| S5.51 | H | H | H | 2 | $CH_2CH(CH_3)$ | 2-Cl | 143 |
| S5.52 | H | H | H | 2 | $CH_2CH(CH_3)$ | 3-Cl | 85 |
| S5.53 | H | H | H | 2 | $CH_2CH(CH_3)$ | 4-Cl | 90 |
| S5.54 | H | H | H | 2 | 1,3-propylidene | 2-Cl | 9.0; 8.0; 4.5; 3.7 |
| S5.55 | H | H | H | 2 | 1,3-propylidene | 3-Cl | 102 |
| S5.56 | H | H | H | 2 | $CH_2C(CH_3)_2CH_2$ | 2-Cl | 9.0; 4.3; 3.7; 1.3 |
| S5.57 | H | H | H | 2 | $CH_2C(CH_3)_2CH_2$ | 3-Cl | 65–70 |
| S5.58 | H | H | H | 2 | $CH_2C(CH_3)_2CH_2$ | 4-Cl | 132 |
| S5.59 | H | H | H | 2 | $CH_2C(CH_3)_2CH_2$ | 2,4-$Cl_2$ | 108 |
| S5.60 | H | $CH_3$ | H | 0 | 1,2-ethylidene | 3-CN | 8.4; 8.3; 4.6; 3.5 |
| S5.61 | $CH_3$ | H | H | 0 | 1,2-ethylidene | 3-F | 8.3; 6.8; 2.4 |
| S5.62 | H | $CH_3$ | H | 0 | 1,2-ethylidene | 3-F | 8.4; 7.8; 4.6; 2.2 |
| S5.63 | $CH_3$ | CH | H | 0 | 1,3-propylidene | 3-F | 8.4; 4.5; 3.2 |
| S5.64 | H | $CH_3$ | H | 2 | 1,2-ethylidene | 3-CN | 100–3 |
| S5.65 | H | $CH_3$ | H | 2 | 1,2-ethylidene | 3-F | 8.6; 3.5; 2.3 |
| S5.66 | $CH_3$ | H | H | 2 | 1,2-ethylidene | 3-F | 8.6; 4.8; 4.0; 2.5 |
| S5.67 | $CH_3$ | H | H | 1 | 1,2-ethylidene | 3-F | 8.6; 4.9; 4.7; 3.6 |

TABLE S6

| No. | R' | R'' | R''' | m | Alk | R'''' | Physical data (¹H NMR [ppm]; m.p. [° C.]) |
|---|---|---|---|---|---|---|---|
| S6.1 | $CH_3$ | $CF_3$ | H | 0 | 1,2-ethylidene | 2-Cl | oil |
| S6.2 | $CH_3$ | $CF_3$ | H | 0 | 1,2-ethylidene | 3-Cl | 8.0; 4.6; 3.4 |
| S6.3 | $CH_3$ | $CF_3$ | H | 0 | 1,3-propylidene | 3-Cl | 8.0; 7.9; 4.5; 3.4; 2.7 |
| S6.4 | $CH_3$ | $CF_3$ | H | 2 | $CH_2CH(CH_3)$ | 3-Cl | 110 |
| S6.5 | $CH_3$ | $CF_3$ | H | 2 | 1,2-ethylidene | 3-$NO_2$ | 100–4 |
| S6.6 | $CH_3$ | $CF_3$ | H | 2 | 1,2-ethylidene | 3-CN | 122–4 |
| S6.7 | $CH_3$ | $CF_3$ | H | 2 | 1,2-ethylidene | 3-Cl | oil |
| S6.8 | H | Cl | H | 2 | 1,2-ethylidene | 3-$NO_2$ | 125–30 |
| S6.9 | H | Cl | H | 2 | 1,2-ethylidene | 3-CN | 122–8 |
| S6.10 | H | Cl | H | 2 | 1,2-ethylidene | 3-Cl | 105–8 |
| S6.11 | $C(CH_3)_3$ | $CF_3$ | H | 2 | 1,2-ethylidene | 3-$NO_2$ | 68 |
| S6.12 | $C(CH_3)_3$ | $CF_3$ | H | 2 | 1,2-ethylidene | 3-CN | 118 |
| S6.13 | $C(CH_3)_3$ | $CF_3$ | H | 2 | 1,2-ethylidene | 3-Cl | 88 |
| S6.14 | H | Cl | H | 2 | 1,3-propylidene | 3-CN | 90–3 |

TABLE S6-continued

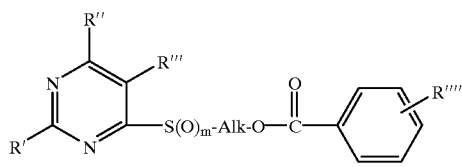

| No. | R' | R" | R'" | m | Alk | R"" | Physical data (¹H NMR [ppm]; m.p. [° C.]) |
|---|---|---|---|---|---|---|---|
| S6.15 | H | Cl | H | 2 | 1,3-propylidene | 3-Cl | oil |
| S6.16 | H | Cl | H | 2 | 1,3-propylidene | 3-NO₂ | 109–13 |
| S6.17 | H | Cl | H | 2 | CH₂CH(CH₃) | 3-NO₂ | 117–21 |
| S6.18 | H | Cl | H | 2 | CH₂CH(CH₃) | 3-CN | 145–8 |
| S6.19 | H | Cl | H | 2 | CH₂CH(CH₃) | 3-Cl | 75–8 |

TABLE S7

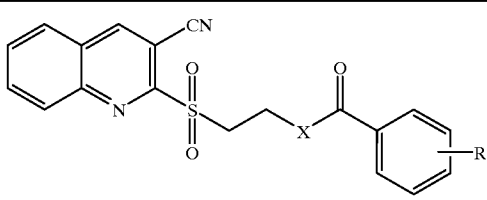

| No. | X | R | M.p. [° C.] |
|---|---|---|---|
| S7.1 | NH | 3-NO₂ | 164–166 |
| S7.2 | NH | 3-F | 175–177 |
| S7.3 | NH | 3-Cl | 155–157 |
| S7.4 | O | 3-F | 134–135 |
| S7.5 | O | 3-Me | 128–130 |
| S7.6 | O | 3-NO₂ | 154 |
| S7.7 | O | 4-Cl | 142–145 |
| S7.8 | O | 3-Cl | 138–139 |
| S7.9 | O | 2-Cl | 148–149 |

Use example

Activity against Plasmopara viticola

Leaves of grapevine cv. "Müller-Thurgau" in pots were sprayed with an aqueous spray mixture comprising 80% by weight of active ingredient and 20% by weight of emulsifier in the dry matter. To be able to assess the duration of action of the active ingredients, the plants were placed in the greenhouse for 8 days after the spray coating had dried. Only then were the leaves infected with a zoospore suspension of *Plasmopara viticola* (downy mildew of grapevine). The grapevines were then placed for 48 hours into a chamber at 24° C. and saturated atmospheric humidity and then for 5 days in a greenhouse at from 20 to 30° C. After this time, the plants were returned into the humid chamber for 16 hours to accelerate eruption of the sporangiophores. The extent of fungal eruption was then assessed on the underside of the leaves.

In comparison with the control experiment (no treatment, fungal eruption 70%), the plants treated with 250 ppm of the following active ingredients only showed a foliar disease level of 0 to 15%:

V7, V8, V16, V18, V19, S1.25, S1.30, S1.12, S1.36, S1.15, S1.27, S1.22, S1.23, S1.19, S1.20, S1.21, S1.47, S1.49, S1.44, S1.46, S1.3, S1.4, S1.5, S1.6, S1.7, S1.8, S1.9. S1.18.

The same amount of the known compound 2,3,5,6-tetrachloro-4-(methylsulfonyl)pyridine

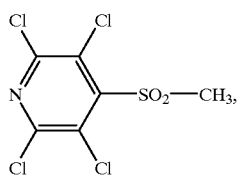

which was also tested for comparison reasons, only caused a reduction in fungal eruption to 40%.

We claim:

1. An N-heterocyclic compound of the formula I

(I)

or a salt or N-oxide thereof, where the variables have the following meanings:

A is an N-heterocycle selected from the group consisting of (A1)

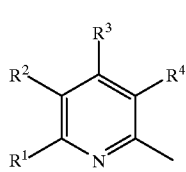

(A8)

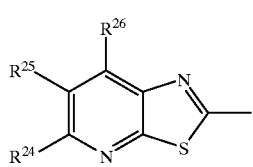

-continued (A9)

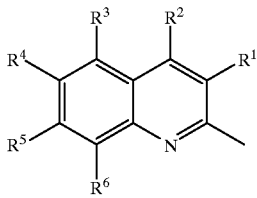

where the groups

R$^1$ to R$^6$ and R$^{24}$ to R$^{26}$ independently of one another are: hydrogen, cyano, nitro, halogen, aminocarbonyl, methylsulfonyl, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkoxy-C$_1$–C$_4$-alkyl, (C$_1$–C$_4$-alkoxy)carbonyl, aryl or aryloxy, where the aryl rings may carry one to three groups selected from: cyano, nitro, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkoxy-C$_1$–C$_4$-alkyl, (C$_1$–C$_4$-alkoxy)carbonyl and C$_1$–C$_4$-acyl;

m is 0, 1 or 2;

Alk is 1,2-ethylidene or 1,3-propylidene, where the hydrogen atoms of these chains may be replaced independently of one another by one of the following groups: C$_1$–C$_8$-alkyl, C$_1$–C$_8$-haloalkyl, C$_2$–C$_8$-alkenyl, C$_2$–C$_8$-haloalkenyl or C$_2$–C$_8$-alkynyl, where each of these 5 radicals additionally may carry one to three groups selected from: cyano, C$_1$–C$_4$-alkoxy, C$_1$–C$_4$-haloalkoxy, C$_1$–C$_4$-alkylthio, (C$_1$–C$_4$-alkoxy)carbonyl, C$_3$–C$_7$-cycloalkyl and C$_5$–C$_7$-cycloalkenyl; C$_3$–C$_7$-cycloalkyl and C$_5$–C$_7$-cycloalkenyl, where these radicals may be partially or fully halogenated or may carry one to three groups selected from: cyano, halogen, C$_1$–C$_4$-alkyl, C$_1$–C$_4$-haloalkyl and C$_1$–C$_4$-alkoxy;

X is oxygen or sulfur;

Q is aryl, which may carry one to three groups selected from: cyano, nitro, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkoxy-C$_1$–C$_4$-alkyl, (C$_1$–C$_4$-alkoxy)carbonyl, C$_1$–C$_4$-acyl, C$_1$–C$_4$-alkylsulfinyl, C$_1$–C$_4$-alkylsulfonyl, aryl and aryloxy, where these aryl rings, in turn, additionally may carry one to three substituents selected from: cyano, nitro, halogen, C$_1$–C$_4$-alkyl, C$_1$–C$_4$-alkoxy-C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, (C$_1$–C$_4$-alkoxy)carbonyl and C$_1$–C$_4$-acyl;

C$_3$–C$_7$-cycloalkyl and C$_5$–C$_7$-cycloalkenyl, where these rings may be partially or fully halogenated or may carry one to three groups selected from: cyano, halogen, C$_1$–C$_4$-alkyl, C$_1$–C$_4$-haloalkyl, C$_1$–C$_4$-alkoxy-C$_1$–C$_4$-alkyl, C$_1$–C$_4$-alkoxy, C$_1$–C$_4$-haloalkoxy, C$_1$–C$_4$-alkylthio, (C$_1$–C$_4$-alkoxy)carbonyl, C$_3$–C$_7$-cycloalkyl, C$_5$–C$_7$-cycloalkenyl, aryl and aryloxy, where these aryl rings, in turn, additionally may carry one to three substituents selected from: cyano, nitro, halogen, C$_1$–C$_4$-alkyl, C$_1$–C$_4$-haloalkyl, C$_1$–C$_4$-alkoxy-C$_1$–C$_4$-alkyl, C$_1$–C$_4$-alkoxy, C$_1$–C$_4$-haloalkoxy, C$_1$–C$_4$-alkylthio, (C$_1$–C$_4$-alkoxy)carbonyl and C$_1$–C$_4$-acyl;

aryl-C$_1$–C$_4$-alkyl, where the aryl ring may carry one to three groups selected from: cyano, nitro, halogen, C$_1$–C$_4$-alkyl, C$_1$–C$_4$-haloalkyl, C$_1$–C$_4$-alkoxy-C$_1$–C$_4$-alkyl, C$_1$–C$_4$-alkoxy, C$_1$–C$_4$-haloalkoxy, C$_1$–C$_4$-alkylthio, (C$_1$–C$_4$-alkoxy)carbonyl, C$_1$–C$_4$-acyl, aryl and aryloxy, where these aryl rings, in turn, additionally may carry one to three substituents selected from: cyano, nitro, halogen, C$_1$–C$_4$-alkyl, C$_1$–C$_4$-haloalkyl, C$_1$–C$_4$-alkoxy-C$_1$–C$_4$-alkyl, C$_1$–C$_4$-alkoxy, C$_1$–C$_4$-haloalkoxy, C$_1$–C$_4$-alkylthio, (C$_1$–C$_4$-alkoxy)carbonyl, C$_1$–C$_4$-alkyl, C$_1$–C$_4$-alkoxy, C$_1$–C$_4$-haloalkoxy, C$_1$–C$_4$-alkylthio, (C$_1$–C$_4$-alkoxy)carbonyl and C$_1$–C$_4$-acyl;

with the exception of a) the compounds V1 to V25 where A is A1 and R$^4$ is H:

| No. | R$^1$ | R$^2$ | R$^3$ | m | Alk | X | Q |
|---|---|---|---|---|---|---|---|
| V1 | H | H | H | 0 | 1,2-ethylidene | —O— | phenyl |
| V2 | H | H | H | 2 | 1,2-ethylidene | —O— | phenyl |
| V3 | 5-CF$_3$ | H | H | 0 | 1,2-ethylidene | —O— | 4-chlorophenyl |
| V4 | 5-CF$_3$ | H | H | 0 | 1,2-ethylidene | —O— | 4-methylphenyl |
| V5 | 5-CF$_3$ | H | H | 2 | 1,2-ethylidene | —O— | phenyl |
| V6 | 5-CF$_3$ | H | H | 2 | 1,2-ethylidene | —O— | 2-chlorophenyl |
| V7 | 5-CF$_3$ | H | H | 2 | 1,2-ethylidene | —O— | 3-chlorophenyl |
| V8 | 5-CF$_3$ | H | H | 2 | 1,2-ethylidene | —O— | 4-chlorophenyl |
| V9 | 5-CF$_3$ | H | H | 2 | 1,2-ethylidene | —O— | 3,4-dichlorophenyl |
| V10 | 5-CF$_3$ | H | H | 2 | 1,2-ethylidene | —O— | 4-methylphenyl |
| V11 | 5-CF$_3$ | H | H | 2 | 1,2-ethylidene | —O— | 4-methoxyphenyl |
| V12 | 5-CF$_3$ | H | H | 2 | 1,2-ethylidene | —O— | 4-trifluoromethylphenyl |
| V13 | 5-CF$_3$ | H | H | 2 | 1,2-ethylidene | —O— | 4-tert-butylphenyl |
| V14 | H | H | H | 2 | 1,2-ethylidene | —O— | 3-chlorophenyl |
| V15 | H | H | 3-Cl | 2 | 1,2-ethylidene | —O— | 3-chlorophenyl |
| V16 | 5-Cl | H | H | 2 | 1,2-ethylidene | —O— | 3-chlorophenyl |
| V17 | 6-Cl | H | H | 2 | 1,2-ethylidene | —O— | 3-chlorophenyl |
| V18 | H | H | 3-CN | 2 | 1,2-ethylidene | —O— | 3-chlorophenyl |
| V19 | H | H | 3-CF$_3$ | 2 | 1,2-ethylidene | —O— | 3-chlorophenyl |
| V20 | H | H | 3-NO$_2$ | 2 | 1,2-ethylidene | —O— | 3-chlorophenyl |
| V21 | 5-NO$_2$ | H | H | 2 | 1,2-ethylidene | —O— | 3-chlorophenyl |
| V22 | 6-CH$_3$ | H | H | 2 | 1,2-ethylidene | —O— | 3-chlorophenyl |
| V23 | 6-OCH$_3$ | H | H | 2 | 1,2-ethylidene | —O— | 3-chlorophenyl |
| V24 | 5-COOCH$_3$ | H | H | 2 | 1,2-ethylidene | —O— | 3-chlorophenyl |
| V25 | 6-CH$_3$ | 4-CF$_3$ | H | 2 | 1,2-ethylidene | —O— | 3-chlorophenyl | b) the compound I where A is the N-oxide A1, and where R$^1$, R$^2$, R$^3$, R$^4$ are H; m is 2, Alk is 1,2-ethylidene; X is —O—; Q is phenyl.

2. The N-heterocyclic compound of the formula I or the salt or N-oxide thereof as defined in claim 1, where A is A1'

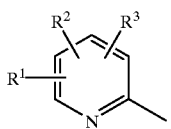
(A1')

with the exception of the compounds mentioned in claim 1 under (a) and (b).

3. A composition suitable for controlling harmful fungi, comprising at least one formulation auxiliary and an effective amount of a compound of the formula I or a salt or N-oxide thereof as defined in claim 1.

4. A method for controlling harmful fungi, which comprises treating the harmful fungi, their environment, or the plants, seeds, areas, materials or spaces to be kept free from said fungi, with an effective amount of a compound of the formula I or a salt or N-oxide thereof as defined in claim 1.

5. The N-heterocyclic compound of the formula I or the salt or N-oxide thereof as defined in claim 1, wherein Q is phenyl which is unsubstituted or carries one to three groups selected from: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxy-$C_1$–$C_4$-alkyl, ($C_1$–$C_4$-alkoxy)carbonyl, $C_1$–$C_4$-acyl, $C_1$–$C_4$-alkylsulfinyl, $C_1$–$C_4$-alkylsulfonyl, phenyl and phenoxy, where these phenyl rings, in turn, additionally may carry one to three substituents selected from: cyano, nitro, halogen, $C_1$–$C_4$-alkyl, $C_1$–$C_4$-alkoxy-$C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, ($C_1$–$C_4$-alkoxy)carbonyl and $C_1$–$C_4$-acyl.

6. The N-heterocyclic compound of the formula I or the salt or N-oxide thereof as defined in claim 1, wherein Q is phenyl which is unsubstituted or carries one to three groups selected from: halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl and phenoxy, where these phenyl rings, in turn, are unsubstituted or carry one to three substituents selected from: halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

7. The N-heterocylic compound of the formula I or the salt or N-oxide thereof as defined in claim 1, wherein Q is phenyl which is unsubstituted or carries one to three groups selected from: fluoro, chloro, bromo, $C_1$–$C_4$-alkyl, $C_1$–$C_2$-haloalkyl, methoxy, ethoxy, trifluoromethoxy, $C_1$–$C_4$-alkylthio, phenyl and phenoxy.

8. The N-heterocyclic compound of the formula I or the salt or N-oxide thereof as defined in claim 7, wherein the phenyl group in the position of Q is unsubstituted or carries one or two halogen atoms and at least one group in the 3-position of the ring.

9. The N-heterocyclic compound of the formula I or the salt or N-oxide thereof as defined in claim 1, wherein Q is phenyl which is unsubstituted or carries one or two substituents selected from: fluoro, chloro and bromo.

10. The composition defined in claim 3, wherein Q is phenyl which is unsubstituted or carries one to three groups selected from: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxy-$C_1$–$C_4$-alkyl, ($C_1$–$C_4$-alkoxy)carbonyl, $C_1$–$C_4$-acyl, $C_1$–$C_4$-alkylsulfinyl, $C_1$–$C_4$-alkylsulfonyl, phenyl and phenoxy, where these phenyl rings, in turn, additionally may carry one to three substituents selected from: cyano, nitro, halogen, $C_1$–$C_4$-alkyl, $C_1$–$C_4$-alkoxy-$C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, ($C_1$–$C_4$-alkoxy)carbonyl and $C_1$–$C_4$-acyl.

11. The composition defined in claim 3, wherein Q is phenyl which is unsubstituted or carries one to three groups selected from: halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl and phenoxy, where these phenyl rings, in turn, are unsubstituted or carry one to three substituents selected from: halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

12. The composition defined in claim 3, wherein Q is phenyl which is unsubstituted or carries one to three groups selected from: fluoro, chloro, bromo, $C_1$–$C_4$-alkyl, $C_1$–$C_2$-haloalkyl, methoxy, ethoxy, trifluoromethoxy, $C_1$–$C_4$-alkylthio, phenyl and phenoxy.

13. The composition defined in claim 12, wherein the phenyl group in the position of Q is unsubstituted or carries one or two halogen atoms and at least one group in the 3-position of the ring.

14. The composition defined in claim 3, wherein Q is phenyl which is unsubstituted or carries one or two substituents selected from: fluoro, chloro and bromo.

15. The method defined in claim 4, wherein Q is phenyl which is unsubstituted or carries one to three groups selected from: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxy-$C_1$–$C_4$-alkyl, ($C_1$–$C_4$-alkoxy)carbonyl, $C_1$–$C_4$-acyl, $C_1$–$C_4$-alkylsulfinyl, $C_1$–$C_4$-alkylsulfonyl, phenyl and phenoxy, where these phenyl rings, in turn, additionally may carry one to three substituents selected from: cyano, nitro, halogen, $C_1$–$C_4$-alkyl, $C_1$–$C_4$-alkoxy-$C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, ($C_1$–$C_4$-alkoxy)carbonyl and $C_1$–$C_4$-acyl.

16. The method defined in claim 4, wherein Q is phenyl which is unsubstituted or carries one to three groups selected from: halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl and phenoxy, where these phenyl rings, in turn, are unsubstituted or carry one to three substituents selected from: halogen, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

17. The method defined in claim 4, wherein Q is phenyl which is unsubstituted or carries one to three groups selected from: fluoro, chloro, bromo, $C_1$–$C_4$-alkyl, $C_1$–$C_2$-haloalkyl, methoxy, ethoxy, trifluoromethoxy, $C_1$–$C_4$-alkylthio, phenyl and phenoxy.

18. The method defined in claim 17, wherein the phenyl group in the position of Q is unsubstituted or carries one or two halogen atoms and at least one group in the 3-position of the ring.

19. The method defined in claim 4, wherein Q is phenyl which is unsubstituted or carries one or two substituents selected from: fluoro, chloro and bromo.

20. A compound of the formula II $$A\text{—}S(O)_m\text{—}Alk\text{—}XH \qquad (II)$$

or a salt or N-oxide thereof, where the variables have the following meanings:

A is an N-heterocycle selected from the group consisting of

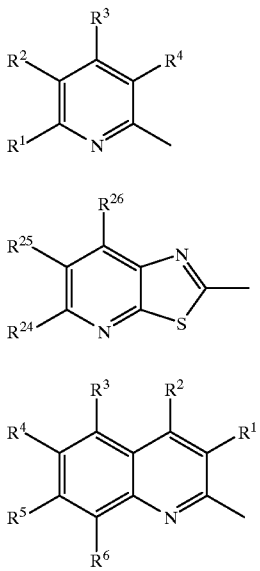

(A1)

(A8)

(A9)

where the groups

R$^1$ to R$^6$ and R$^{24}$ to R$^{26}$ independently of one another are: hydrogen, cyano, nitro, halogen, aminocarbonyl, methylsulfonyl, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkoxy-C$_1$–C$_4$-alkyl, (C$_1$–C$_4$-alkoxy)carbonyl, aryl or aryloxy, where the aryl rings may carry one to three groups selected from: cyano, nitro, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-alkoxy-C$_1$–C$_4$-alkyl, (C$_1$–C$_4$-alkoxy)carbonyl and C$_1$–C$_4$-acyl;

m is 0, 1 or 2;

Alk is 1,2-ethylidene or 1,3-propylidene, where the hydrogen atoms of these chains may be replaced independently of one another by one of the following groups: C$_1$–C$_8$-alkyl, C$_1$–C$_8$-haloalkyl, C$_2$–C$_8$-alkenyl, C$_2$–C$_8$-haloalkenyl or C$_2$–C$_8$-alkynyl, where each of these 5 radicals additionally may carry one to three groups selected from: cyano, C$_1$–C$_4$-alkoxy, C$_1$–C$_4$-haloalkoxy, C$_1$–C$_4$-alkylthio, (C$_1$–C$_4$-alkoxy)carbonyl, C$_3$–C$_7$-cycloalkyl and C$_5$–C$_7$-cycloalkenyl;

C$_3$–C$_7$-cycloalkyl and C$_5$–C$_7$-cycloalkenyl, where these radicals may be partially or fully halogenated or may carry one to three groups selected from: cyano, halogen, C$_1$–C$_4$-alkyl, C$_1$–C$_4$-haloalkyl and C$_1$–C$_4$-alkoxy;

X is oxygen or sulfur;

with the exception of those compounds where A is A1'

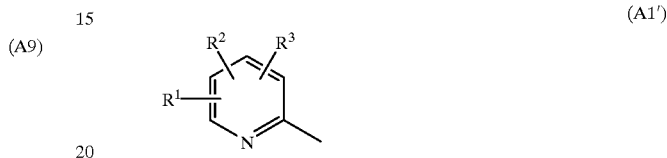

(A1')

a) R$^1$, R$^2$ and R$^3$ simultaneously are hydrogen, and
b) the compounds II.1 to II.4, II.6 to II.9 and II.18 below:

| No. | R$^1$ | R$^2$ | R$^3$ | m | Alk | X |
|---|---|---|---|---|---|---|
| II.1 | 5-Cl | H | H | 0 | 1,2-ethylidene | —O— |
| II.2 | 6-OCH$_3$ | H | H | 0 | 1,2-ethylidene | —O— |
| II.3 | 5-CF$_3$ | H | H | 0 | 1,2-ethylidene | —O— |
| II.4 | 5-CF$_3$ | H | H | 2 | 1,2-ethylidene | —O— |
| II.6 | 5-NO$_2$ | H | H | 0 | 1,2-ethylidene | —O— |
| II.7 | H | H | 3-NO$_2$ | 0 | 1,2-ethylidene | —O— |
| II.8 | H | H | 3-OCH$_3$ | 0 | 1,2-ethylidene | —O— |
| II.9 | H | H | 3-CN | 0 | 1,2-ethylidene | —O— |
| II.18 | 6-CH$_3$ | 4-(4-bromophenyl) | 3-CN | 0 | 1,2-ethylidene | —O— | and with the exception of the compound II where A is (A9), R$^1$–R$^6$ are H, m is 0, Alk is 1,2-ethylidene and X is oxygen.

* * * * *

UNITED STATES PATENT AND TRADEMARK OFFICE
CERTIFICATE OF CORRECTION

| | | |
|---|---|---|
| PATENT NO. | : 6,069,144 | Page 1 of 1 |
| DATED | : May 30, 2000 | |
| INVENTOR(S) | : Wagner et al. | |

It is certified that error appears in the above-identified patent and that said Letters Patent is hereby corrected as shown below:

Title page,
Item [30], insert the following additional priority information:

-- Dec. 27, 1995   [DE]   Germany ................... 195 48 781.8 --.

Signed and Sealed this

Twenty-fifth Day of December, 2001

Attest:

Attesting Officer

JAMES E. ROGAN
Director of the United States Patent and Trademark Office